US005658238A

United States Patent [19]
Suzuki et al.

[11] Patent Number: 5,658,238
[45] Date of Patent: Aug. 19, 1997

[54] ENDOSCOPE APPARATUS CAPABLE OF BEING SWITCHED TO A MODE IN WHICH A CURVATURE OPERATING LEVER IS RETURNED AND TO A MODE IN WHICH THE CURVATURE OPERATING LEVER IS NOT RETURNED

[75] Inventors: Akira Suzuki; Hiroki Hibino, both of Hachioji; Yoshikatsu Nagayama, deceased, late of Sagamihara; Akemi Nagayama, heiress; Yuuki Nagayama, heir, both of Kanagawa-ken; Motokazu Nakamura, Hachioji, all of Japan

[73] Assignee: Olympus Optical Co., Ltd., Tokyo, Japan

[21] Appl. No.: 400,128

[22] Filed: Mar. 6, 1995

Related U.S. Application Data

[63] Continuation of Ser. No. 10,744, Jan. 29, 1993, abandoned.

[30] Foreign Application Priority Data

| Feb. 25, 1992 | [JP] | Japan | 4-038066 |
| Aug. 6, 1992 | [JP] | Japan | 4-210434 |
| Dec. 8, 1992 | [JP] | Japan | 4-328047 |

[51] Int. Cl.[6] ............................................. A61B 1/005
[52] U.S. Cl. ........................ 600/150; 600/151; 600/146
[58] Field of Search ............................... 600/117, 118, 600/146, 151, 152, 150

[56] References Cited

U.S. PATENT DOCUMENTS

| 4,489,304 | 12/1984 | Hayes | 74/471 XY X |
| 4,893,613 | 1/1990 | Hake | 128/4 |
| 4,932,394 | 6/1990 | Nanaumi | 128/4 |
| 4,982,725 | 1/1991 | Hibino et al. | 128/4 |
| 5,159,446 | 10/1992 | Hibino et al. | 600/152 X |

FOREIGN PATENT DOCUMENTS

| 0079525 | 5/1983 | European Pat. Off. | 128/4 |
| 2070715 | 9/1981 | United Kingdom | 128/4 |

*Primary Examiner*—Richard J. Apley
*Assistant Examiner*—John Mulcahy
*Attorney, Agent, or Firm*—Armstrong, Westerman, Hattori, McLeland & Naughton

[57] ABSTRACT

A curvature section provided in an insertable section is curved in response to a curving instructing signal output by the operation of a curving operating switch. In case the curving operating switch is of a joy stick type having an operating lever, in response to the operation of a switching switch, a mode in which the inclination angle of the operating lever is held and a mode in which the inclination angle of the operating lever is returned to a neutral position in which it is zero will be switched and the curvature section will be of a curvature angle following the inclination angle of the operating lever.

In case the curving operating switch is of a joy pad type comprising a plurality of on/off switches, in response to the operation of the switching switch, the curvature instructing signal will be held or reset.

23 Claims, 52 Drawing Sheets

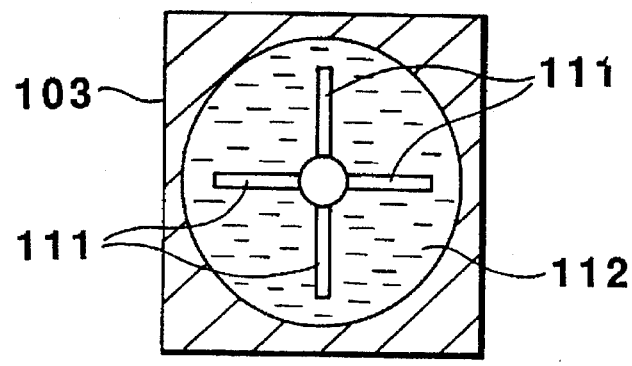
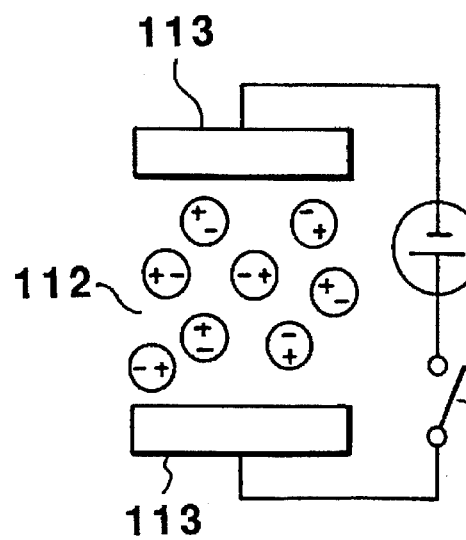
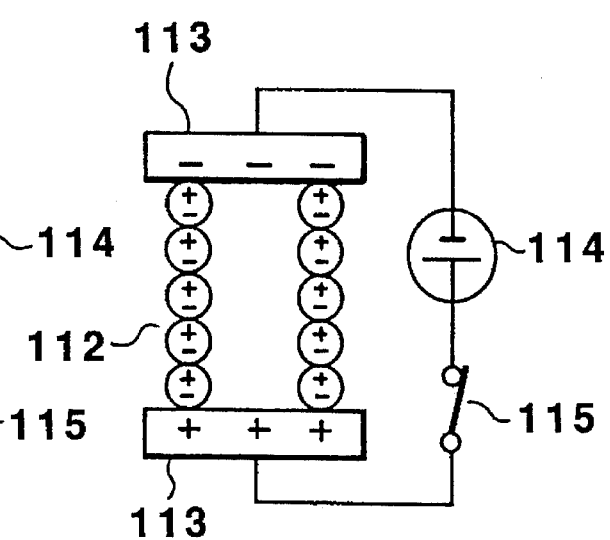

488

ENDOSCOPE APPARATUS CAPABLE OF BEING SWITCHED TO A MODE IN WHICH A CURVATURE OPERATING LEVER IS RETURNED AND TO A MODE IN WHICH THE CURVATURE OPERATING LEVER IS NOT RETURNED

This application is a Continuation application Ser. No. 08/010,744 filed Jan. 29, 1993, now abandoned.

BACKGROUND OF THE INVENTION

1. Field of the Invention

The present invention relates to an endoscope apparatus having a switching switch capable of being switched to a mode in which a curvature operating lever is returned to a predetermined position and a mode in which the curvature operating lever is not returned to the predetermined position, when a hand is released from the curvature operating lever.

2. Related Art and Prior Art Statement

In recent years, there is widely utilized an optical type or electronic type endoscope in which an elongated insertable section is inserted into a body cavity and whereby internal organs within the body cavity are observed and a treating or processing tool inserted into a processing tool channel is so used as to be able to effect various kinds of medical treatments.

In the endoscope, there has been proposed an arrangement in which a curvature portion of the insertable section is curvature-driven by such driving means as an inputting means, motor or curvature operating switch to improve the operability.

For example, in Japanese Patent Unexamined Publication (Laid Open) No. SHO 61-106125, there is disclosed a technique in which a joy stick of an input unit in which grasping or gripping a curvature angle and controlling a curvature speed can be simultaneously effected is brought to a curvature operating switch and upward, downward, leftward and rightward curvature operations are effected by operating the curvature operating switch.

Here, generally, the joy stick is sectioned into two sections by the operation of the (curvature) operating lever. The first of them is a "joy stick of a type having a neutral return" in which, when the hand is separated from the operating lever, the operating lever will forcibly return to the center and the curvature portion will also return to be straight. The second of them is a "joy stick of a type having no neutral return" in which, even when the hand is separated from the operating lever, the operating lever will not move and the curvature portion will maintain the curvature state as of just before the hand is separated. When the joy stick is considered as a curvature operating switch of an endoscope, it will be convenient to have both of the functions of the above mentioned two joy sticks.

In case the curvature portion is required to remain curved as, for example, in a living body inspection, the "joy stick having no neutral return" which will not move even if the hand is separated from the operating lever will be desirable. However, when the insertable section is to be inserted into such narrow tube cavity as of a large intestine, the "joy stick of the type having the neutral return" in which the curvature portion can be quickly straightened will be desirable.

Further, in recent years, there is a prior art having an automatic inserting mechanism in which an insertable section is automatically inserted into a body cavity. This prior art has a detecting means for a dark part within the body cavity by which the insertable section is inserted toward a deep portion while controlling the curvature of the curvature section with the output of this detecting means.

In case the automatic inserting mechanism is to be switched to a manual insertion, if the curvature state of the curvature section by the automatic insertion as of just before the switching does not coincide with a curvature indicating value by the curvature operating joy stick (that is to say, if an inclined direction and an inclined angle do not coincide with each other), the curvature section will be curved by a curvature driving means so as to coincide with the curvature indicating value of the joy stick. By this curvature operation, there is considered a danger of impacting or injuring a body wall. Therefore, it is required to prevent such dangerous situation from being generated.

OBJECT AND SUMMARY OF THE INVENTION

It is an object of the invention to provide an endoscope apparatus provided with a function of switching the presence and absence of a neutral return by one touch.

It is another object of the invention to provide an endoscope apparatus which can positively prevent a body wall and the like from being wounded or injured in the case of switching the automatic inserting mode to the manual inserting mode.

According to the present invention, there is provided an endoscope apparatus comprising:

- an endoscope provided with an elongated insertable section formed of a curvable curvature section, an illuminating light emitting means for emitting an illuminating light from the tip side of said insertable section and an objective optical system provided on the tip side of said insertable section and forming an optical image;
- a curvature switch for operating the indication of curving the above mentioned curvature section;
- a driving force generating means for generating a driving force for curving said curvature section in response to the operation of said curvature switch;
- a driving force transmitting means inserted at least through said insertable section to transmit said driving force to said curvature section; and
- a controlling means controlling the change of the indicated amount of at least said curvature switch on the basis of the operation of a change-over switch,
- so that the indicated amount of the curvature switch may be changed in response to the presence and absence of the operation of the change-over switch to return the curvature portion to the neutral state or the indicated amount of the change-over switch may be held to hold the curvature section in a curved state; the mode of the automatic insertion and the manual mode may be selected in accordance with the presence and absence of the operation of the change-over switch; in the mode of the automatic insertion, the indicated amount of the curvature switch may be changed so as to become an indicated amount corresponding to the curvature state of the automatic insertion; when switching from the mode of the automatic insertion to the manual mode, the indicated amounts of the respective modes will coincide with each other and therefore no curvature portion will be abruptly curved by change-over; and thus it may be possible to secure safety.

BRIEF DESCRIPTION OF THE DRAWINGS

FIG. 2 is an explanatory view showing a curvature driving mechanism.

FIG. 3 is a block diagram showing the formations of a motor controlling & AWS controlling unit and others.

FIG. 4 is a perspective view showing a curvature switch.

FIG. 5 is a cross-sectioned view on line A—A' in FIG. 4 showing an operating lever as inclined.

FIG. 6 is a cross-sectioned view on line B—B' in FIG. 4 showing an operating lever as inclined.

FIG. 7 is a perspective view showing an RL guide.

FIG. 8 is a perspective view showing a UD guide.

FIG. 9 is a cross-sectioned view showing the structure of the operating lever.

FIG. 12 is a cross-sectioned view on line C—C' in FIG. 11.

FIG. 13 is a cross-sectioned view on line D—D' in FIG. 11.

FIG. 14 is a perspective view showing an RL guide.

FIG. 15 is a perspective view showing a UD guide.

FIG. 16 is an elevation showing the configuration of the UD guide.

FIG. 17 is a cross-sectioned view on line E—E' in FIG. 12.

FIG. 18 is a cross-sectioned view on line F—F' in FIG. 13.

FIG. 19 is an explanatory view showing a force acting on an operating lever as inclined from the state in FIG. 17.

FIG. 20 is an explanatory view showing a force acting on an operating lever as inclined from the state in FIG. 17.

FIG. 22 is a cross-sectioned view on line GA-GB-GC-GD in FIG. 21.

FIG. 23 is a cross-sectioned view on line H—H' in FIG. 21.

FIG. 24 is a cross-sectioned view on line I—I' in FIG. 21.

FIG. 25 is a cross-sectioned view showing an operating lever as inclined in the state in FIG. 23.

FIG. 26 is a cross-sectioned view showing an operating lever as inclined in the state in FIG. 24.

FIG. 27 is a perspective view showing a rotary portion of a UD volume.

FIG. 28 is a perspective view showing a UD guide.

FIG. 29 is a perspective view showing a UD rotary shaft.

FIG. 30 is a perspective view showing a rotary portion of a volume for RL.

FIG. 31 is a perspective view showing an RL guide.

FIG. 32 is a plan view showing an RL guide.

FIG. 33 is a cross-sectioned view on line J—J' in FIG. 22 showing a block provided with a groove with which a spiral spring is engaged at the outer end.

FIG. 34 is a cross-sectioned view on line K—K' in FIG. 21.

FIG. 35 is a cross-sectioned view on line M—M' in FIG. 24.

FIG. 36 is a side view showing a hexapod member.

FIG. 37 is a side view showing a tripod member.

FIG. 38 is a cross-sectioned view showing a cover member.

FIG. 39 is a cross-sectioned view on line N—N' in FIG. 38 showing the cover member.

FIG. 40 is an explanatory view showing a hexapod member and tripod member as engaged with each other together with a cover member.

FIG. 41 is a cross-sectioned view on line P—P' in FIG. 40 showing a hexapod member and tripod member as engaged with each other.

FIG. 51 is a cross-sectioned view on line P—P' in FIG. 50.

FIG. 52 is a cross-sectioned view on line Q—Q' in FIG. 50.

FIG. 53 is a magnified view showing a relationship between a cam member and a moving member.

FIG. 54 is a view showing a cam member formed so that the radius of curvature may vary.

FIGS. 55 to 58 relate to the fifth embodiment of the present invention, FIG. 55 being a perspective view showing a curvature switch in the fifth embodiment of the present invention.

FIG. 56 is a cross-sectioned view showing the internal structure of a projecting portion.

FIG. 57 is a cross-sectioned view showing a brake chamber.

FIG. 58 is an explanatory view showing the operation in case a switch is turned off and is turned on.

FIG. 60 is an explanatory view showing an entire formation of an endoscope apparatus.

FIG. 61 is a cross-sectioned view showing the formation of a curvature switch.

FIG. 62 is a cross-sectioned view on line R—R' in FIG. 61.

FIG. 63 is a cross-sectioned view on line S—S' in FIG. 61.

FIG. 64 is a view showing the curvature switch in FIG. 61 as seen in the V direction.

FIG. 65 is a flow chart showing the operation of a curvature operation controlling means.

FIG. 67 is an explanatory view showing an endoscope image and its brightness level.

FIG. 68 is an explanatory view showing a plurality of regions extracted in a dark extracting portion.

FIG. 69 is an explanatory view showing an endoscope image pattern in a state when the tip of the endoscope excessively approaches an object to be inspected.

FIG. 70 is an explanatory view showing the operation of a central extraction operating portion.

FIG. 71 is an explanatory view for explaining the operation of this embodiment in case the tube cavity is straight.

FIG. 72 is an explanatory view for explaining the operation of this embodiment in case the tube cavity is curved.

FIG. 74 is an explanatory view showing the entire formation of an endoscope apparatus.

FIG. 75 is an explanatory view showing the formation of an essential part of a curvature driving portion provided within an operating section.

FIG. 76 is a plan view showing the formation of a curvature operating switch.

FIG. 77 is a cross-sectioned view on line U—U' in FIG. 76 showing the curvature operating switch.

FIG. 78 is a cross-sectioned view showing the formation of a touch sensor provided on a finger applying surface of the curvature operating switch.

FIG. 79 is a cross-sectioned explanatory view showing the touch sensor in FIG. 78 as pushed with a finger.

FIG. 80 is a plan view of a removal preventive within the curvature operating switch.

FIG. 82 is a block diagram showing a schematic formation of a curvature operation controlling means.

FIG. 83 is a cross-sectioned view showing the formation of a curvature switch.

FIG. 84 is a cross-sectioned view showing a curvature switch operating lever in FIG. 83 as inclined.

FIG. 86 being a schematic formation view of a curvature unit.

FIG. 87 is a flow chart for explaining the operation of the curvature unit in FIG. 86.

FIG. 89 is a cross-sectioned view on line W—W' in FIG. 88 showing the curvature operating switch therein.

FIG. 90 is a circuit diagram of the curvature operating switch in FIG. 88.

FIG. 91 is a flow chart for explaining the operation of a curvature unit.

DETAILED DESCRIPTION OF THE PREFERRED EMBODIMENTS

The respective embodiments of the present invention shall be described in the following with reference to the accompanying drawings.

Figure 1:
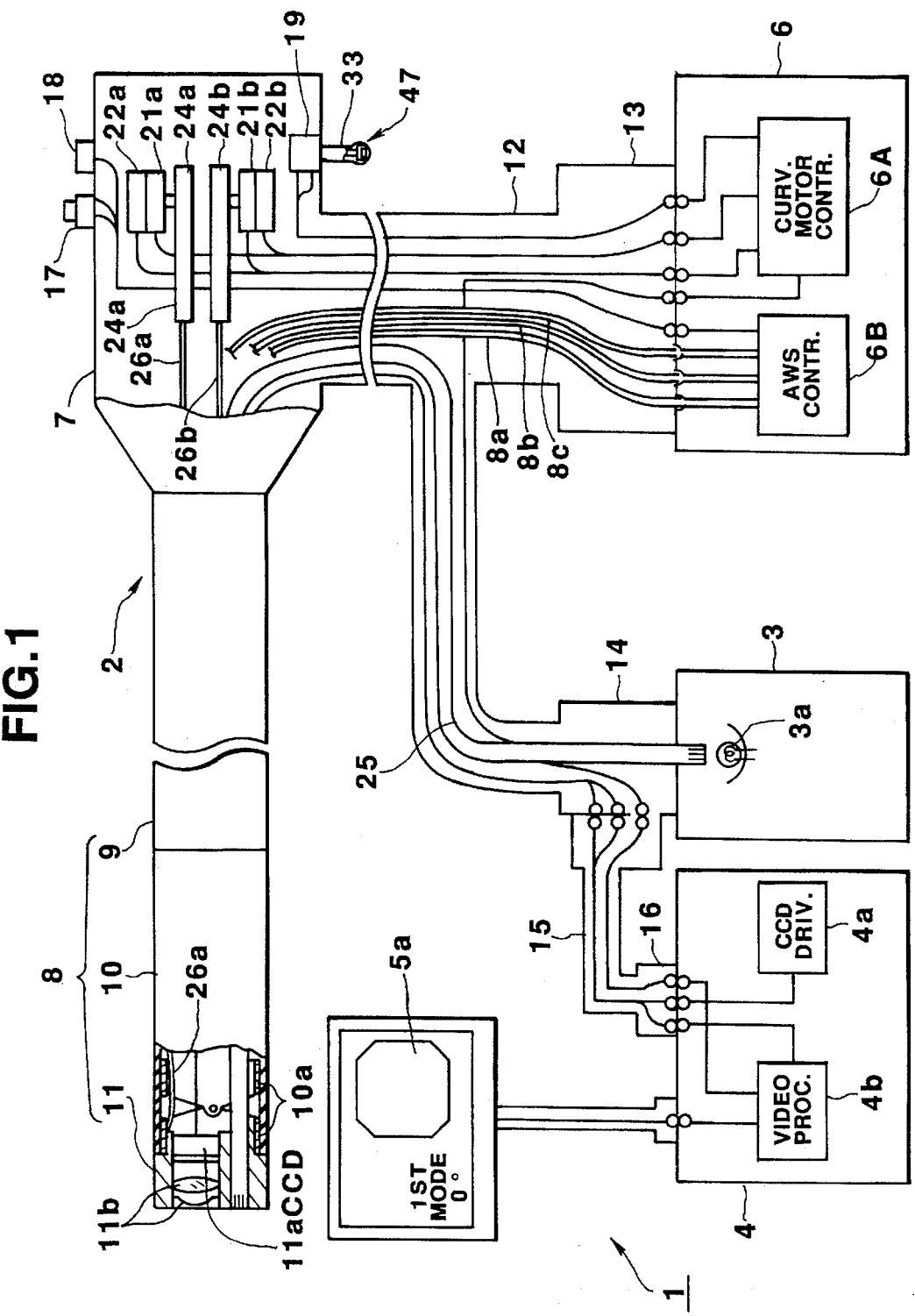
FIGS. 1 to 9 relate to the first embodiment of the present invention, FIG. 1 being an entire formation view of an endoscope apparatus of the first embodiment.

FIG. 1 shows an endoscope apparatus 1 of the first embodiment of the invention. In this embodiment, in case a curvature switch 19 is operated to curve a curvature section 10 and then an operating finger is released from the curvature switch 19, in response to the operation of a switching switch 47, a mode of maintaining the curved state and a mode of returning the curved state to a neutral position will be able to be selected and set.

The endoscope apparatus 1 illustrated in FIG. 1 comprises an electronic endoscope 2 internally provided with such solid state imaging device having a photoelectric converting function as a CCD 11a, a light source unit 3 feeding an illuminating light to this electronic endoscope 2, a video controlling unit 4 driving the CCD 11a and converting the image signal imaged by this CCD 11a to a video signal, a color monitor 5 displaying the video signal from the video controlling unit 4 and a curvature motor controlling and AWS controlling unit 6 built-in with a curvature controlling device 6A controlling the curvature of the curvature section 10 of the electronic endoscope 2 and an AWS controlling device 6B controlling the air feed/water feed and suction (abbreviated as AWS).

The electronic endoscope 2 comprises an insertable section 8 flexible so as to be insertable into an object having a tube cavity, cavity or the like and formed to be elongate and an operating section 7 formed on the base end side of this insertable section 8, held by hand and operating to insert or curve the insertable section 8.

Connected to the insertable section 8 are a bendable soft portion 9, a curvable curvature portion 10 and a hard tip forming portion 11 in the order from the operating section 7 side. The curvature portion 10 provided on the tip side of the insertable section 8 is formed by connecting a plurality of curvature pieces 10a so as to be curvable vertically and horizontally.

An illuminating light guide 25 is inserted through the insertable section and a universal cord 12 extended out of the operating section and a light guide connector 14 at the distal end of the universal cord 12 is connected to the light source unit 3 so that an illuminating light fed from an illuminating lamp 3a within the light source unit 3 may be transmitted and may be emitted from the tip (distal end) of the light guide 25 fitted to an illuminating window of the tip forming portion 11.

An optical image of an affected part or the like illuminated by this illuminating light will be formed on a CCD 11a arranged on the focal surface by an objective lens 11b fitted to an observing window in the tip forming portion 11 and will be photoelectrically converted by this CCD 11a.

This CCD 11a is connected with signal lines inserted through the insertable section 8, universal cord 12 and cable 15 connected to a light guide connector 14 and a connector 16 at the distal end of the cable 15 is connected to the video controlling unit 4 so that a CCD driving signal may be applied to the CCD 11a from the CCD driver 4a.

When this CCD driving signal is applied, the image signal photoelectrically converted from the CCD 11a will be read out and will be input into a video processing circuit 4b. By this video processing circuit 4b, the image signal will be converted to a standard video signal which will be input into the color monitor 5 and the endoscope picture of the affected part or the like imaged by the CCD 11a will be color-displayed in an endoscope picture displaying area 5a.

A connector 13 at one end of the universal cord 12 extended out of the side part of the operating section and branched on the way into two branches is detachably connected to the curvature motor controlling & AWS controlling unit 6. The air feeding tube 8a, water feeding tube 8b and suction tube 8c inserted through the insertable section 8 and universal cord 12 are connected to the AWS controlling unit 6B.

The operating section 7 is provided with a gas feeding/water feeding switch 17 for cleaning an observing window and a suction switch 18 for sucking a body liquid or the like. The signal lines connected to the gas feeding/water feeding switch 17 and the suction switch 18 are connected also with the AWS controlling unit 6B by connecting the connector 16 to the curvature motor controlling & AWS controlling unit 6.

When the air feeding/water feeding switch 17 is operated, air/water will be fed through the air feeding tube 8b/water feeding tube 8c and will be jetted from a nozzle opposed to the outer surface of the observing window (objective lens 11b) and a body liquid or the like deposited on the outer surface of the objective lens 11b will be able to be removed. This air feeding/water feeding switch 17 is formed of a two-step switch so that, in case the two-step switch is lightly pushed, the air feeding switch will be switched on but, in case it is more strongly pushed, the water feeding switch will be switched on.

Also, when the suction switch 18 is operated, the body liquid or the like obstructing the observation will be able to be sucked and removed.

Within the operating section 7 is provided a joy stick 19 which becomes a curvature operating means for curving the curvature section 10. A joy stick lever (operating lever) 33 to be held by hand in the case of curving this joy stick 19 projects out of the operating section 7.

Figure 2:
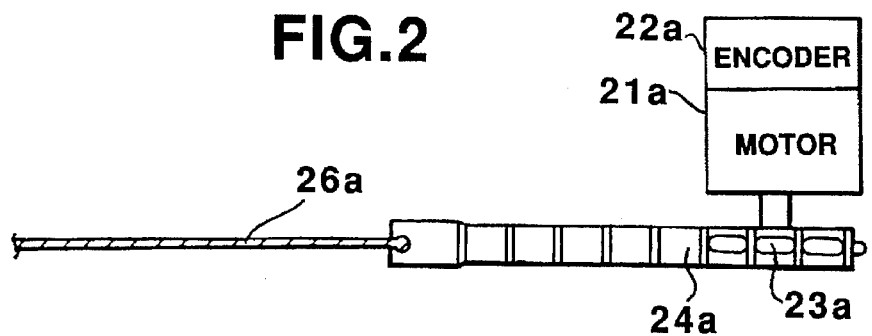

Within the operating section 7 are contained a driving motor 21a consisting, for example, of a DC motor and a driving motor 21b curving driving in the horizontal direction as a driving force generating means generating a driving force curving driving the curvature section 10 in the vertical direction. Sprockets 23a and 23b are fitted to the respective driving shafts. Chains 24a and 24b are meshed with the respective sprockets 23a and 23b. FIG. 2 shows a part of a driving mechanism driving the curvature in the vertical direction.

Curvature operating wires 26a and 26b are connected to the ends of the respective chains 24a and 24b through connecting members. The curvature operating wires 26a and 26b forming driving force transmitting means are inserted through the soft portion 9 and curvature section 10 and are connected to curvature pieces 10a at the tip of the curvature section 10 to transmit the driving force generated by the driving motors. 21a and 21b to the curvature section 10. When the driving motor 21a is rotated as shown by an arrow, for example, in FIG. 3, the upper curvature operating wire 26a will be pulled so that the upward pulling force may act on the curvature pieces 10a (See FIG. 1) to which this curvature operating wire 26a is fixed at the end to upward curve the curvature section 10.

Also, rotary encoders 22a and 22b are fitted respectively to the rotary shafts of the respective driving motors 21a and 21b. Signals corresponding respectively to the rotation amounts (rotation angles) of the respective driving motors 21a and 21b are output respectively to curvature angle detecting circuits 27a and 27b (See FIG. 3) through signal lines. The curvature angle detecting circuits 27a and 27b detect the curvature amount of the curvature section 10 and output it to a controller 28 formed of a CPU or the like.

Further, the joy stick 19 operating to indicate the curvature amount is provided with variable resistors (potentiometers) 34 and 35 for detecting the inclination amounts of the operating lever 33 in the vertical and horizontal directions. The outputs of the variable resistors 34 and 35 are input respectively into resistance value detecting circuits 29a and 29b within the curvature motor controlling unit 6A through signal lines. The resistance value detecting circuits 29a and 29b detect resistance values of the respective variable resistors 34 and 35, determine a curvature angle indicating amount for the curvature section 10 from the resistance value and output it to the controller 28.

The controller 28 compares the curvature angle indicating amount with the curvature amount of the curvature section 10 detected by the curvature angle detecting circuits 27a and 27b and controls the rotation amounts of the motors 21a and 21b through the respective (motor) drivers 30a and 30b so that the curvature amount may coincide with the curvature angle indicating amount.

When the operating lever 33 of the joy stick 19 is inclined, for example, in the vertical direction, the resistance value of the variable resistor 34 will vary in response to the inclination angle and therefore the resistance value detecting circuit 29a will detect this resistance value and will output to the controller 28 the corresponding curvature value indicating value. The controller 28 will rotate and drive the driving motor 21 so as to curve the curvature section 10 by the angle corresponding to this indicating value. As the driving motor 21 is driven, the operating wire 26 will be pulled and the curvature section 10 will be curved and driven in the vertical direction. When the curvature amount of the curvature section 10 detected by the curvature angle detecting circuit 27a coincides with the curvature angle indicating amount, the rotation and drive of the motor 21a will stop.

In case the operating lever 33 is curved and driven in the horizontal direction, the same operation will be made.

Further, the operating lever 33 of the joy stick 19 is provided at the top with a mode switching switch 47 so that, if this switching switch 47 is switched on, an interrupting terminal, for example, of the controller 28 will be made "L" to be interrupted and the controller 28 will control the mode switching.

For example, in case the mode setting flag 28a shown in FIG. 3 and set in response to the mode (mentioned as the first mode hereinafter) in which the operating lever 33 does not return is 0, when the switching switch 47 is switched on, the mode setting flag 28a will be set at 1 and spiral springs 36 and 37 formed of a shape memorizing alloy (abbreviated as SMA hereinafter) will be fed with a driving current heating them through heating circuits 49a and 49b. As later described (See, for example, FIG. 4), the spiral springs 36 and 37 elastically support the operating lever 33 on the base end side.

When the spiral springs 36 and 37 are heated to be set at a temperature above the phase transition of the SMA, they will vary to be large in the modulus of elasticity to have a force of returning the operating lever 33 to a neutral position. Therefore, when the operating lever 33 is inclined and then the hand is released, the spiral springs 36 and 37 will be in a mode (mentioned as the second mode hereinafter) of returning the operating lever 33 to the neutral position.

In the second mode, when the switch 47 is further switched on, the controller 28 will control the mode switching. That is to say, the flag 28a will be set at 0 from 1 and the heating operation by the heating circuits 49a and 49b will be stopped. In this case, the spiral springs 36 and 37 will be small in the modulus of elasticity.

Concretely, the spiral springs 36 and 37 will be of a modulus of elasticity of a value smaller than the force of returning the operating lever 33 to the neutral position. When the operating lever 33 is inclined and then the hand is released, the operating lever 33 will be in the first mode of maintaining the inclined state as of before the hand is released.

Figure 3:
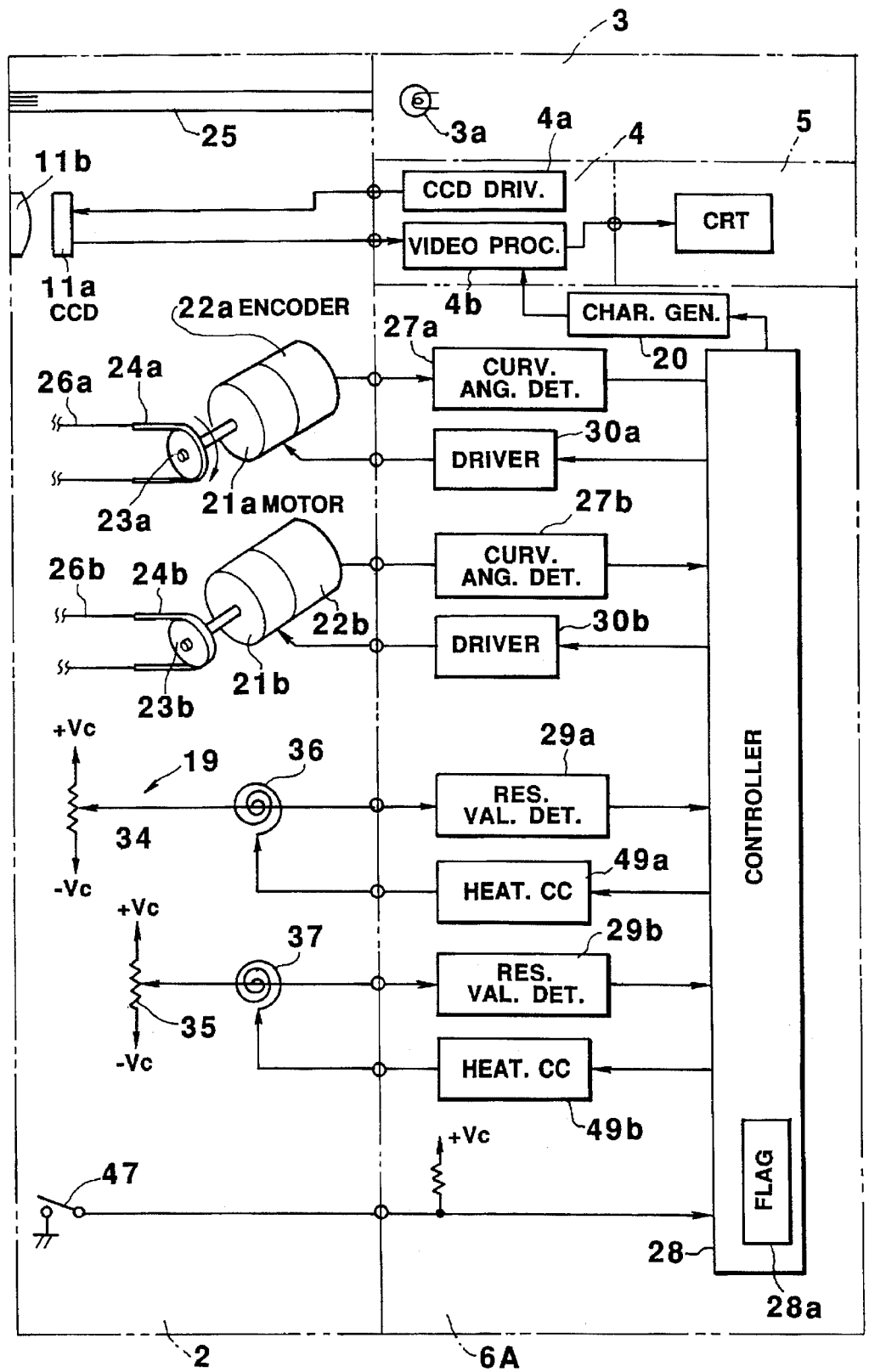

As shown in FIG. 3, the controller 28 judges the state of the flag 28a, outputs character information as to whether a mode of returning the operating lever 33 to the neutral position in the video process circuit 4b through the character generator 20 or a mode of not returning it to the neutral position, displays (as 1ST MODE, for example, in FIG. 1) this character information on the CRT picture of the monitor 5 and informs the technician (operator) of which mode the present set state is.

By the way, instead of displaying "1ST MODE", a mode not returning may be displayed. Such displaying means whereby the now selected mode is known by lighting an LED or the like by the operation of the switching switch 47 may be provided in a position near the switching switch 47, for example, at the top of the operating lever 33.

Also, the controller 28 outputs the information as to what degrees the present curvature angle is to the video process circuit 4b through the character generator 20, displays (for example, as 0 degree in FIG. 1) it on the CRT picture of the monitor 5 and informs the technician of the present curvature angle.

Figure 4:
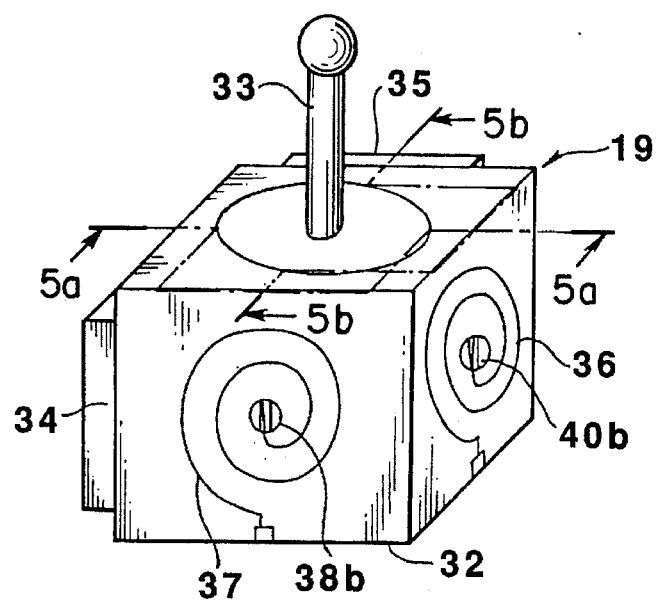

FIG. 4 is a view showing a curvature operating switch 19 unit.

The curvature operating switch 19 comprises a case 32 of a non-metallic material and an operating lever 33 of the same non-metallic material. To the case 32 are fixed a UD variable resistor 34 and RL variable resistor 35 detecting the inclining positions (inclining angles) respectively in the up and down (abbreviated as UD) direction and right and left (abbreviated as RL) direction.

These UD variable resistor 34 and RL variable resistor 35 are electrically connected respectively with resistance value detecting circuits 29a and 29b within the curvature motor controlling unit 6A to detect the inclination angle (tilting angle) of the operating lever 3 from the resistance value varying in response to the tilting angle. In case the resistance value varies from the resistance value in the neutral position, the driving motors 21a and 21b will be rotated by the amount corresponding to the varying amount.

As described above, the rotating driving amounts of the motors 21a and 21b are controlled so that the actual rotating amounts of the motors 21a and 21b detected by the rotary encoders 22a and 22b fitted to the driving motors 21a and 21b may coincide with the rotating amount indicated by the operation of the operating lever 33.

In FIG. 4, a UD spiral spring 36 made by spirally winding a plate member and having a function of neutrally returning the operating lever is provided on the opposite surface of the UD variable resistor 34 holding the case 32 and, in the same manner, an RL spiral spring 37 is provided on the opposite surface of the RL variable resistor 35. These spiral springs 36 and 37 are made of an SMA.

Figures 5A, 5B:
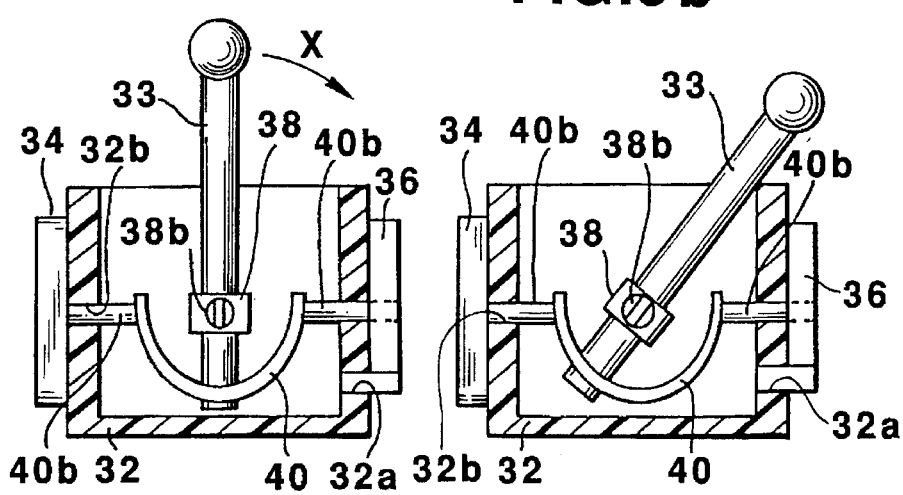
Figure 7:
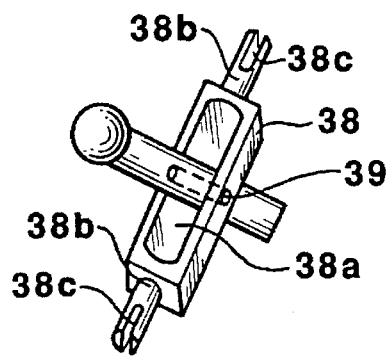
Figure 8:
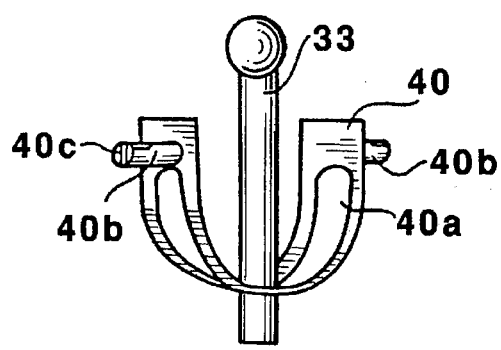

FIG. 5a is a cross-sectioned view on line A—A' in FIG. 4. The operating lever 33 is inserted through a slot 38a of such RL guide 38 as is shown in FIG. 7. The operating lever 33 is supported tiltably within the above mentioned slot 38a with respect to the RL guide 38 by a pin 39 passing through the RL guide 38 and operating lever 33.

Figure 6A:
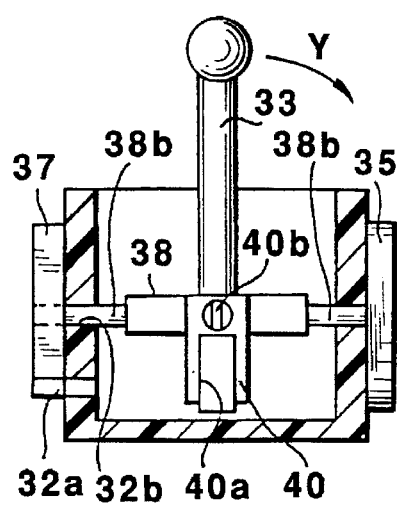

Next, as shown in FIG. 6a, the operating lever 33 is inserted through the slot 38a and is then inserted through a slot 40a provided in the UD guide 40.

Here, both RL guide 38 and UD guide 40 have at both ends columnar parts 38b and 40b respectively fixed by such means as pressing in. These columnar parts 38b and 40b are provided respectively with minus type slits 38c and 40c.

These slits are connected on one side with rotary shafts having minus type projections not illustrated of the RL variable resistor 35 and UD variable resistor 34 and are connected on the other side respectively with the RL spiral spring 37 and UD spiral spring 36. These columnar parts are rotatably supported by bores 32b provided in the case 32.

The spiral springs are inserted and fixed at the center side ends respectively into the minus type slits 38c and 40c provided respectively in the columnar parts 38b and 40b and are inserted and fixed at the outside ends respectively into bores 32a provided in the case 32.

Figure 9:
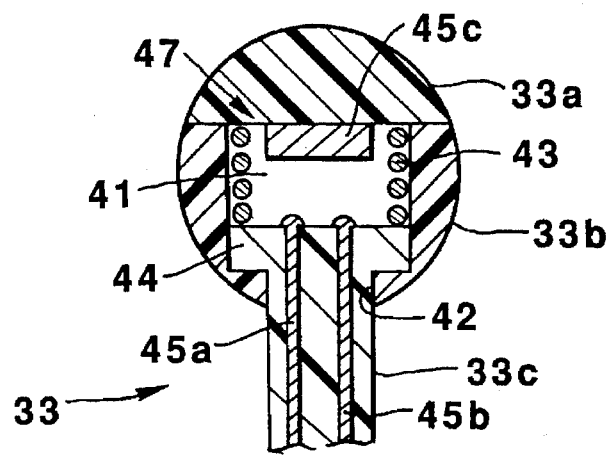

Here, as described above, the spiral springs 36 and 37 are made of an SMA and are connected at the center side end and outside end respectively to heating circuits 49a and 49b feeding a driving current so that, by the control of the controller 28 monitoring the switching on (for example, by the presence or absence of an interruption) of a switch 47 provided in the operating lever 33 shown in FIG. 9, the driving current may be flowed or interrupted.

FIG. 9 shows a cross-section of the top of the operating lever 33. The operating lever 33 comprises an upper head part 33a, lower head part 33b and shank part 33c. Here, the lower head part 33b is provided with a space 41 consisting of a countersunk bore and a through bore 42. A compression spring 43 is provided in this space to support the above mentioned upper head part 33a.

The shank part 33 has a large diameter end part 44 which is contained within the above mentioned space 41 and performs a role of preventing the end part 44 from being removed.

The shank part 33c is provided with conductors 45a and 45b inserted through the interior and having electrodes on the space side.

A conductor 45c is bonded and fixed in the upper head part 33a and the upper head part 33a and lower head part 33b are also bonded and fixed to each other. That is to say, there is provided a switch wherein, when the upper head part 33a is pushed, the compression spring 43 will be compressed, the upper head part 33a and lower head part 33b will lower, the conductor 45c fixed to the upper head part 33a will also lower and the conductors 45a and 45b will be conducted with each other.

By the controller 28 within the motor controlling unit 6A, this conduction is checked and, whenever once switched on, the electrification to the spiral springs 36 and 37 formed of an SMA from the heating circuits 49a and 49b will be controlled to be switched to the electrification, non-electrification and electrification.

The spiral springs 36 and 37 formed of an SMA are so set that, in the non-electrification state, the modulus of elasticity will be small but, on the other hand, when the spiral springs 36 and 37 are heated by the electrification and the phase transits, the modulus of elasticity will be large. That is to say, in case the modulus of elasticity is small in the non-electrification state, even if the operating lever 33 is tilted, the force of returning the operating lever to the neutral position will be small. Therefore, when the hand is released while the operating lever 33 is tilted, the operating lever 33 will hold the tilted state as of just before the hand is released. Therefore, in this non-electrification state, the joy stick 19 will be of the first mode of the non-neutral returning type.

On the other hand, in the case of a large modulus of elasticity by the electrification, when the operating lever 33 is tilted from the neutral position, the force of returning it to the neutral position will be large. Therefore, when the hand is released while the operating lever is tilted, the operating lever 33 will be returned to the neutral position. Therefore, in this electrification state, the joy stick 19 will be of the second mode of the neutral returning type.

In this first embodiment, without depending on the setting of the switching switch 47, the resistance values of the variable resistors 34 and 35 will be input into the controller 28. Therefore, in case the operating lever 33 is returned to the neutral position, the resistance values in the course of the return will be detected in turn, the detected resistance values will become a curvature indicating amount and a rotating driving current will be fed to the motors 21a and 21b. Therefore, in case the operating lever 33 is returned to the neutral position, the curvature section 10 will be also driven in the direction of releasing the curvature toward the straight state (that is, the neutral state).

Figure 10:
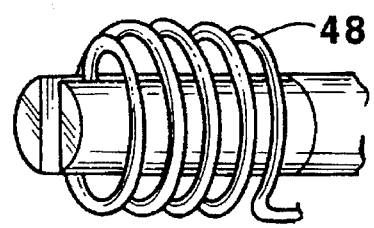
FIG. 10 is a perspective view showing a torsion spring used in place of a spiral spring in the first embodiment.

These two modes can be switched from one mode to the other by pushing down the upper head part 33a of the operating lever 33. By the way, in this embodiment, the spiral springs 36 and 37 of an SMA are used to return the operating lever 33 to the neutral position but such torsion spring of an SMA as is shown in FIG. 10 may be also used.

In such case, a columnar part will be inserted through the torsion spring 48 which is inserted and fixed at one end through the minus type slit of the columnar part and at the other end through the bore 32a of the case.

By the way, in this embodiment, the neutral return switching part is provided on the operating lever 33 but, without being limited to it, may be provided on the case 32. The operation of this embodiment shall be explained in the following.

While the spiral spring 37, for example, of an SMA is not electrified, if the operating lever 33 is inclined in the right direction (X direction in FIG. 5a), as shown in FIG. 5b, the operating lever 33 will become integral with the RL guide 38 and will tilt with the columnar part 38b as a fulcrum. In response to this tilting angle, the resistance value of the RL variable resistor 35 will vary and, by the amount corresponding to this angle, the curvature section 10 will be curved in the RL direction. At the time of this tilting, the part inserted through the UD guide 40 of the operating lever 33 will move along the slot 40a and therefore the UD guide 40 will not move.

Here, as the RL spiral spring 37 shown in FIG. 4 is fixed at the center side end to the above mentioned columnar part 38b, when the operating lever 33 is tilted, the center side end will rotate clockwise and, as the spiral spring 37 is fixed at the outside end to the case 32, the spiral spring 37 will be deformed.

Here, the moment M generated by the deformation of the spiral spring 37 is given by the next formula:

$$M = E \cdot I / (l \cdot \theta)$$

wherein E represents a longitudinal elastic modulus of the material, I represents a moment of inertia of the material (SMA), l represents a length of the material before being spirally wound and θ represents a rotation angle of the center side end in case the outside end is fixed.

Here, the SMA has such characteristics that, when it is electrified (heated), the above mentioned longitudinal elastic modulus E will become large but, when it is not electrified (cooled), the longitudinal elastic modulus E will become small.

Here, as the spiral spring 37 is not electrified and the longitudinal elastic modulus E has become small, the moment M generated by the deformation will be small. Therefore, when the energizing force to tilt the operating lever 33 is stopped as by releasing the hand from the operating lever 33, the spiral spring 37 will remain deformed and therefore the operating lever 33 will remain tilted (the curvature section 10 will also remain curved). That is to say, the operating lever 33 will operate in the curvature operating mode in which the operating lever 33 will not neutrally return.

Here, when the upper head part 33a of the operating lever 33 is pushed, the conductor 45a and 45b in FIG. 9 will conduct to each other and therefore the control part not illustrated will start electrification to the spiral spring 37 from the power source also not illustrated.

Then, the spiral spring 37 will be heated, the longitudinal elastic modulus E will become large and therefore the generated moment M of the spiral spring 37 will become large.

Here, as the spiral spring 37 is fixed at the outside end, the center side end will be rotated counter-clockwise. The operating lever 33 will also neutrally return to the original position (center) and the curvature section 10 will also return to be straight from the curved state. That is to say, the operating lever 33 will operate in the neutrally returning curvature operating mode.

Figure 6B:
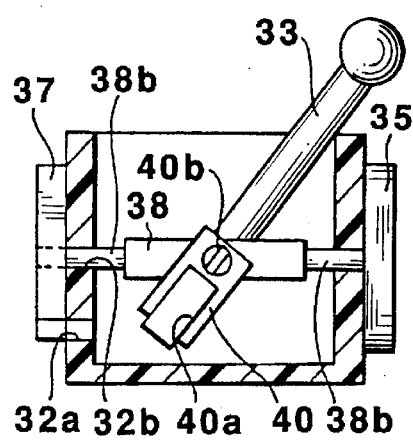

The UD (up and down) direction operation is the same. When the operating lever 33 is tilted in the upward direction (Y direction in FIG. 6a), as shown in FIG. 6b, the operating lever 33 will become integral with the UD guide 40 and will tilt with the columnar part 40b as a fulcrum. At this time, as the part inserted through the RL guide 38 of the operating lever 33 moves along the slot 38a, the RL guide 38 will not move. Here, when the columnar part 40b rotates, the spiral spring 36 will be deformed. The later operation is the same as in the above mentioned RL (right and left) direction and therefore shall not be explained here.

By the way, the operation is the same in the D (downward) direction and L (leftward) direction. This embodiment has the following effects.

By only a one-touch operation of pushing down the top of the operating lever 33, two joy sticks of a type having a neutral return and a type having no neutral return can be selected and used. Therefore, in response to the using state, the convenient one can be set and used.

By the way, there is considered an apparatus wherein, for example, the type having a neutral return is locked by an operating lever locking means so as not to neutrally return. However, in such apparatus, in the case of an operation of further inclining the operating lever, an operation of unlocking the locking means will have to be made and therefore a toilsome operation will be required. On the other hand, in this embodiment, in case the mode of a type having no neutral return is set, without the operation of unlocking the locking means, a continuous operation will be able to be made as in a joy stick of a type having no neutral return. That is to say, the respective functions of two modes are retained.

Also, in this embodiment, as the spiral spring not deformed in the axial direction is used as a neutrally returning mechanism, the neutrally returning mechanism will be able to be made small and thereby the curvature operating switch will be able to be also made small.

The second embodiment of the present invention shall be explained in the following with reference to FIGS. 11 to 20.

In this embodiment, the spiral spring formed of an SMA in the first embodiment is replaced with a compression spring formed of an SMA. The other same components as in the first embodiment shall bear the same reference numerals and shall not be explained here.

Figure 11:
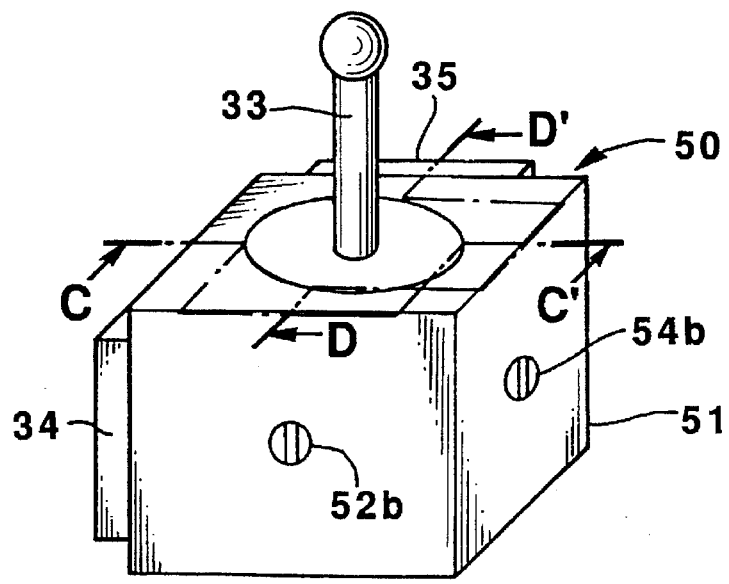
FIGS. 11 to 20 relate to the second embodiment of the present invention, FIG. 11 being a perspective view showing a curvature switch in the second embodiment.

A joy stick 50 to be a curvature operating switch shown in FIG. 11 comprises a case 51 of a non-metallic material and an operating lever 33 of the same non-metallic material. A UD variable resistor 34 and an RL variable resistor 35 are fixed to the case 51.

Figure 12:
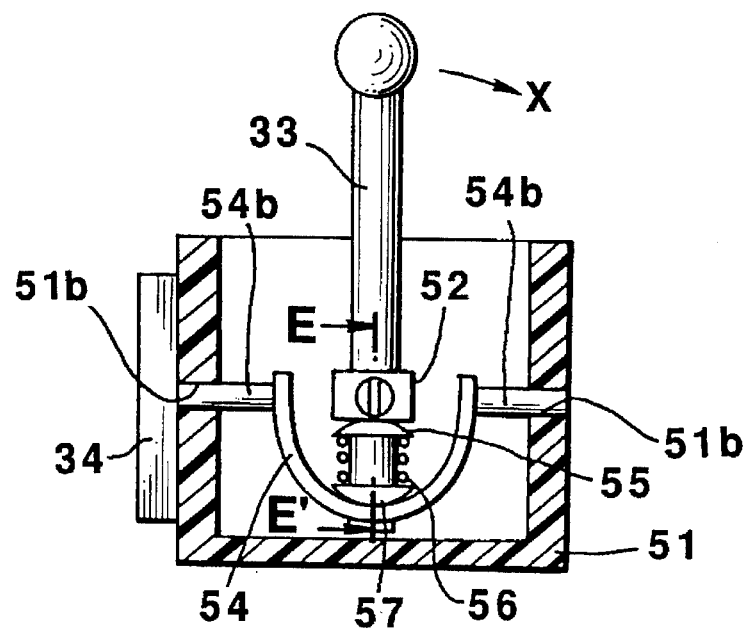

FIG. 12 is a cross-sectioned view on line C—C' in FIG. 11. The operating lever 33 passes through an RL shank 52. This operating lever 33 is made of such material passing no electricity as, for example, ceramics.

Figure 14:
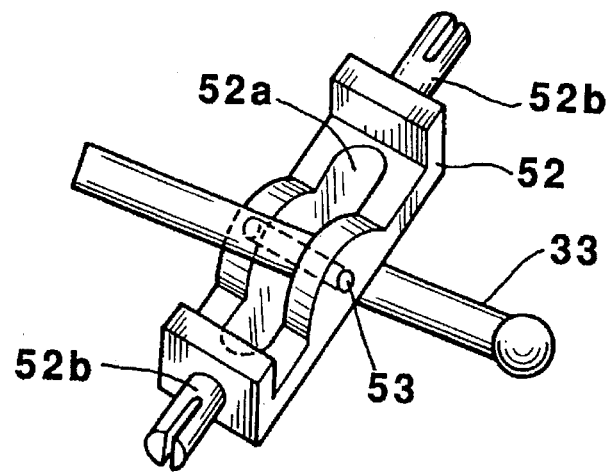

FIG. 14 shows these operating lever 33 and RL guide as connected with each other. By the way, in this view, for convenience sake, the operating lever 33 is inverted. Here, in the RL guide 52, one surface of a rectangular bar is of such configuration as is mentioned below. That is to say, it is a curved surface which is high near the center in the lengthwise direction but is gradually lower toward the outside. Beyond the curved surface, a low plane continues and both ends are high.

Also, the RL guide 52 is provided with a slot 52a through which the operating lever 33 is inserted. The operating lever 33 is tiltably supported against the RL guide 52 by a pin 53 passed through the RL guide 52 and operating lever 33.

Figure 15:
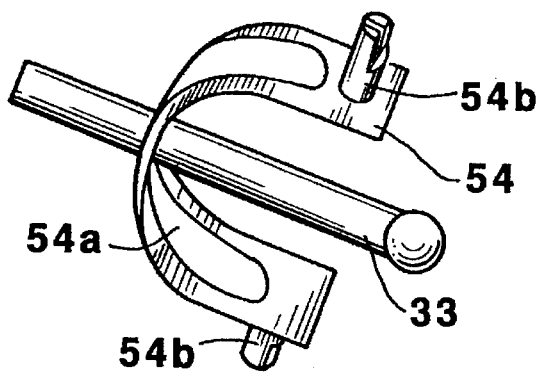

As shown in FIG. 12, the operating lever 33 is inserted through the slot 52a and is then inserted through such slot 54 provided in the UD guide 54 as is shown in FIG. 15.

Figure 16:
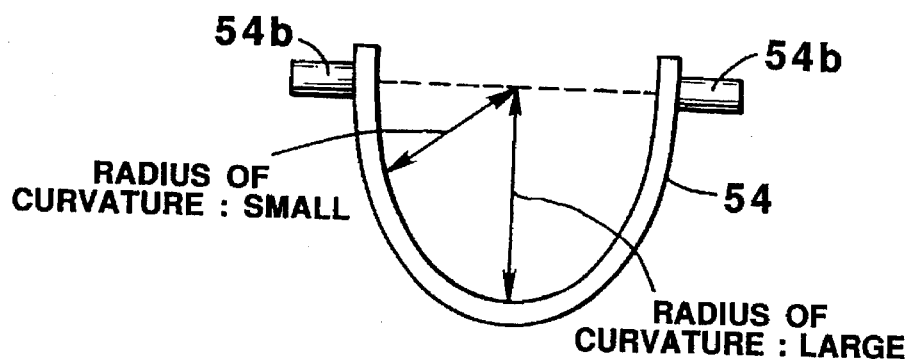

Here, the UD guide 54 is made of a plate member curved in a U-shape. When the neutral point of the later described columnar part 54b is made the center of the curved surface, the radius of curvature of this U-shape will be large near the center but will be smaller toward the end as shown in FIG. 16. The same as in the first embodiment, columnar parts 52b and 54b provided with minus type slits are pressed respectively into both ends of both of these RL guide 52 and UD guide 54 and are tiltably supported in the bores 51b provided in the case 51.

Here, in the space held by the RL guide 52 and UD guide 54, as shown in FIG. 12, in the order from the RL guide 52 side, a hemispherical ring 55 having a bore, a compression spring 56 formed of an SMA and a device-like ring 57 are provided through the operating lever 33. Here, the members of the rings 55 and 57 are made of a material passing no electricity.

Figure 13:
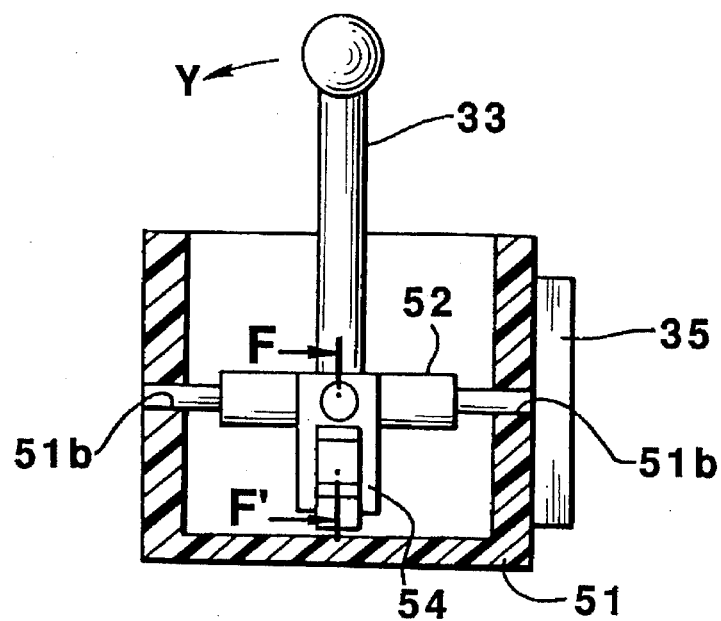
Figure 17:
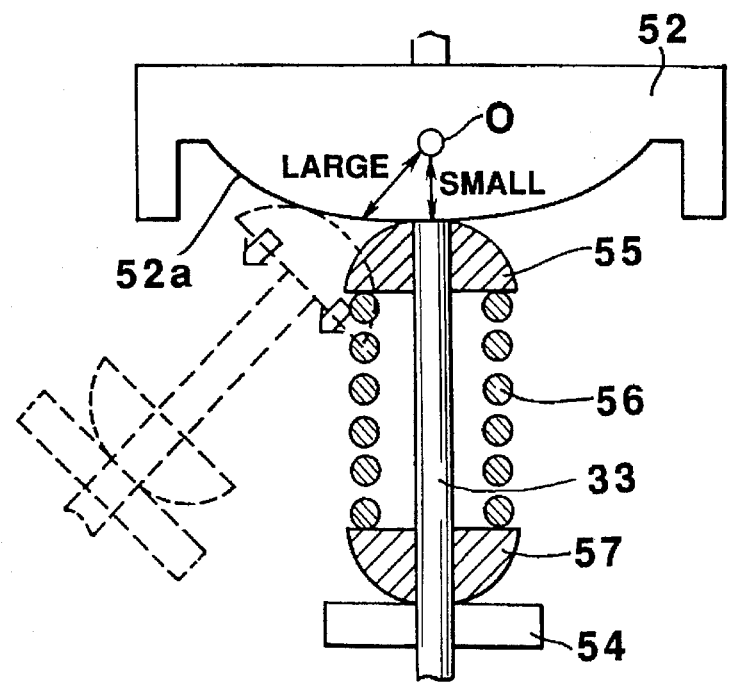

In FIG. 13, when the operating lever 33 is inclined in the Y direction, as shown in FIG. 17, the operating lever 33 will incline within a stretching bore 52a provided in the RL guide 52.

Here, as the UD guide 54 inclines integrally with the operating lever 33, the distance from the rotation center O to the UD guide 54 will not vary. The ring 57 in contact with the UD guide 54 will not also vary in the distance from the rotation center O. However, as the contact surface with the RL guide will become farther than the rotation center O when inclined, the ring 55 will move in the direction indicated by the arrow. That is to say, the compression spring 56 will be compressed.

Figure 18:
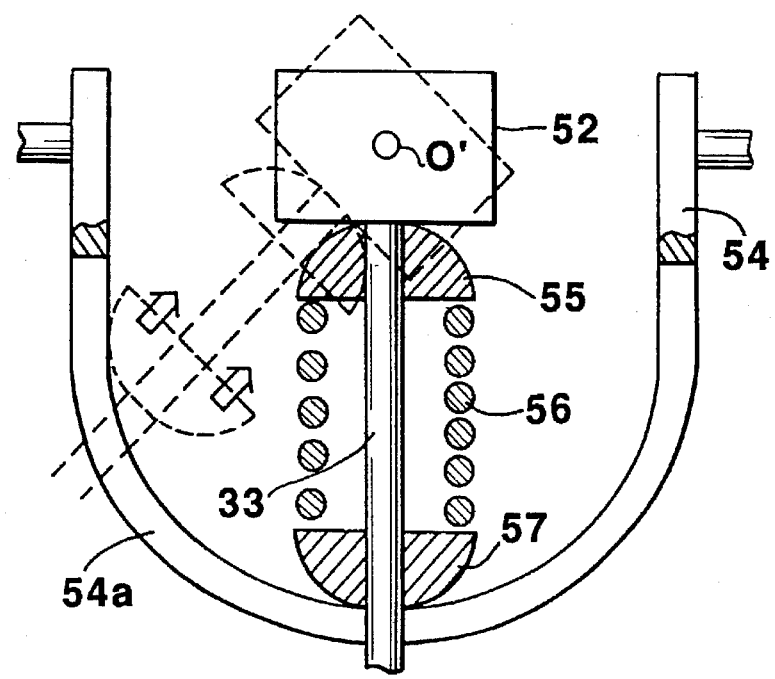

Now, in FIG. 12, when the operating lever 33 is inclined in the X direction, as shown in FIG. 18, the operating lever 33 will incline within a slot 54a provided in the UD guide 54. Here, as the RL guide 52 inclines integrally with the operating lever 33, the distance from the rotation center O' to the RL guide 52 will not vary.

The ring 55 in contact with the RL guide 52 will not also vary in the distance from the rotation center. However, as the radius of curvature of the U-surface of the UD guide 54 which is a contact surface becomes smaller toward the end as described in FIG. 16, the ring 57 will approach the rotation center O'. That is to say, the compression spring 56 will be compressed.

As described above, in whatever direction from the center the operating lever 33 may be inclined, the compression spring 56 will be compressed and deformed.

Here, a heating power source not illustrated is connected to both ends of the SMA compression spring 56 so that a circuit formation in which, whenever the upper head part 33a shown in FIG. 9 is pushed, the electrification, non-electrification and electrification will be repeated. The operation shall be explained in the following.

For example, when the compression spring 56 non-electrically inclines the operating lever 33 in the Y direction in FIG. 13, as shown in FIG. 17, the compression spring 56 will be compressed and deformed by the movement of the ring 55. Here, the stress $\tau o$ generated by the deformation of the compression spring is given by the following formula:

$$\tau o = d \cdot G \cdot \delta / (\pi \cdot Na \cdot D \cdot D)$$

wherein d represents an element wire diameter of the spring, Na represents a number of windings of the spring, D represents a diameter of the spring, $\delta$ represents a deformation amount and G represents a transverse elastic modulus. Here, the SMA has characteristics that the transverse elastic modulus will be small when no electricity is passed but will be large when electricity is passed for heating.

That is to say, when no electricity is passed, even if the spring is deformed, the transverse elastic modulus G will be so small that the spring will remain deformed. Therefore, when no electricity is passed, an operating mode having no neutral return will be made.

Figure 19:
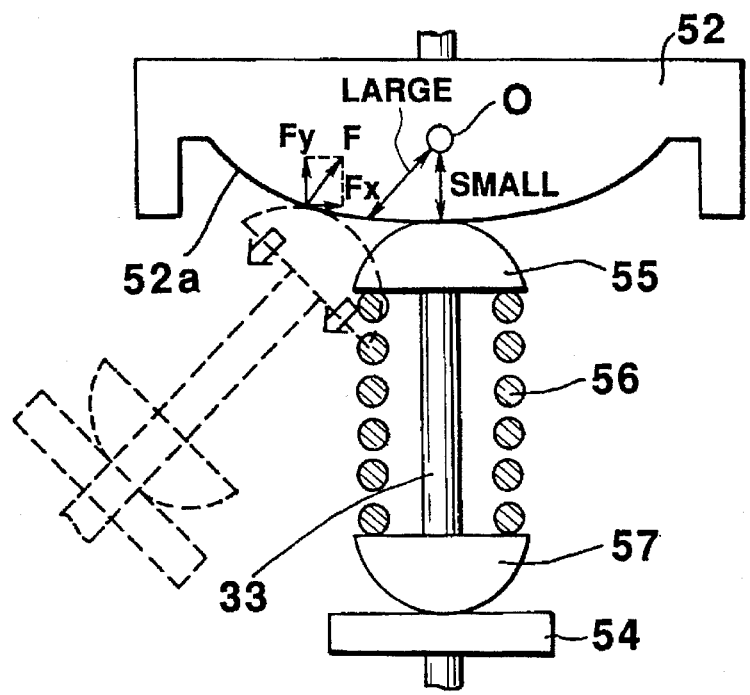

On the other hand, when the compression spring 56 is heated by passing electricity, the transverse elastic modulus G will become large and therefore the generated stress $\tau o$ will also become large. Here, as shown in FIG. 19, the force F with which the compression spring 56 pushes the RL shank 52 through the ring 55 is analyzed into Fx and Fy and, by Fx, the operating lever 33 neutrally returns.

Figure 20:
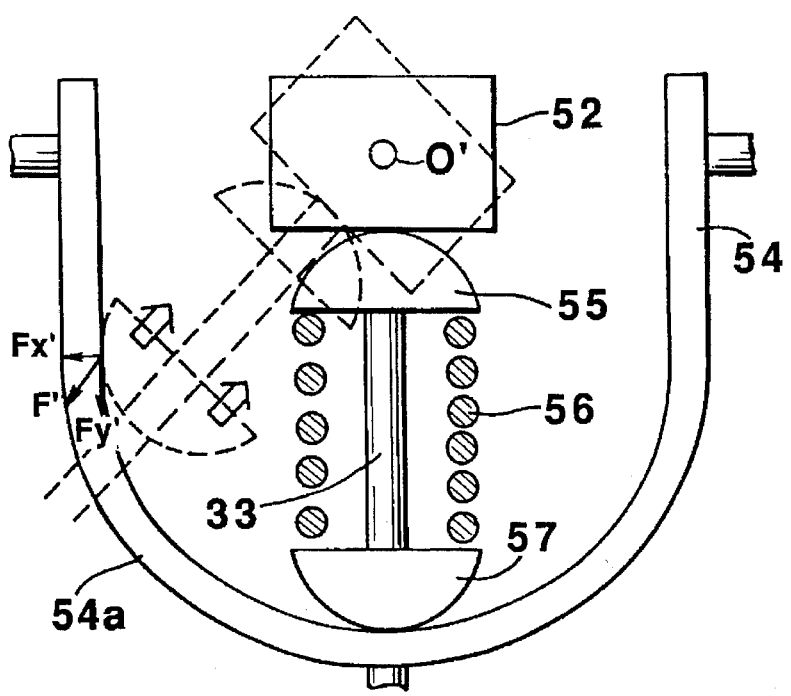

In FIG. 12, when inclined in the X direction, the same as is shown in FIG. 20, the force F' with which the SMA compression spring 56 pushes the UD shank 54 through the ring B57 will be analyzed into Fx' and Fy' and, by Fy', the operating lever 33 will neutrally return. Therefore, when electricity is passed, the operating mode having the neutral return will be made.

The effect of this embodiment is substantially the same as of the first embodiment.

The third embodiment shall be explained in the following with reference to FIGS. 21 to 41.

In this embodiment, the material of the spiral spring of the first embodiment is replaced with another metal (iron, for example, in this embodiment) than an SMA and a friction mechanism selectively obstructing or inhibiting the rotation of the operating lever is newly provided.

Figure 21:
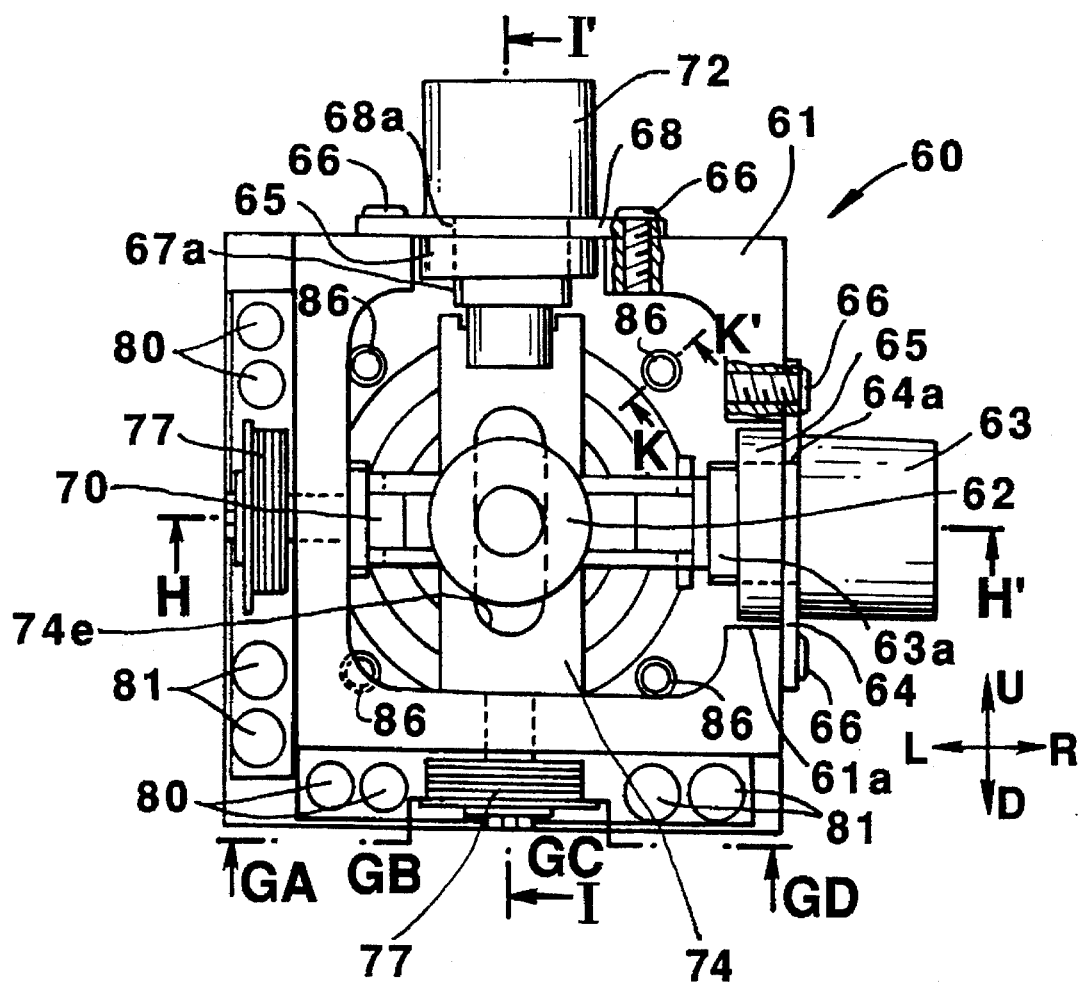
FIGS. 21 to 41 relate to the third embodiment of the present invention, FIG. 21 being a plan view showing a curvature switch in the third embodiment of the present invention.
Figure 22:
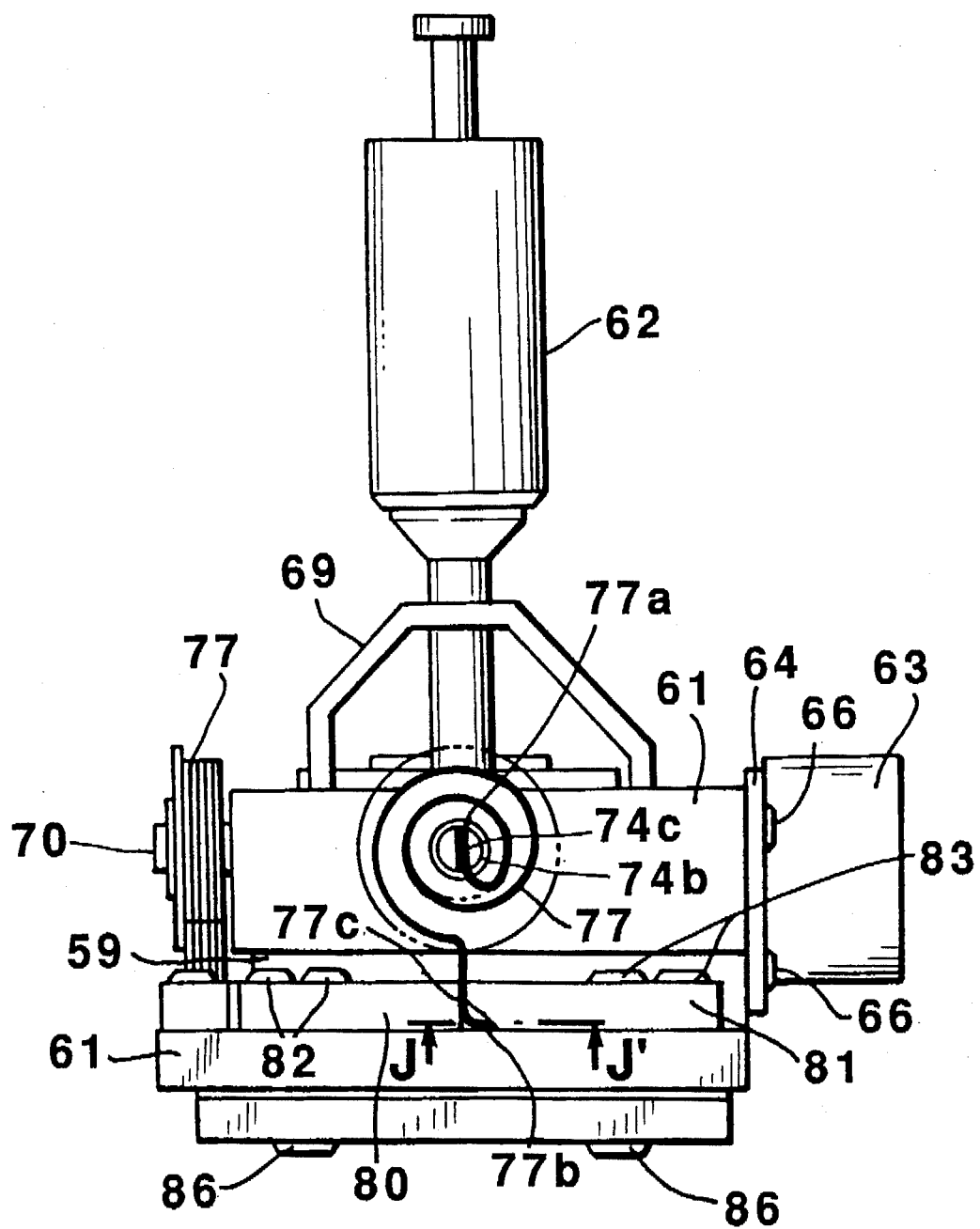

As understood from FIGS. 21 and 22, a curvature operating switch 60 comprises a case 61 and operating lever 62.

Here, the following components are fixed to the case 61.

A UD variable resistor 63 detecting the rotation angle in the UD direction of the operating lever 62 has its male screw part 63a inserted through a bore 64a provided in a UD variable resistor fixing plate 64 and the UD variable resistor 63 and UD variable resistor fixing plate 64 are connected with each other by fastening the UD variable resistor fixing plate 64 with a nut 65.

Here, the UD variable resistor fixing plate 64 is fixed to the case 61 by four screws 66. At this time, the nut 65 is positioned in a variable resistor groove 61a provided in the case 61 and the nut 65 and case 61 do not interfere with each other.

The RL variable resistor 72 fixing method is also exactly the same and the RL variable resistor 72 and RL variable resistor fixing plate 68 are connected with each other by fastening the nut 65 and are then fixed to the case 61 by the screws 66.

First of all, the operating lever 62 rotating angle detecting mechanism shall be explained.

Figure 23:
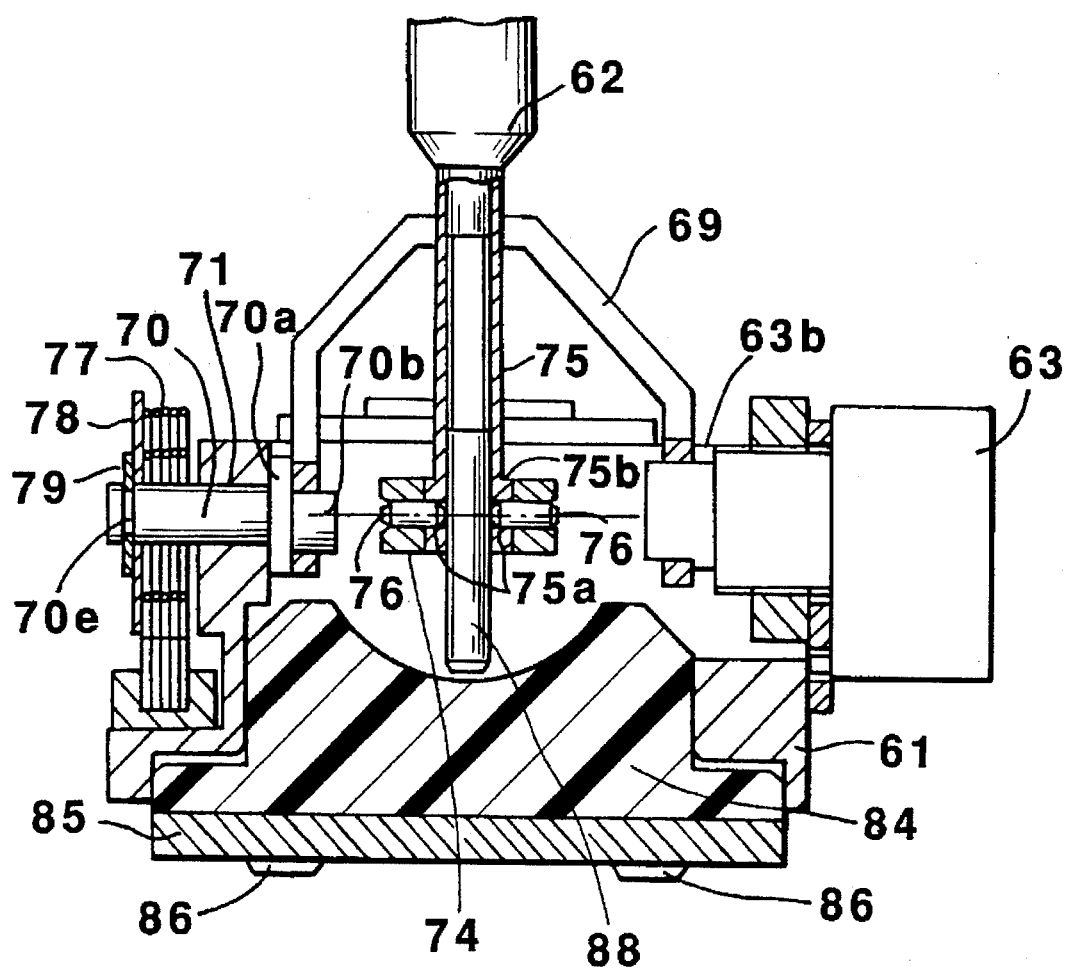
Figure 27:
Figure 28:
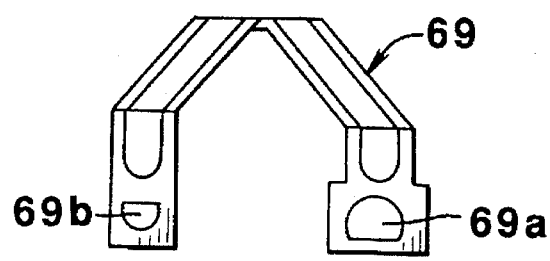
Figure 29:
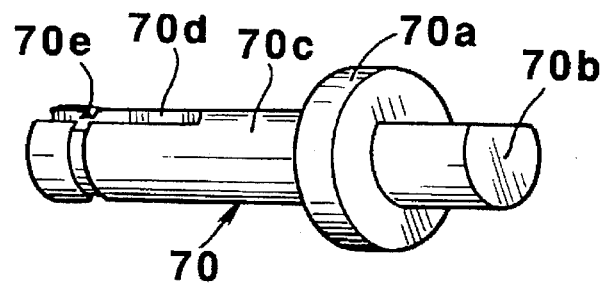

FIG. 23 is a cross-sectioned view on line H—H' in FIG. 21. As shown in FIG. 27, the rotary part 63b of the UD variable resistor 63 is like a D-shaped projection made by cutting the lower side of one end part of a column. Here, this D-shaped projecting part is inserted and fixed in a D-shaped bore 69a in a UD guide 69 made by polygonally bending a plate member having such long slit as is shown in FIG. 28.

A D-shaped bore 69b is provided at the opposite side end of this UD guide 69. As shown in FIG. 23, a supporting part 70c supported in a bore 71 provided in the case 61 and a D-shaped projecting end part 70b (See FIG. 29) having a flange part 70a preventing an outward removal are inserted and fixed in this bore 69b.

On the opposite side holding the flange part 70a of this D-shaped projecting end part 70b are the supporting part 70c as mentioned above, a minus type slit part 70d fixing the later described five UD spiral springs 77 and a this spiral spring 77 removal preventing E ring fixing groove 70e.

Figure 24:
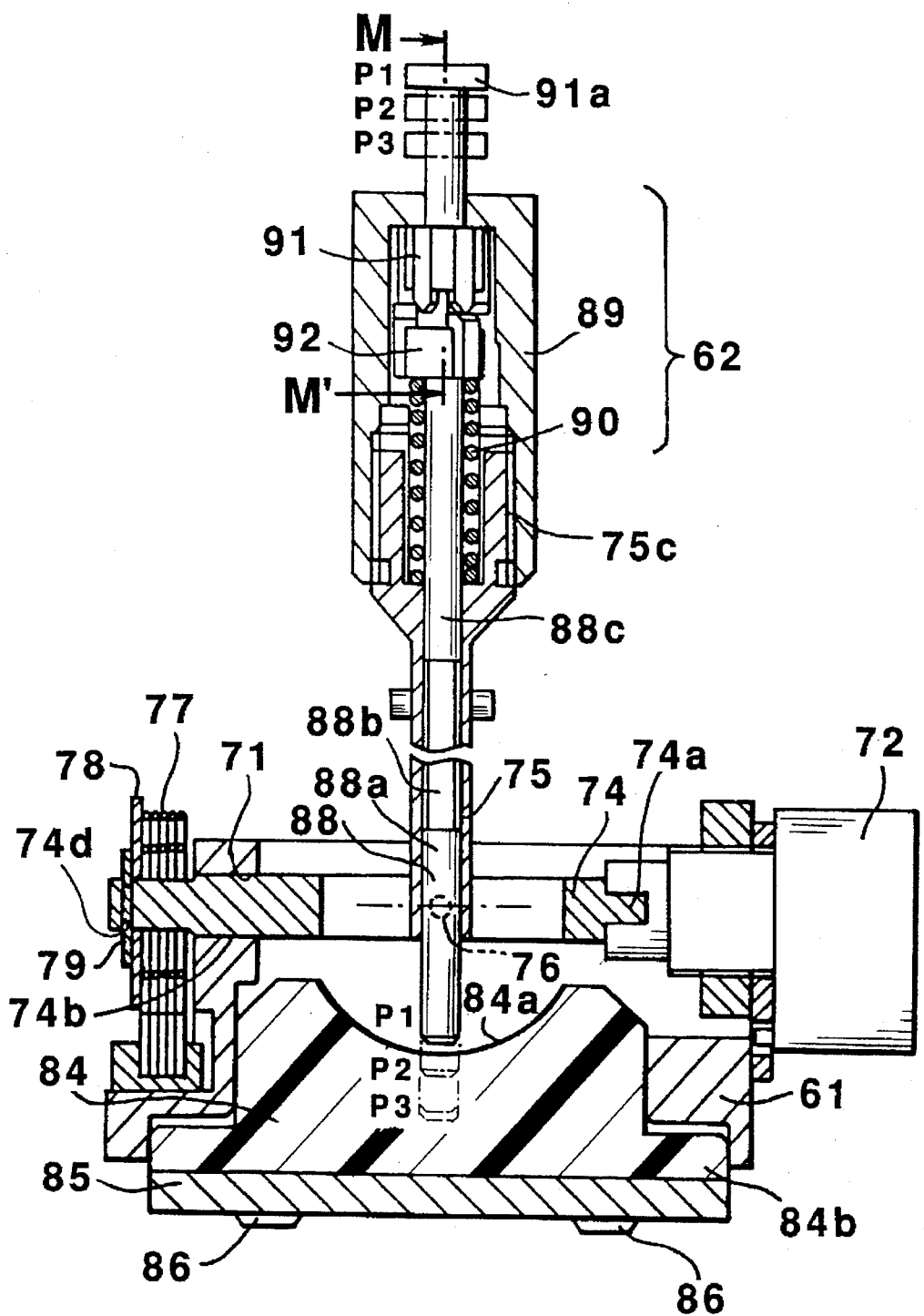
Figure 30:
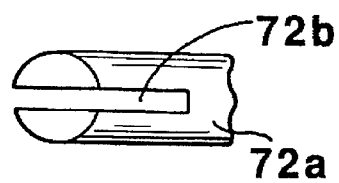

FIG. 24 is a cross-sectioned view on line I—I' in FIG. 21. As shown in FIG. 30, a minus type slit part 72 is formed in the rotary part 72a of the RL variable resistor 72. Here, when the minus type projecting part 74a of the RL guide 74 in FIG. 24 is inserted into this minus type slit part 72b, both of them will be connected and fixed with each other.

Figure 31:
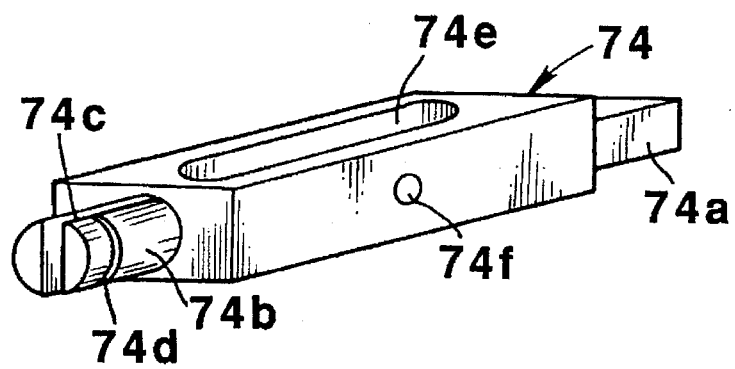

This RL guide 74 is a member in which an oval slot 74e is formed through a rectangular plate as will be seen from FIG. 31. The supporting part 74b and one end thereof are provided with minus type projections 74a as described above. This supporting part 74b is provided at the other end with a minus type slit part 74c and E-ring fixing groove 74d as shown in FIG. 31. This supporting part 74b is rotatably supported by a bore 71 provided in the case 61.

Figure 32:
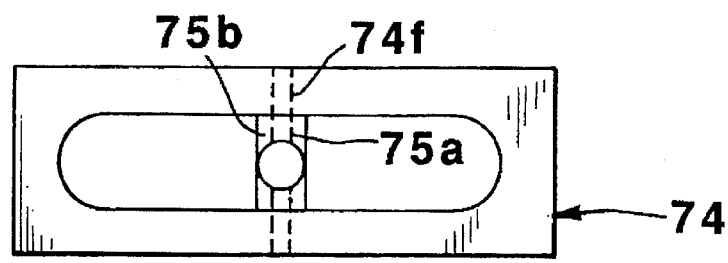

Here, the hollow outer tube part 75 of the operating lever 62 is inserted as shown in FIG. 23 into the oval slot 74e formed as mentioned above in the RL guide 74. The place where the outer tube part 75 is inserted through the oval slot 74e is a prismatic part 75b as shown in FIG. 32. Respectively two bores 75a are provided on the surfaces in the lengthwise direction of the prismatic part 75b. That is to say, the two bores 75a are provided on the thick sides of the prismatic part.

Also, the RL guide 74 is provided with a bore 74f into which respectively two pins 76 are pressed and fixed. By the way, as shown in FIGS. 23 and 24 (and FIG. 25), the respective axial centers of the pin 76, UD variable resistor 63 and RL variable resistor 72 are all in the same plane. Here, the bore diameter of the bore 75a in the outer tube part 75 is larger than the shank diameter of the pin 76. That is to say, the outer tube part 75 will tilt within the oval bore 74e in the RL guide 74 with the pin 76 as a tilting center.

Figure 26:
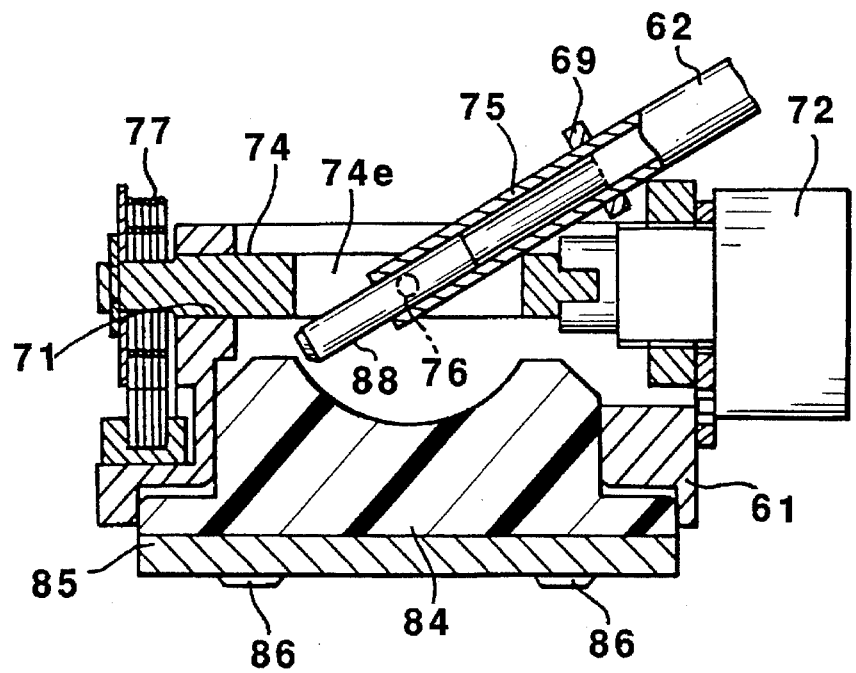

By the way, this tilting angle is, for example, 60 degrees in the U direction and 60 degrees in the D direction (See FIG. 26). At this time, the UD guide 69 will tilt integrally with the outer tube part 75, the rotary part 63b of the UD variable resistor 63 connected with the UD guide 69 will rotate and the UD variable resistor 63 will detect the rotation angle in the UD direction of the outer tube part 75, that is, of the operating lever 62.

Figure 25:
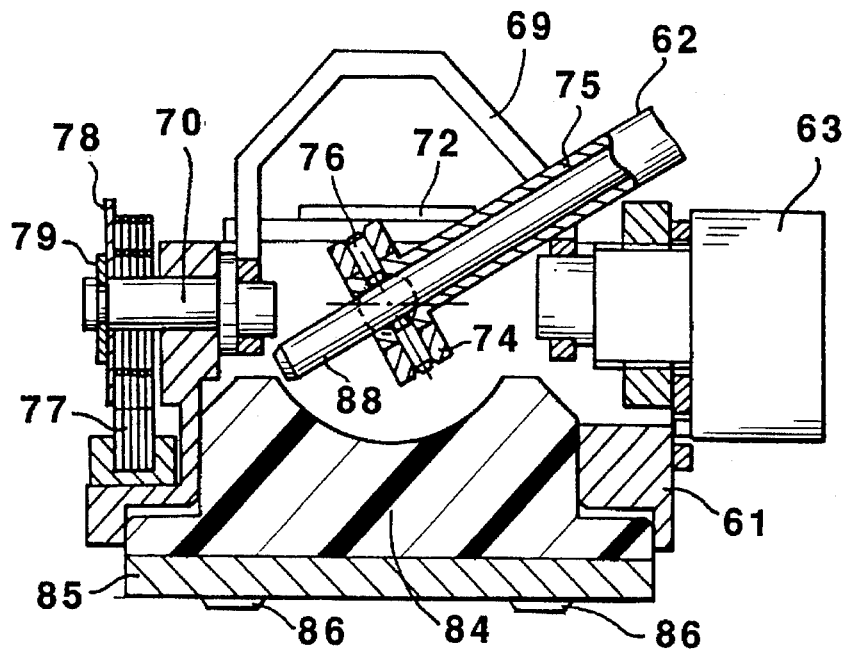

FIG. 25 is a view of the operating lever 62 as tilted in the RL direction contrary to the above. At this time, the outer tube part 75 will become integral with the RL guide 74 and will tilt within the slit of UD guide 69. By the way, this tilting angle is, for example, 60 degrees in the R direction and 60 degrees in the L direction. Here, the rotary part 72a of the RL variable resistor connected with the RL guide 74 will rotate and the RL variable resistor 72 will detect the rotation angle in the RL direction of the outer tube part 75, that is, of the operating lever 62.

As in the above, the rotation angle of the operating lever 62 will be detected by the UD variable resistor 63 and RL variable resistor 72.

The operating lever 62 neutrally returning mechanism shall be explained in the following.

FIG. 22 is a cross-sectioned view on line GA-GB-GC-GD in FIG. 21. Five spiral springs 77 made of iron wire members have the center side ends 77a fitted and inserted in a minus type slit 74c provided in the supporting part 74b of the RL guide 74 of the configuration shown in FIG. 31, are then pressed on the outside with a hollow disk 78 larger than the spiral springs 77 and have an E-ring 79 fixed in a fixing groove 74d so as to be connected with the RL guide.

By the way, the spiral springs 77 are connected with the UD shank 70 in the same manner. That is to say, as shown in FIG. 23, the spiral springs 77 have the center side ends 77a inserted through a slit 70d (See FIG. 29) in the UD shank 70 and are then connected by the disk 78 and E-ring 79.

Returning to FIG. 22, there are blocks 80 and 81 on the outside end 77b side of the spiral springs 77 rotatably and elastically supporting the RL guide 74 at the end. Here, the case 61 is provided with a groove 59 which is an escape for gaining the widths of the blocks 80 and 81. The block 80 is fixed to the case 61 by two screws 82. The block 81 is fixed to the case 61 in the same manner by two screws 83. The spiral springs 77 are held in the vertical parts 77c by these two blocks 80 and 81 so as to be fixed.

Figure 33:
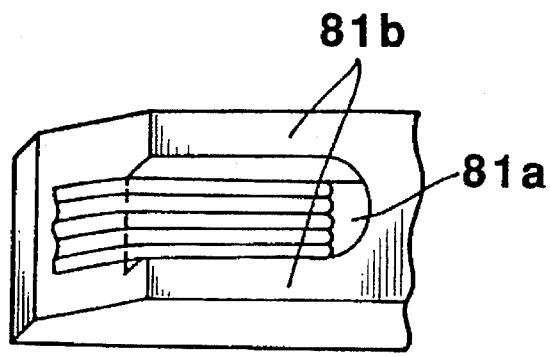

As shown in FIG. 33 which is a cross-sectioned view on line J—J' in FIG. 22, the block 81 is provided on the surface in contact with the case 61 with a groove 81a which the outside ends 77b of the above mentioned spiral springs 77 enter to be arranged and fixed not to be slipped in the horizontal direction by both side walls 81b. By the way, the UD shank side fixing method is the same and shall not be explained here.

That is to say, in this formation, when the operating lever 62 is tilted, the UD guide 69 and RD guide 74 will tilt and the spiral springs 77 connected with them will rotate at the center side ends. Here, as the outside ends 77b are fixed, the spiral springs 77 will be deformed and the stress generated by the deformation will become a returning force to return the operating lever 62 to the neutral state. In this embodiment, the five spiral springs 77 are formed of a material having an elastic force to return the operating lever 62 to the neutral state in case it is tilted.

The mechanism of switching the presence and absence of the neutral return of the operating lever shall be explained in the following. As shown in FIG. 24, a stopper rubber member 84 having a bowl-shaped recess 84a and a flange part 84b is inserted into the case 61 and is supported below with a rigid disk rubber presser 85 for preventing the deformation of the rubber.

Figure 34:
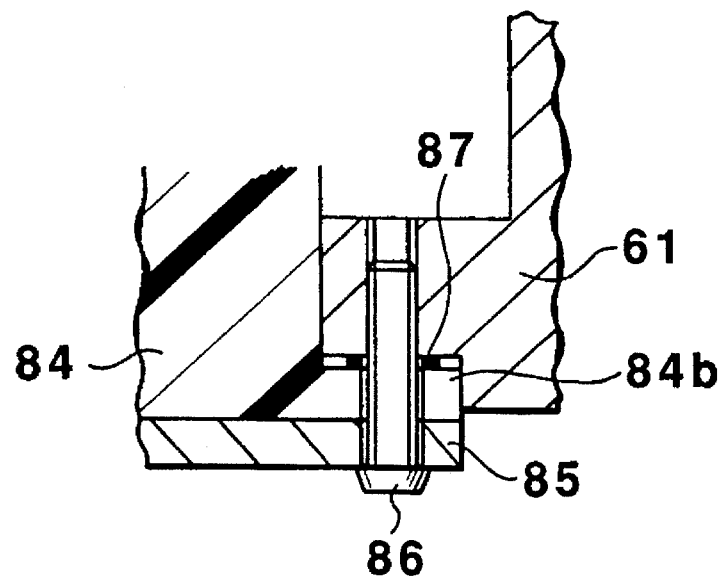

When four screws 86 fixing the rubber presser 85 are fastened to the case 61, as shown in FIG. 34 which is a cross-sectioned view on line K—K' in FIG. 21, the four screws will be inserted through the rubber presser 85, the flange part 84b of the stopper rubber member 84 and washers 87 and will be fastened to the case 61.

The inserted amount of the stopper rubber member 84 into the case 61 can be varied by varying the number of sheets of the washers 87.

Here, a pressing shaft 88 projecting from the outer tube part 75 is provided above the bowl-shaped recess 84a of the stopper rubber member 84. When the pressing part 91a of the later described hexapod member 91 is pushed once, the tip of the pressing shaft 88 will move to P1→P3→P2 and will be stationary at P2. Here, when the pressing part 91a pushed once more, the tip will move to P2→P3→P1 and will be stationary at P1.

That is to say, whenever the pressing part 91a is pushed, the tip of the pressing shaft 88 will be positioned at P1→P2→P1→P2. Here, in the position of P1, the tip of the pressing shaft 88 will float from the bowl-shaped recess 84a and will be in a mode of returning to the neutral position. On the other hand, in the position of P2, the tip of the pressing shaft 88 will push the bowl-shaped recess 84a and will be in a mode of not returning to the neutral position in which the operation of returning to the neutral position is inhibited. This structure shall be explained in the following.

The upper side end opposite the RL guide 74 of the outer tube part 75 is a large diameter screw part 75c into which the later described cover part 89 is screwed. The above described pressing bar 88 is inserted through the hollow part of the outer tube part 75 and comprises a lower part 88a, intermediate part 88b and upper part 88c.

Figure 35:
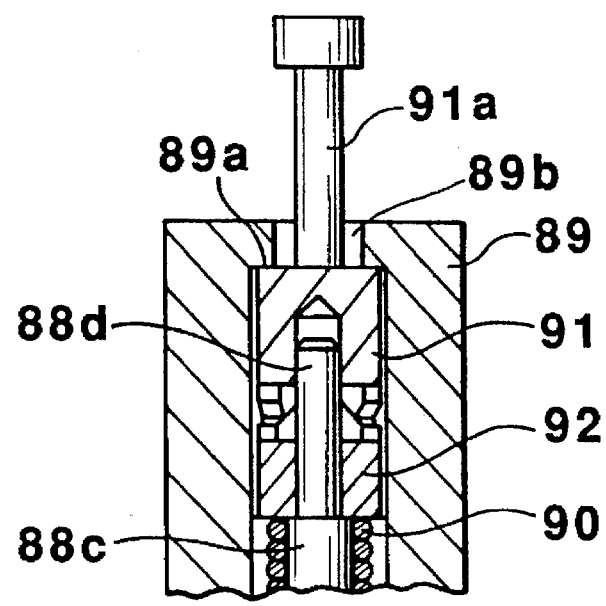

The intermediate part 88b is smaller in the diameter than the lower part 88a and upper part 88c so that the friction with the hollow part of the outer tube part 75 may be small. Here, a compression spring 90 is inserted through the upper part 88c side and, above it, as shown in FIG. 35 which is a cross-sectioned view on line M—M' in FIG. 24, the uppermost part 88d smaller in the diameter than the upper part 88c passes through a bore within the tripod member 92 and is contained in a bore within the hexapod member 91.

Here, the uppermost part 88d and tripod member 92 are fixed with each other by such means as bonding. However, the uppermost part 88d and hexapod member 91 are not fixed with each other but are rotatable and movable.

Also, in the above mentioned P1 state, the hexapod member 91 will be abutted against the bottom 89a arranged on the upper side of the cover 89 by the energizing force of the compression spring 90. This bottom 89a is provided with a through bore 89b through which the pressing part 91a of the hexapod member 91 project out of the cover 89.

Figure 36A:
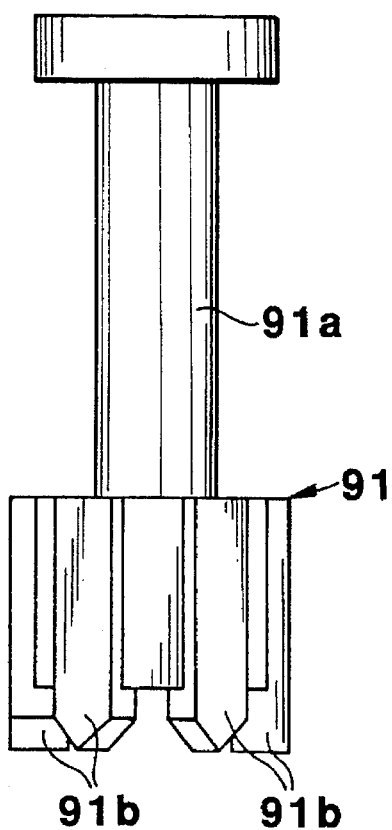
Figure 36B:
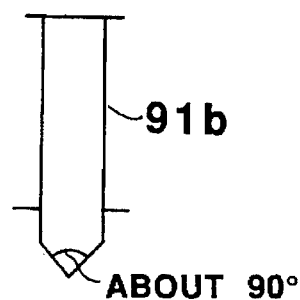

Here, the hexapod member 91 is of the configuration shown in FIG. 36a and has six legs 91b at intervals of 60 degrees. Each leg 91b is high in the center but is low on both sides and the apex angle is about 90 degrees as shown in FIG. 36b.

Figure 37:
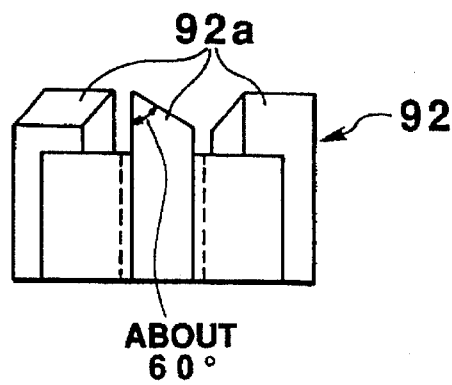

Next, the tripod member 92 is of the configuration shown in FIG. 37 and has three legs 92a at intervals of 120 degrees. Each leg 92a is high on one side but is low on the other side and the apex angle is about 60 degrees.

Figure 38:
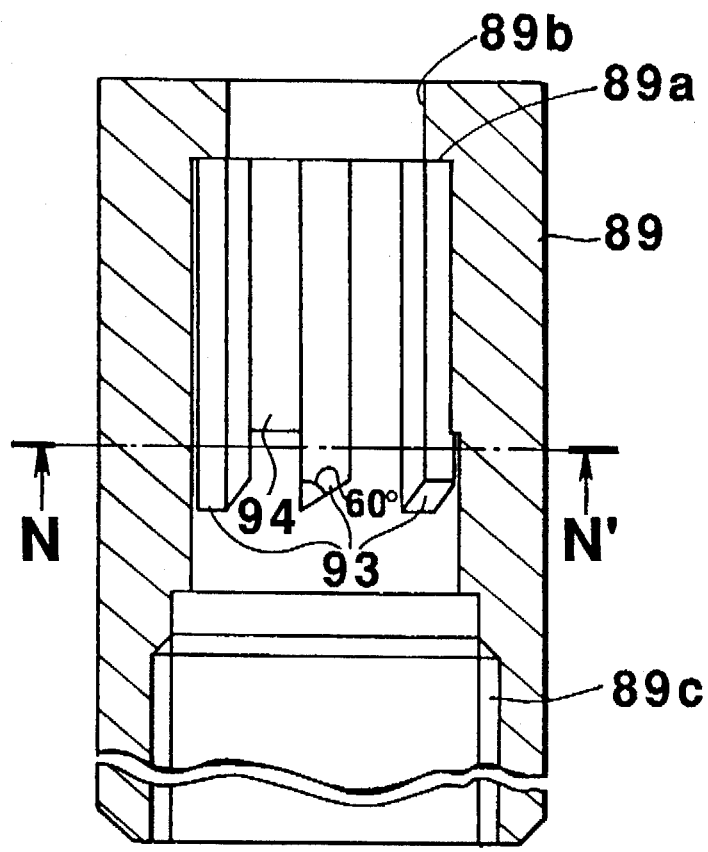
Figure 39:
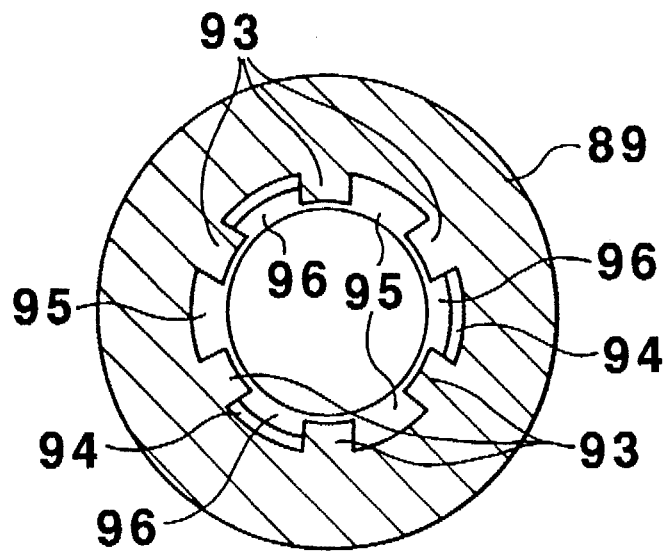

As shown in FIG. 38 and FIG. 39 which is a cross-sectioned view on line N—N' in it, the cover 89 is a hollow member in which the opposite side end of the above described bore 89b is a screw 89c screwed with the screw 75c of the above described outer tube part 75.

Here, the hollow part is provided with projections 93 arranged at intervals of 60 degrees in the inside diameter direction and diagonally cut so that the upper apex angle may be about 60 degrees and projections 94 connected with every other of the above mentioned projections 93.

Here, between the projections 93, the section in which there is no projection 94 shall be called a groove 95 and the section in which there is a projection 94 shall be called a groove 96.

In the hexapod member 91 in FIG. 36, the outside diameter including the pods 91b is so small as to enter the grooves 95 and 96.

However, in the tripod member 92 in FIG. 37, the outside diameter including the pods 92a is so large as to enter the groove 95 but not to enter the groove 96 and to catch on the projection 94.

Figure 40:
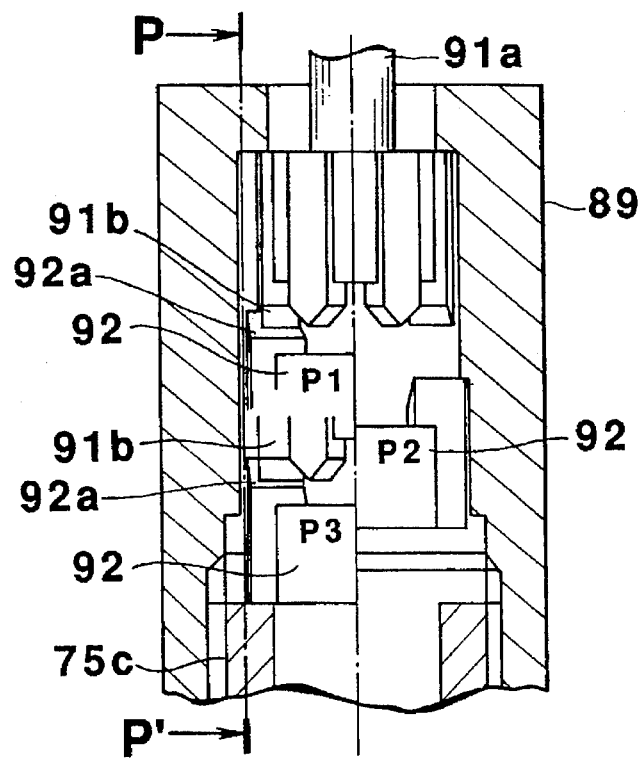
Figure 41:
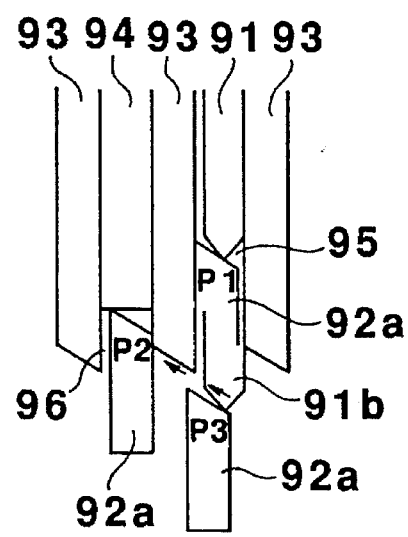

FIGS. 40 and 41 are views in which the hexapod member 91 and tripod member 92 are operated as meshed with each other. In the drawings, P1 to P3 correspond to the P1 to P3 states in FIG. 24.

In FIG. 41, when the hexapod member 91 is pushed into the lower side in the drawing, the tripod member 92 will be pushed and the three pods 92a will move to the lower side in the drawing. That is to say, they will move to P1→P3. At this time, as shown in FIG. 40, the tripod member 92 will stop against the screw 75c of the outer tube part 75.

At this time, as shown in FIG. 41, the three respective pods 92a will be out of the groove 95 which is a space enclosed with the projections 93, will be moved by the operation of the compression spring 90 first in the direction indicated by the arrow in the drawing along the slope of the pod 91b of the hexapod member 91, that is, in the left side obliquely upward direction, will then move along the slope on the projection 93, will fall down into the next groove 96, will be caught on the projection 94 and will stop. That is to say, they will move to P3→P2.

Here, in the tripod member 92, as mentioned above, the three pods 92a are provided at intervals of 120 degrees (See FIG. 37). In the cover 89, the grooves 95 are provided at intervals of 120 degrees and the grooves 96 are slipped by 60 degrees from the grooves 95 and are provided also at intervals of 120 degrees (See FIG. 39). Therefore, whenever the tripod member 92 rotates by 60 degrees, the pods 92a will enter the grooves 95–96. In FIG. 41, whenever the hexapod member 91 is pushed, the P1-P2-P1 states will be repeated.

Here, as described above, as the tripod member 92 is secured to the pressing shaft 88, in FIG. 24, whenever the pressing part 91a is pushed, the pressing shaft 88 will repeat the P1-P2-P1 states.

In the P2 state, the pressing shaft 88 presses the stopper rubber member 84. The friction force generated by this pressing is so set as to be larger enough than the force generated by the spiral spring 77 when the operating lever 62 is tilted to the maximum degree.

That is to say, in the P2 state, however the operating lever 62 may be inclined, the friction between the pressing shaft 88 and stopper rubber member 84 will be so large that the operating lever 62 will not return. The operation shall be explained in the following.

In FIG. 24, when the operating lever 62 is tilted in the P1 state of the pressing part 91a (when the pressing shaft 88 is not in contact with the stopper rubber member 84), the spiral spring 77 will be deformed and will generate a stress. After this tilting operation, when the hand is released from the operating lever 62, by the above mentioned stress, the operating lever 62 will be neutrally returned to the position in which the spiral spring is not deformed, that is, to the neutral state. In this state, the operating lever 62 will function in a neutrally returning mode.

When the pressing part 91a is pushed once and the operating lever 62 is tilted in the P2 state (where the pressing shaft 88 presses the stopper rubber member 84), in response to the tilted angle, the spiral spring 77 will be deformed and will generate a stress. When the hand is then released from the operating lever 62, by the above mentioned stress, the spiral spring 77 will tend to return the operating lever 62 to the neutral position side. However, when the pressing shaft 88 pushes the stopper rubber member 84, a friction force will be generated and will be larger than the stress generated by the spiral spring 77 and therefore the operating lever 62 will not return to the neutral position. In this state, the operating lever 62 will function in a non-neutrally returning mode.

Here, when the pressing part 91a is pushed once more, the pressing shaft 88 will stop pressing the stopper rubber member 84, both of them will be in no contact with each other and, therefore, by the stress of the spiral spring 77, the operating lever 62 will be switched to the neutrally returning mode. Thus, the two modes can be switched to each other simply by the operation of pushing the pressing part 91a.

This embodiment has the following effects.

As mentioned above, the two modes can be selected and set simply by the operation of pushing the pressing part 91a. Also, by providing the UD guide on the upper side of the switch unit, the interior of the switch unit can be made small. As it is a mechanical neutral return switching switch, no switch driving power source is required, the electricity can be economized and the safety improves. The tilting angle is so large that the fine adjustment is easy to make and the operability is high.

Figure 42A:
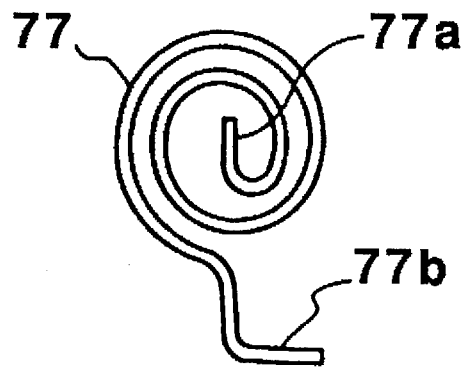
FIG. 42 is a view showing a spiral spring used in the first modification of the third embodiment.
Figure 42B:
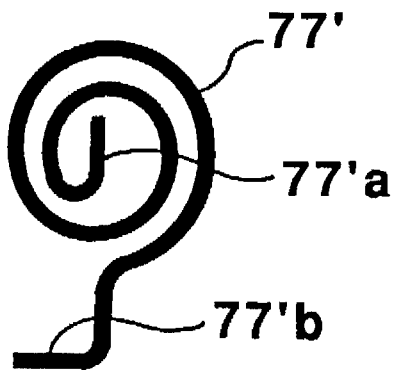
Figure 43:
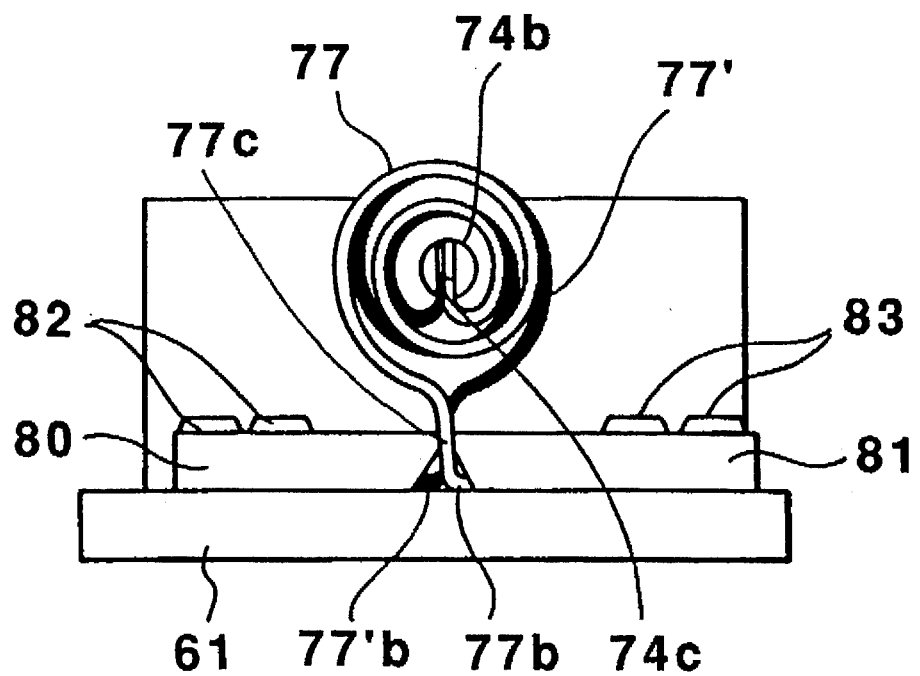
FIG. 43 is an elevation showing an RL guide as elastically fixed by the spiral spring shown in FIG. 42.

FIGS. 42 and 43 relate to the first modification of the third embodiment. FIGS. 42a and 42b show two kinds of spiral springs used in this modification. FIG. 43 shows, for example, the RL guide 74 as elastically fixed by using these spiral springs.

In the third embodiment, for example, five (See, for example, FIG. 22) of only the spiral springs 77 on one side of FIG. 42 are used but, as shown in FIG. 43, in this modification, two kinds of spiral springs 77 and 77' are used to elastically fix, for example, the RL guide 74.

The two kinds of spiral springs 77 and 77' in FIG. 42 are reverse to each other in the winding direction and therefore are energized in the directions reverse to each other. They are of substantially equal characteristics except that the winding directions are reverse to each other (the energizing directions are reverse). These spiral springs 77 and 77' have the center side ends 77a and 77'a inserted in the minus type slit 74c of the RL guide 74 and have the outside ends 77b and 77'b fixed to fixing blocks 81 and 80 respectively with screws 83 and 82.

In such case, the vertical parts 77c and 77'c will be held by the fixing blocks 81 and 80. In this modification, such groove 81a as is shown in FIG. 33 is provided not only in the block 81 but also in the block 80.

Though not shown in FIG. 43, respectively three totaling six (illustrated in FIG. 48 or 49 of the third modification) of the spiral springs 77 and 77' are fixed. Therefore, the above mentioned groove is of a width containing three spiral springs. Though not illustrated, the UD shank 70 is also fixed by the same fixing method.

Generally, the spiral spring is different in the force generated in the opening direction and in the closing direction. If the RL guide 74 and UD shank are thus symmetrically arranged and are elastically held, even if the rotary shaft of the RL guide and UD shank is rotated in either of the clockwise direction and counterclockwise direction, a uniform force will be able to be generated. Therefore, in this modification, it can be dissolved that the returning speed is different depending on the tilting direction.

The second modification of the third embodiment shall be explained with reference to FIGS. 44 to 47.

Figure 44:
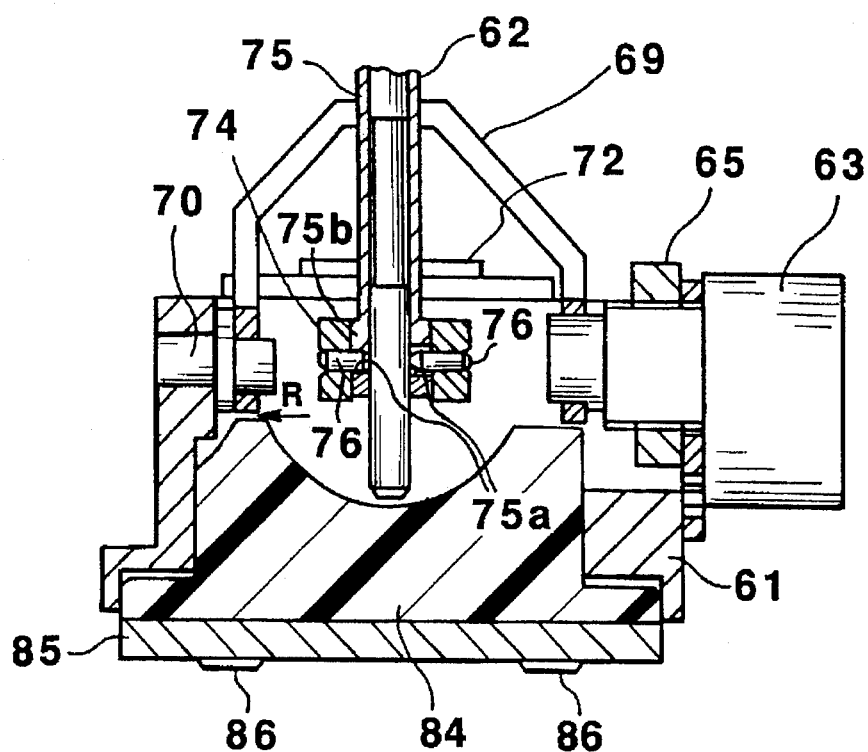
FIG. 44 is a cross-sectioned view in the RL direction in the second modification of the third embodiment of the invention.
Figure 46A:
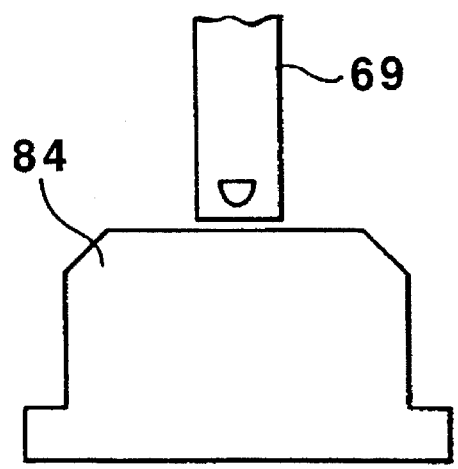
FIG. 46 is a schematic view as seen in the R direction in FIG. 44.
Figure 46B:
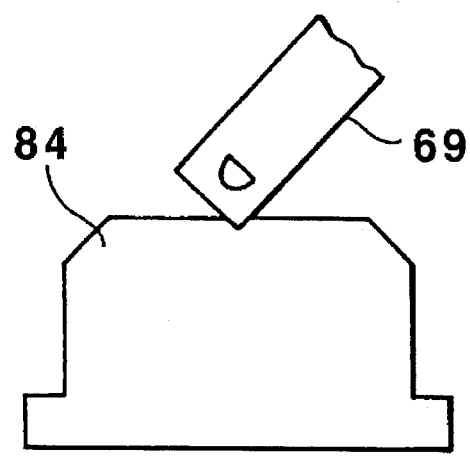

In FIG. 44 or 46a, when the operating lever 62 is tilted on the opposite side, the UD guide 69 will tilt together on the opposite side with the UD shank 70 as a rotation center, then FIG. 46a will be as shown in FIG. 46b and the UD guide 69 will abut the stopper rubber member 84 and will operate to be pushed back by the returning force of this stopper rubber member 84. Therefore, the UD guide 69 will return to the neutral position and the operating lever 62 will also return together to the neutral position.

Figure 45:
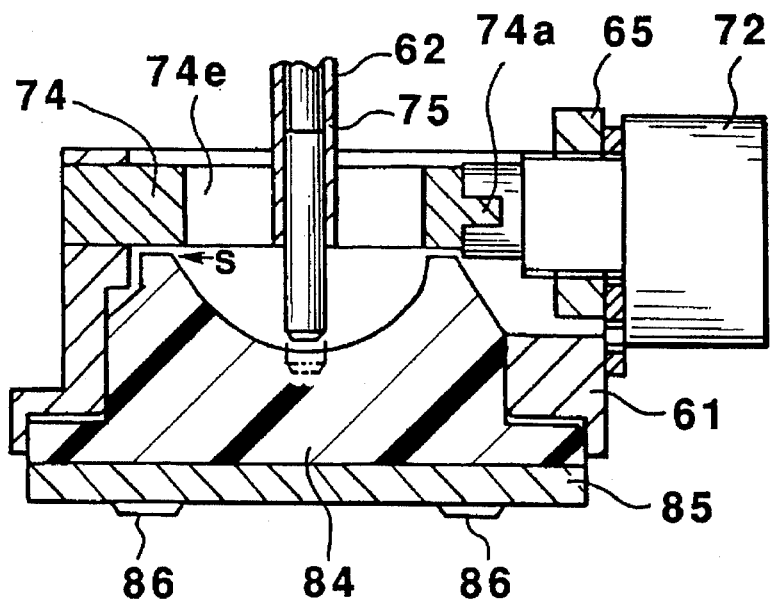
FIG. 45 is a cross-sectioned view in the UD direction in the second modification of the third embodiment of the invention.
Figure 47A:
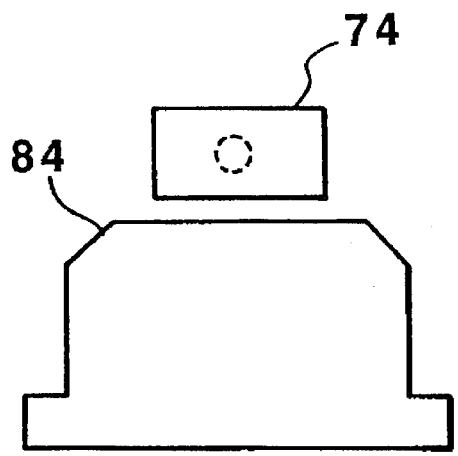
FIG. 47 is a schematic view as seen in the S direction in FIG. 45.
Figure 47B:
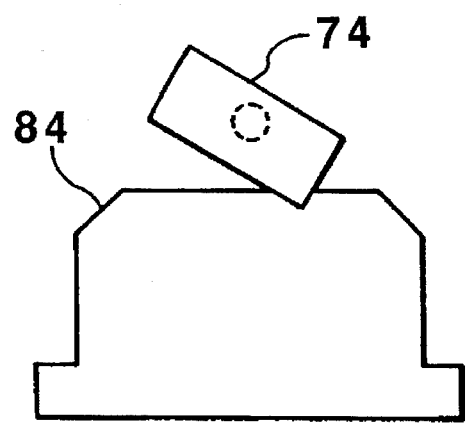

In FIG. 45 or 47a, when the operating lever 62 is inclined on the opposite side, the RL guide 74 will tilt together on the opposite side with its end as a rotation center. Then, FIG. 47a will be as shown in FIG. 47b, the RL guide 74 will abut the stopper rubber member 84 and the RL guide 74 will operate to be pushed back by the returning force of this stopper rubber member 84. Therefore, the RL guide 74 will return to the neutral position and the operating lever will also return together to the neutral position.

The effects of this modification are substantially the same as of the third embodiment.

Figure 48:
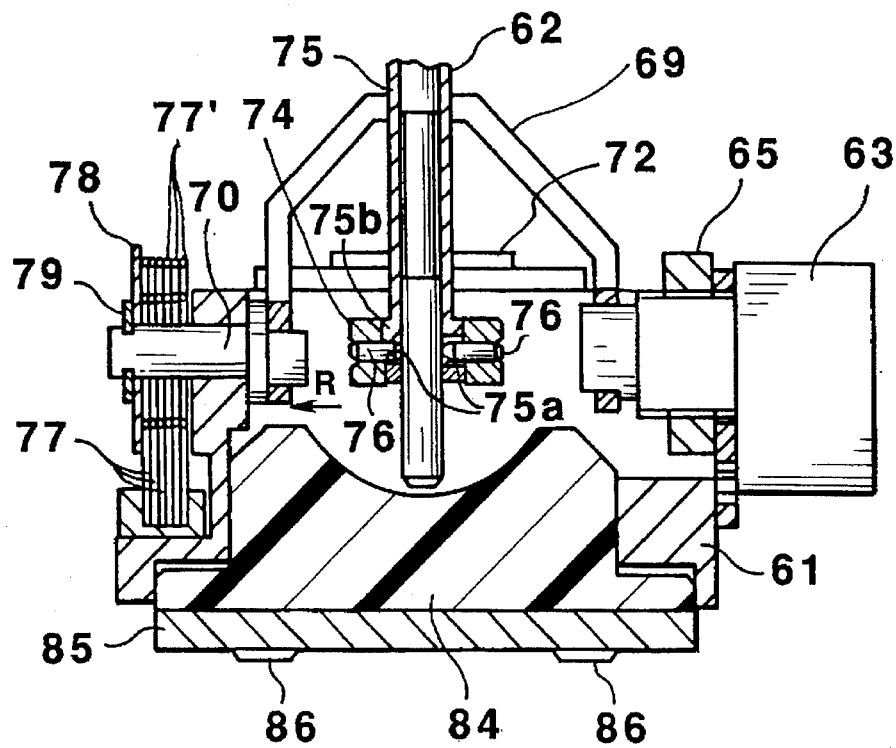
FIG. 48 is a cross-sectioned view in the RL direction in the third modification of the third embodiment of the invention.
Figure 49:
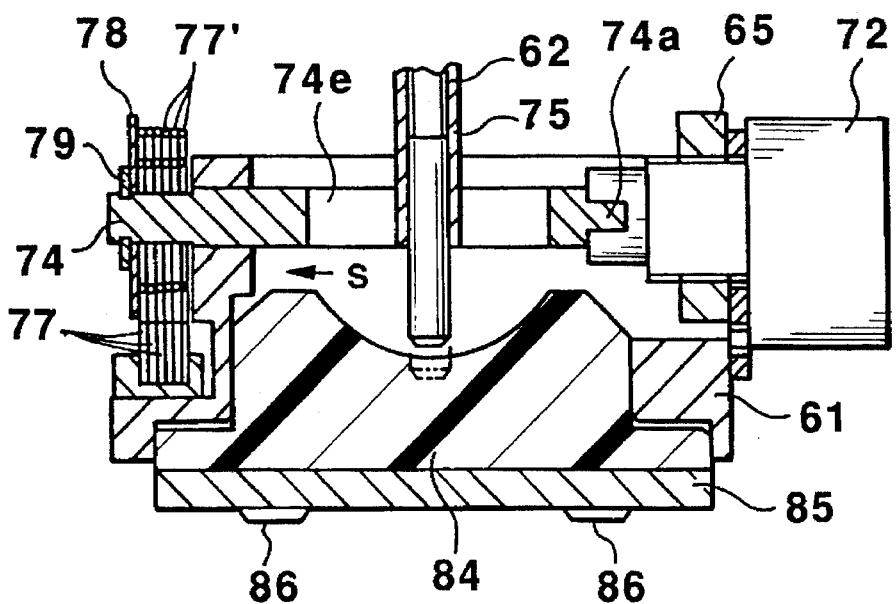
FIG. 49 is a cross-sectioned view in the RL direction in the third modification of the third embodiment of the invention.

The third modification of the third embodiment shall be explained with reference to FIGS. 48 and 49 in the following. This modification is a combination of the third embodiment and the second modification. That is to say, the operating lever is returned to the neutral position by the elastic force of the spiral spring and stopper rubber member. In case the tilting angle of the operating lever is small (in case the operating lever is a little tilted from the state in FIG. 48 or 49), when the UD guide 69 or RL guide 74 does not abut the stopper rubber member, it will be returned by the elastic force of the spiral spring. In case the tilting angle of the operating lever is large, the RL guide 74 or the like will abut the stopper rubber member and will be returned by the elastic force of the stopper rubber member and spiral spring.

The fourth modification of the third embodiment shall be explained in the following. In this modification, in case the inside ends 77a and 77a' of the spiral springs 77 and 77', for example, in FIG. 42 are to be fixed, without making the rotation centers coincide with each other, the ends will be slipped little by little from each other and will be fixed in the slit 74c in the RL guide 74 so that the springs may be energized to be kept in the position even in the state of the neutral position and no play may be generated near the neutral position (even if they are slightly tilted, no force returning them to the neutral position will be generated).

The fifth modification of the third embodiment shall be explained in the following. In this this modification, the inside ends 77a and 77a' of the spiral springs 77 and 77'. for example, in FIG. 42 are deformed so as to be wound in and are fixed in the slit 74c or the like in the RL guide 74 so that the springs may be energized in the position and no play may be generated.

The fourth embodiment of the present invention shall be explained with reference to FIGS. 50 to 54.

In this embodiment, the SMA compression spring compressed between the UD guide and RL guide in the second embodiment is compressed between the operating lever and case, the others are the same as in the second embodiment and the same components shall bear the same reference numerals and shall not be explained here.

Figure 50:
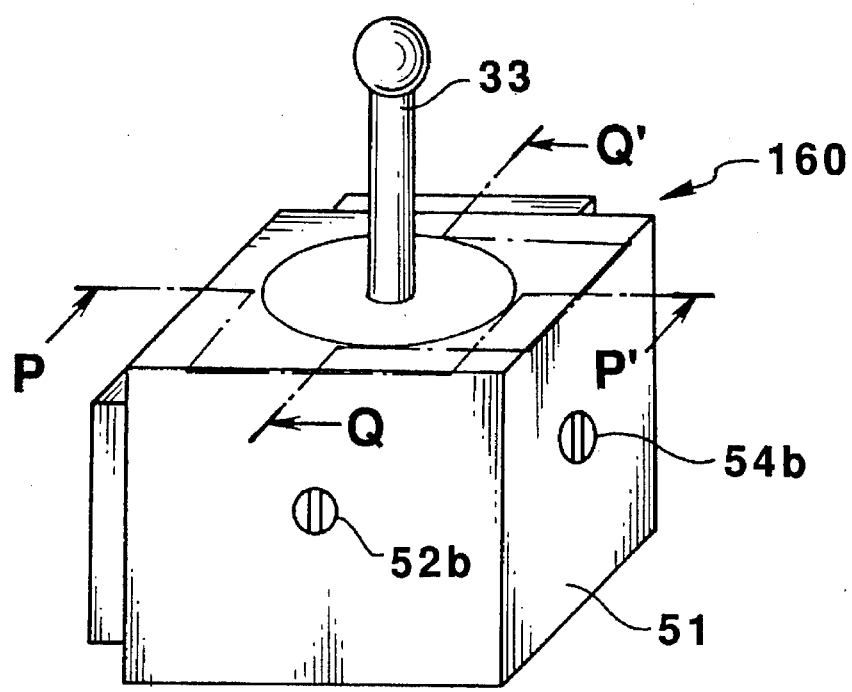
FIGS. 50 to 54 relate to the fourth embodiment of the present invention, FIG. 50 being a perspective view showing a curvature switch in the fourth embodiment of the present invention.

The joy stick 160 shown in FIG. 50 comprises a case 51 and an operating lever 33.

Figure 51:
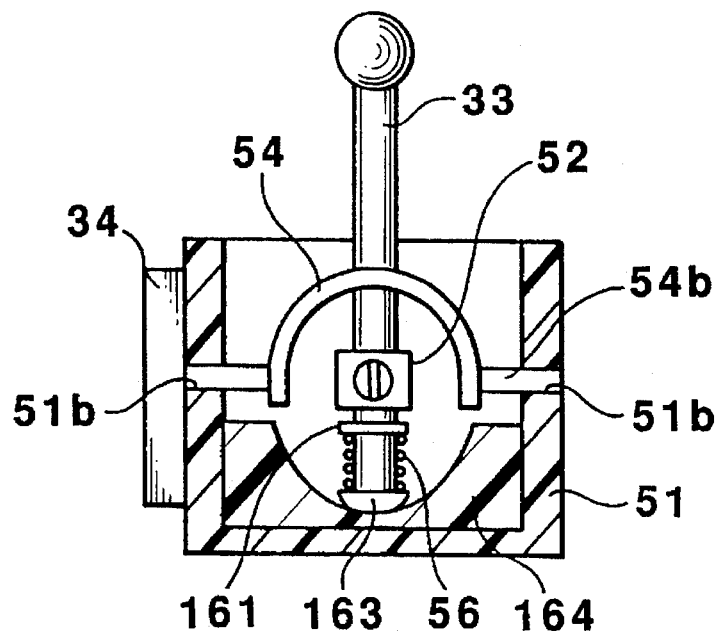
Figure 52:
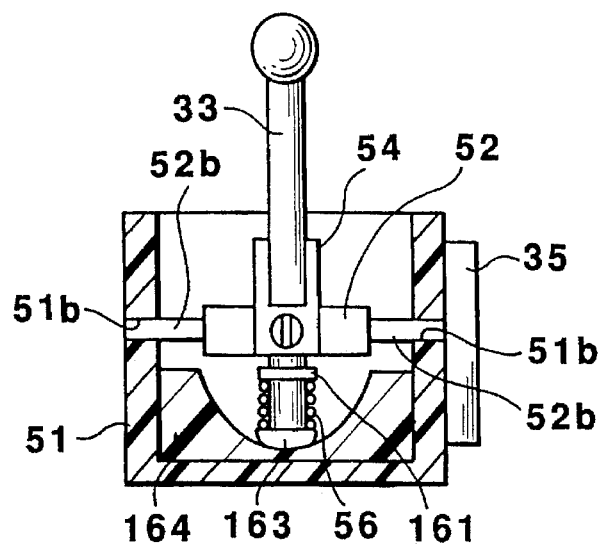

FIG. 51 is a cross-sectioned view On line P—P' in FIG. 50. FIG. 52 is a cross-sectioned view on line Q—Q' in FIG. 50.

As understood from these drawings, within the case 51, the UD guide 54 explained in the second embodiment is fitted as directed reversely and the RL guide 52 is provided in the same direction as in the second embodiment. Below the RL guide 52, a flange part 161 is fixed to the operating lever 33 by such means as pressing in. Below this flange part 161, holding the SMA compression spring 56 already described in the second embodiment, the later described moving member 163 is provided. Below the moving member 163, a cam member 164 having a cam curved surface is fixed to the case 51 by a means after bonding.

Figure 53:
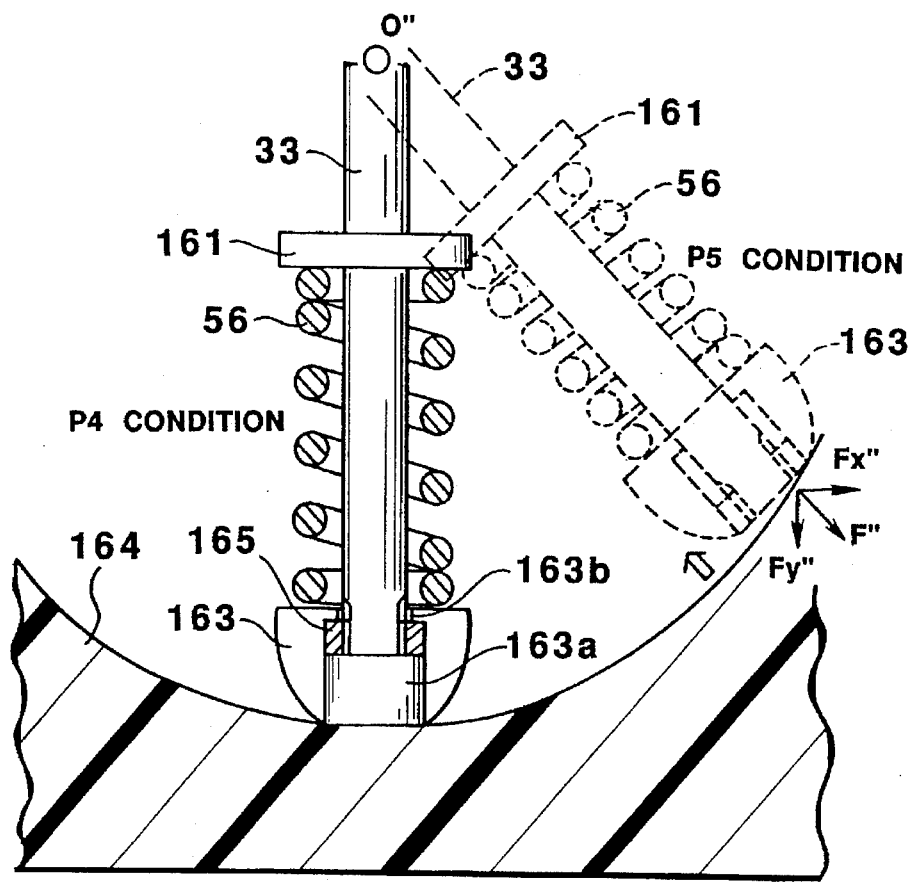
Figure 54:
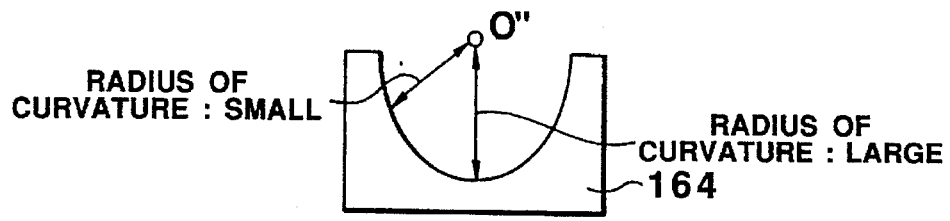

FIG. 53 is a view showing the cam ember 164 and moving member 163 as related with each other.

As shown in FIG. 53, the cam member 164 has a curved surface in which the radius of curvature from the rotation center O" of the operating lever 33 is large in the center but is smaller toward both ends. This curved surface is the same in all the U, D, R and L directions.

Returning to FIG. 53, in the P4 state in the neutral state, the flange part 161 is fixed to the operating lever and, below it, the SMA compression spring 56 is inserted through the operating lever 33. Further, below it is provided the moving member 163 having a hemispherical curved surface on the cam member 164 side and having a counter groove 163a and a through bore 163b smaller than it.

When the operating lever 33 is passed through the through bore 63 and a nut 166 is fastened to a screw part 165 provided on the operating lever 33 within the counter groove 163a, the moving member 163 will be movable upward in the drawing with respect to the operating lever 33 and will not be removed from the operating lever 33.

When the operating lever 33 is tilted, the P5 state will be made, then the radius of curvature of the cam member 164 will become smaller and therefore the moving member 163 will move in the direction indicated by the arrow.

Here, as the flange part 161 is fixed to the operating lever 33, the distance from the rotation center O" will not vary. That is to say, as only the moving member 163 approaches the rotation center O", the compression spring 56 held between the flange part 161 and moving member 163 will be compressed and deformed.

By the way, as described in the second embodiment, a power source not illustrated is connected to both ends of the SMA compression spring 56 so that, whenever the upper head part 33a of the operating lever 33 is pushed, the circuit formation will repeat the electrification, non-electrification and electrification. The operation shall be explained in the following.

In FIG. 53, for example, when the compression spring is not electrified, if the operating lever 33 is inclined to make the P4 state→P5 state, by the cam member 164, the moving member 163 will be moved in the direction indicated by the arrow in the drawing and the compression spring 56 will be compressed and deformed. Here, as described in the second embodiment, when the SMA is not electrified, the transverse elastic modulus G will become small and thereby the compression spring 56 will become small in the stress generated by the deformation. Therefore, when not electrified, even if the compression spring 56 is deformed, it will remain deformed and will not return to the original state.

Here, when the compression spring 56 is electrified and heated, the transverse elastic modulus G will become large and therefore the generated stress will also become large. Here, the compression spring 56 will tend to push back the curved surface of the cam member 164, this force F" will be analyzed into Fx" and Fy" and the moving member 163 will be returned to the P4 state by Fy". Thereby, the operating lever will return to the neutral position.

Figure 55:
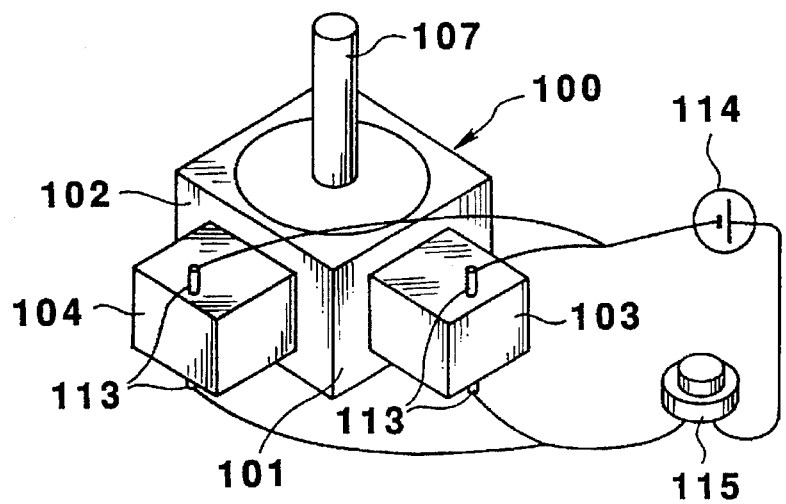

The curvature operating switch in the fifth embodiment of the present invention shall be explained in the following. In FIG. 55, the joy stick 100 is provided with a neutral returning mechanism not illustrated. Projections 103 and 104 are provided on two side surfaces 101 and 102 of this joy stick 100.

Figure 56:
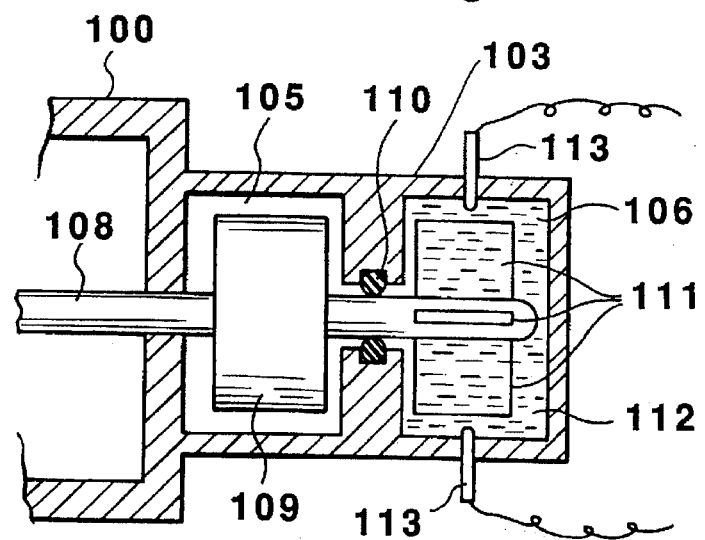

As shown in FIG. 56, the projection 103 comprises a potentiometer chamber 105 and a brake chamber 106. An O-ring 110 is provided between the potentiometer chamber 105 and brake chamber 106 to seal both chambers.

Within the potentiometer chamber 105, a rotary shaft 108 rotated by moving a stick 107 is provided to pass through the potentiometer 109 and the rotation angle of this rotary shaft 108 is to be detected by the potentiometer 109.

The rotary shaft 108 passing through the potentiometer 109 reaches the interior of the above mentioned brake chamber 106 and has blades 111 fixed near the end. In FIG. 56, four blades are fixed at intervals of 90 degrees. At least one blade may be fixed.

The brake chamber 106 is filled with a solvent 112 (a so-called ER fluid) mixed with fine grains of 1 to 100 μm. An electrode 113 is provided in this brake chamber 106 so as to be exposed within the chamber. The electrode 113 is electrically connected with a power source 114 and switch 115 through lead wires.

When the solvent 112 is ionized and not aligned, the rotary shaft 108 provided with the blades 111 contained within the brake chamber 106 will only agitate the solvent 112 within the brake chamber 106 and will not obstruct the rotation.

The operation of this embodiment shall be explained in the following.

When the stick 107 of the joy stick 100 is inclined, the rotary shaft 108 will rotate by the inclination angle of the stick 107 and this rotation will be detected by the potentiometer 109. In this case, as the solvent 112 is ionized and not aligned, the rotary shaft 108 provided with the blades 111 contained within the brake chamber 106 will only agitate the solvent 112 within the brake chamber 106 and will not obstruct the rotation.

The value of the rotation angle detected here is processed by a controlling system not illustrated and curves, for example, the curvature section of the endoscope. Here, when the hand is released from the stick 107, the stick 107 will be returned to the neutral state by a neutral returning mechanism not illustrated.

On the other hand, in case the stick 107 is wanted to be fixed in any position, the switch 115 will be switched on.

Then, the electrode 113 will conduct with the power source 114. A +(plus) charge will be generated in one electrode 113 and a −(minus) charge will be generated in the other electrode 113.

Therefore, as the fine grains in the solvent 112 with which the brake chamber 106 is filled are ionized, as shown in FIG. 58b, the fine grains will be attracted to the charges of the electrodes 113 and will be combined and nearly aligned between the pair of electrodes 113. As a result, the viscosity of the solvent 112 will rise, the blades 111 will be no longer able to rotate due to the resistance and the stick 107 will be fixed in any position.

Further, in order to return the stick 107 to the neutral state from this state, the switch 115 is switched off. Thereby, as shown in FIG. 58a, the ionized fine grains in the solvent 112 will be no longer combined and the viscosity of the solvent 112 will reduce.

As a result, the blades 111 will be able to rotate and the stick 107 will be returned to the neutral state by the neutral returning mechanism. By the way, as the brake chamber 106 and the potentiometer chamber 105 are sealed with the O-ring 110 between them, even if the rotary shaft 108 rotates, the solvent within the brake chamber 106 will not leak into the potentiometer chamber 105.

By the way, the brake chamber 106 may be provided with a solvent replacing drain hole. The switch 115 may be built-in in the stick 107. The fine grains in the solvent will not easily precipitate. Even if they precipitate, they will be soon made to be uniformly present in the solvent by the agitation of the blades.

This embodiment has a merit that it can be made smaller than a mechanical or electromagnetic clutch.

The endoscope apparatus of the sixth embodiment provided with an automatic curving means automatically curving the insertable section shall be explained in the following.

Figure 59:
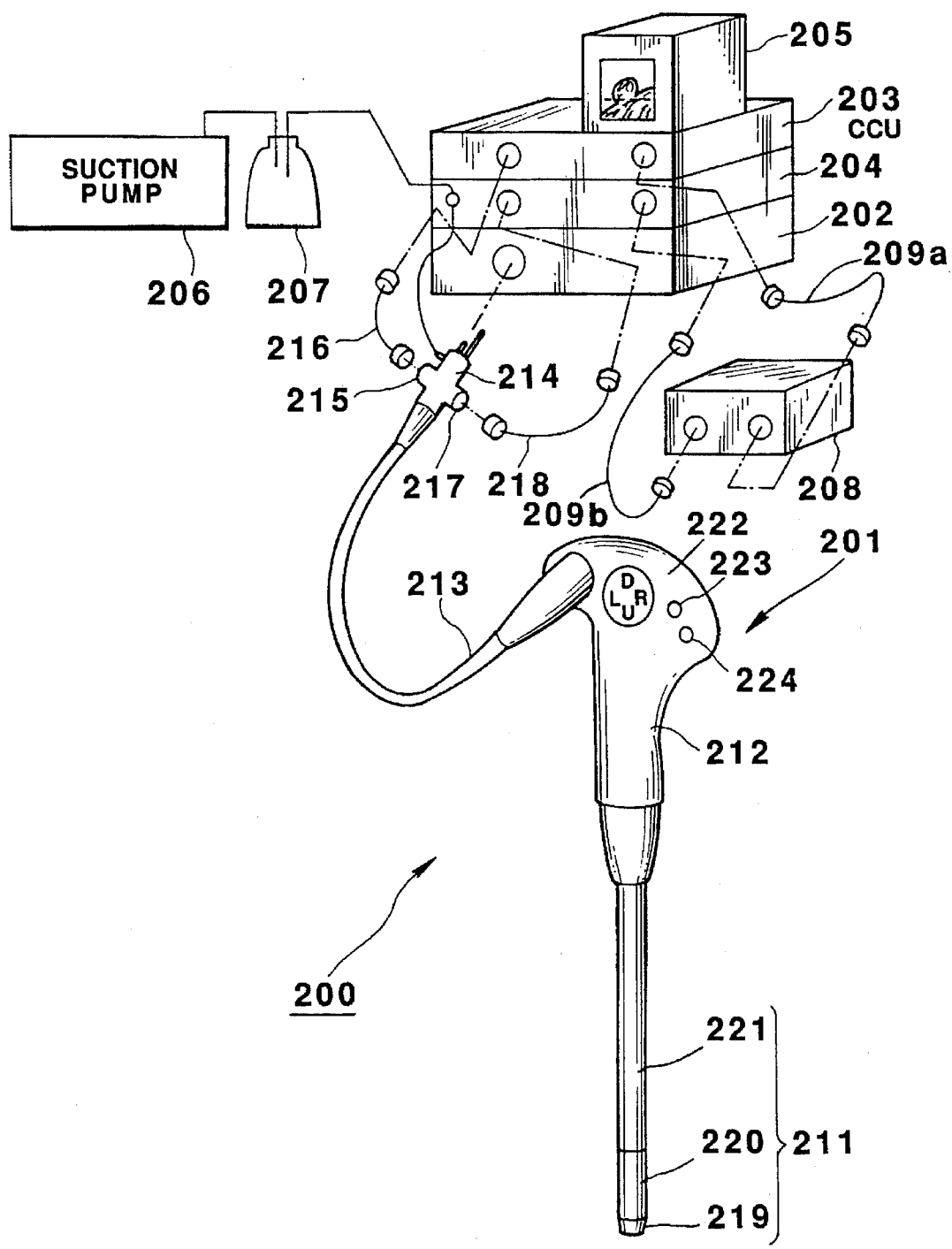
FIGS. 59 to 65 relate to the sixth embodiment of the present invention, FIG. 59 being a block diagram showing a schematic formation of a curvature operation controlling means.

As shown in FIG. 59, an endoscope apparatus 200 comprises an endoscope 201 for observing a position to be inspected, a light source apparatus 202 connected to this endoscope 201 and feeding an illuminating light, a camera controlling unit (mentioned as a CCU hereinafter) 203 for processing an image signal obtained in the endoscope 201 and a motor & fluid controlling apparatus 204 for controlling a curving motor and making such fluid controls as feeding air/feeding water and suction.

A monitor 205 is connected to the CCU 203, transmits and receives signals to and from such solid state imaging device as a CCD not illustrated provided at the tip of the endoscope 201, processes image signals imaged by the solid state imaging device and displays endoscope observed images. A suction pump 206 and bottle 207 are connected to the motor & fluid controlling apparatus 204 so that feeding air/feeding water and suction may be made from a channel not illustrated at the tip of the endoscope 201.

Further, a tube cavity detecting apparatus 208 to be used in the case of an automatic curvature is connected to the CCU 203 and motor & fluid controlling apparatus 204 respectively through cables 209a and 209b. By this tube cavity detecting apparatus 208, the center of the tube cavity is detected from the video output signal from the CCU 202, curvature motors 229 and 230 (See FIG. 60) are controlled by the motor & fluid controlling apparatus 204 on the basis of the detected result and the tip of the insertable section is directed to the center of the tube cavity.

The endoscope 201 comprises an elongate insertable section 211, an operating section 212 which is also a holding part connected to the rear end side of the insertable section 211 and a universal cord 213 extended from the side of the operating section. This universal cord 213 is connected to the light source apparatus 202 through a connector 214 provided at the end of this universal cord 213 so that the illuminating light may be led to a light guide not illustrated within the universal cord 213.

Further, the universal cord 213 is connected respectively to the CCU 203 through a cable 216 connected to a mouthpiece 215 of the connector 214 and to the motor & fluid controlling apparatus 204 through a cable 218 connected to a mouthpiece 217.

The insertable section 211 of the endoscope 201 is formed by connecting, from the tip side, a rigid tip section 219, a curvable curvature section 220 and a flexible tube section 221 having a flexibility. The operating section 212 is connected to the rear end side of the flexible tube section 221 and is provided with a curving switch 222 as a first driving instructing means instructing the curving operation of the curvature section 220, a freezing switch freezing endoscope images and a releasing switch releasing endoscope images. By the way, though not illustrated, an air feeding switch, water feeding switch and sucking switch are also provided.

Figure 60:
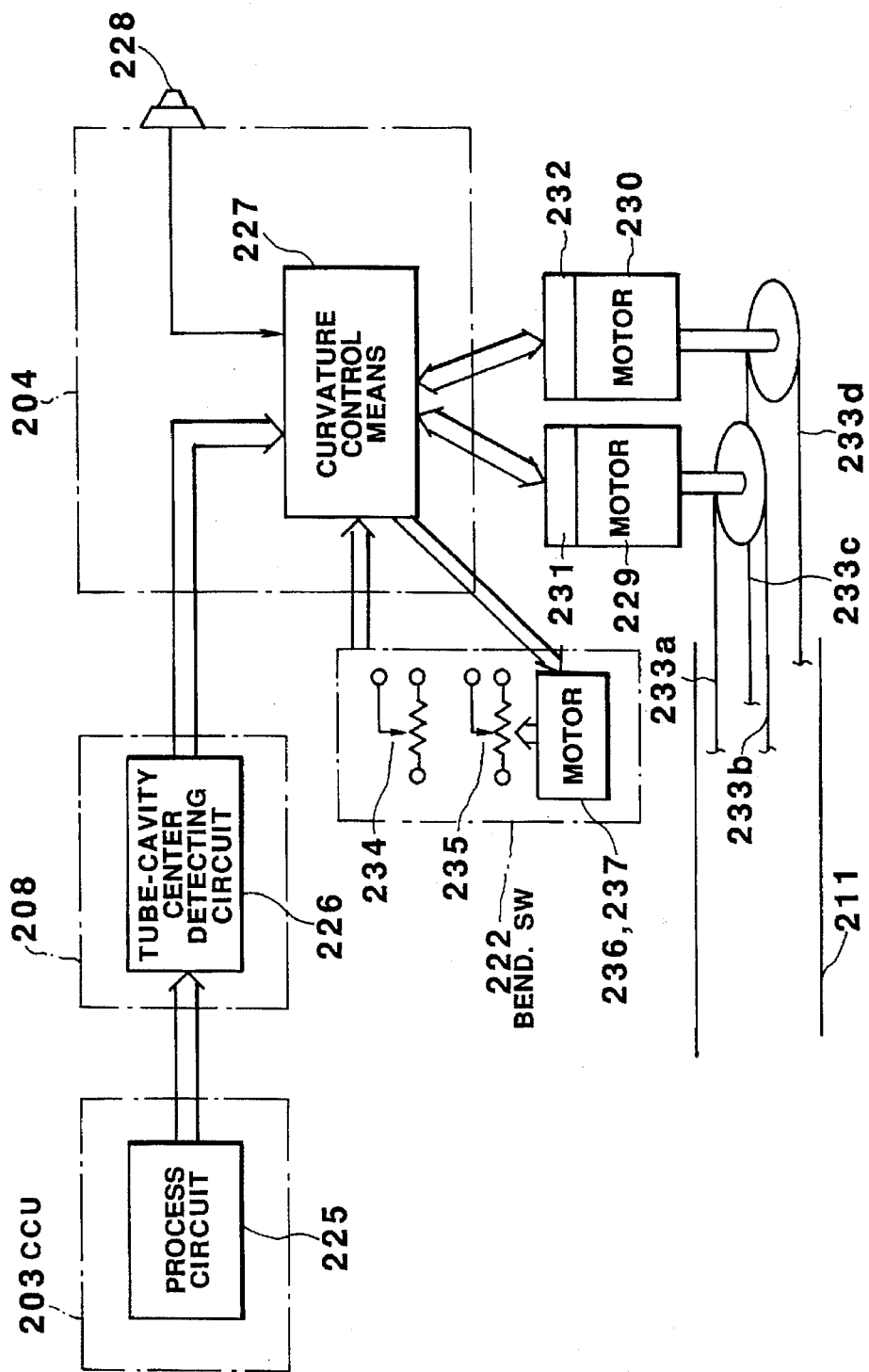

FIG. 60 shows a schematic formation of a curving operation controlling means controlling the curving operation of the curvature section 220 and the operating part of the curving switch 222.

The video output signal processed by the processing circuit 225 within the CCU 203 is input into the tube cavity center detecting circuit 226 as a driving instructing means in the case of the automatic curvature provided within the tube cavity detecting apparatus 208 and here the center of the tube cavity is detected by detecting the dark part from the above mentioned video output signal.

The output signal showing the tube cavity center from the tube cavity center detecting circuit 226 is input into the curvature controlling means 227 as a driving controlling means within the motor & fluid controlling apparatus 204.

A switching switch 228 switching the automatic curving and manual curving operation is connected to the curving controlling means 227 so that, when this switch 228 is switched to the automatic curving mode, the curving of the curvature section 220 may be controlled so that the tip section 219 may be directed to the tube cavity center on the basis of the output signal of the above mentioned tube cavity center detecting circuit 226.

The curving controlling means 227 is connected to curving motors 229 and 230 generating curving driving forces and to encoders 231 and 232 fitted respectively to the rotary shafts of these curving motors 229 and 230, outputs to the curving motors 229 and 230 the curving instructing signals produced on the basis of the output signals of the tube cavity center detecting circuit 226 to control the curving driving, takes in the output signals from the encoders 231 and 232 to detect the curvature angle of the curvature section 220 and curves the detected curvature angle until it coincides with the curving instructing value.

Pulleys are fitted to the rotary shafts of the curving motors 229 and 230 and four curving wires 233a, 233b, 233c and 233d fixed at one end to the tip side of the curvature section 220 are wound around the pulleys.

When the respectively paired curving wires 233a and 233b and 233c and 233d are respectively advanced and retreated (pulled/relaxed), the curvature section 220 will be curved in four upward, downward, rightward and leftward directions.

The curving switch 222 is connected to the curving controlling means 227 so that, when the switching switch 228 is switched to the manual mode, the curving will be controlled in compliance with the instruction of the curving switch 222. The curving switch 222 is formed of a joy stick type switch and is provided with variable resistors 234 and 235 in the respective vertical and horizontal directions.

The curving controlling means 227 controls the rotations of the curving motors 229 and 230 so that the resistance values of these variable resistors 234 and 235 and the outputs of the above mentioned encoders 231 and 232 may satisfy a predetermined function and thereby the curvature section 220 may curve by a curvature angle corresponding to the instruction of the curving switch 222. The above mentioned predetermined function is such function in which the tilting angle of the operating lever of the curving switch 222 and the curvature angle of the curvature section 220 are proportional to each other.

Further, the curving switch 222 is provided with joy stick motors 236 and 237 driving the operating lever of the curving switch 222. The motors 236 and 237 are connected to the curving controlling means 227. The operating lever is driven so that, when the switching switch 228 is switched to the automatic curving mode, the instructing value of the curving switch 222 may correspond to the curvature angle of the actual curvature section 220.

That is to say, when the automatic curving mode is switched to the manual mode, unless the curving instructing value set in the automatic curving mode just before switching and the instructing value by the inclination of the operating lever coincide with each other, the curvature section 220 will be quickly curved so as to coincide with the instructing value by the inclination of the operating lever after switching. However, in this embodiment, the inclination of the operating lever is maintained so as to coincide with the curving instructing value in the automatic curving mode so that the curvature section 220 may not be quickly curved at the time of switching.

Here, the detailed formation of the curving switch 222 shall be explained with reference to FIGS. 61 to 64.

Figure 61:
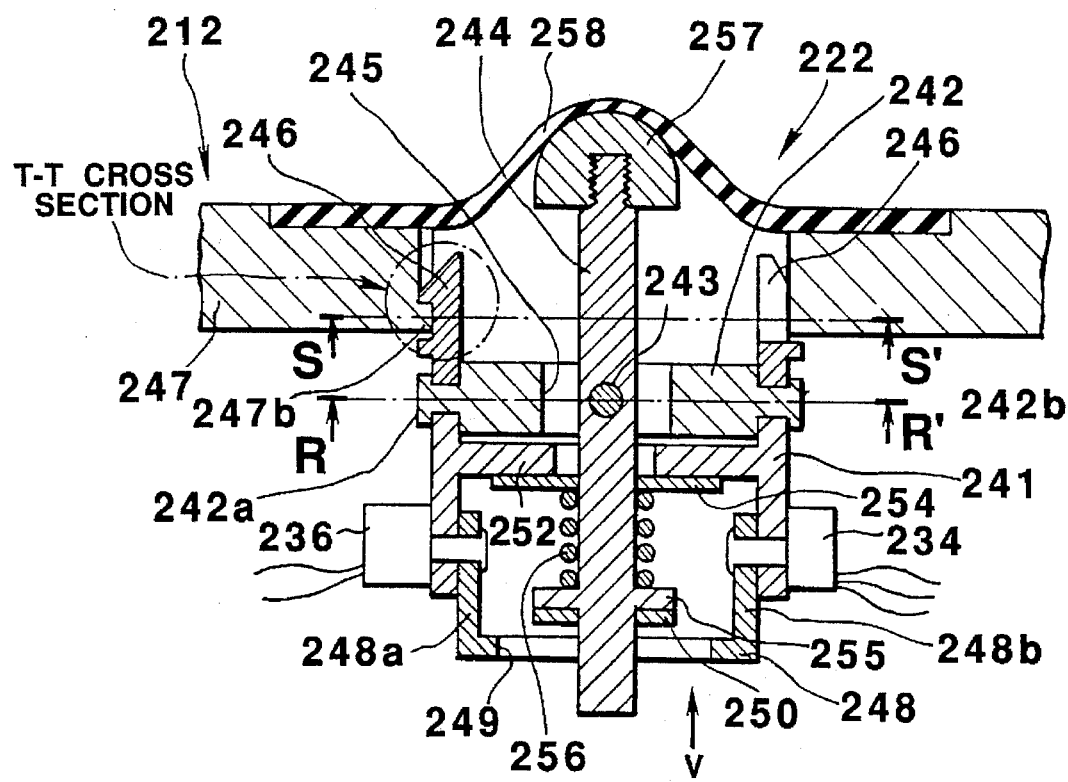
Figure 62:
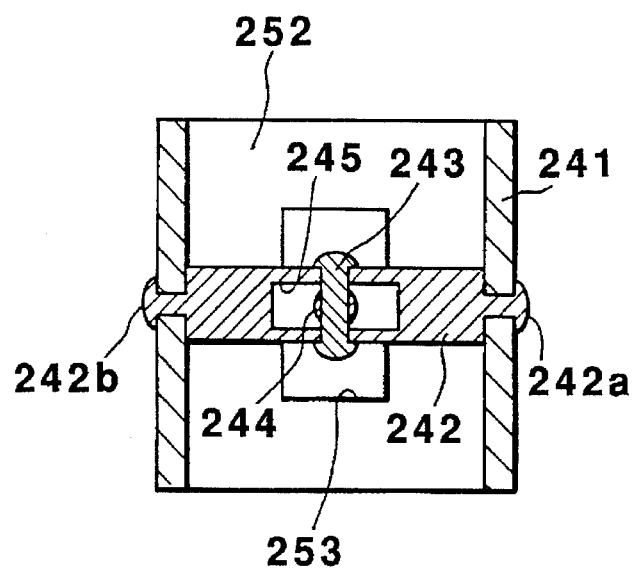

As shown in FIG. 61, in the casing 241 of the curving switch 222, shafts 242 and 243 intersect at right angles with each other and are respectively rotatably provided. The shaft 242 is passed through a bore provided in the casing 241 and is crushed at both ends 242a and 242b so as to be like rivets and is rotatably supported by the side surfaces of the casing 241. As shown in FIG. 62, the shaft 243 is passed through the shaft 242, is crushed at both ends like rivets and is rotatably supported with respect to the shaft 242.

The operating lever 244 is secured to this shaft 243 so that this shaft 243 may pass through and intersect at right angles with the operating lever 244 (the operating lever 244 intersect at right angles also with the shaft 242). The part in which the shaft 243 is pivoted in the shaft 242 is provided with a hollow part 245 corresponding to (defining) the operating range of the operating lever 244. The operating lever 244 passes through the hollow part 245 and is movable only in two directions in the length range of the hollow part 245.

That is to say, when the operating lever 244 is inclined in the lengthwise direction of the hollow part 245, it will rotate with the shaft 243 as a center but, when the operating lever 244 is inclined in the direction intersecting at right angles with the lengthwise direction, it will rotate with the shaft 242 as a center.

Figure 63:
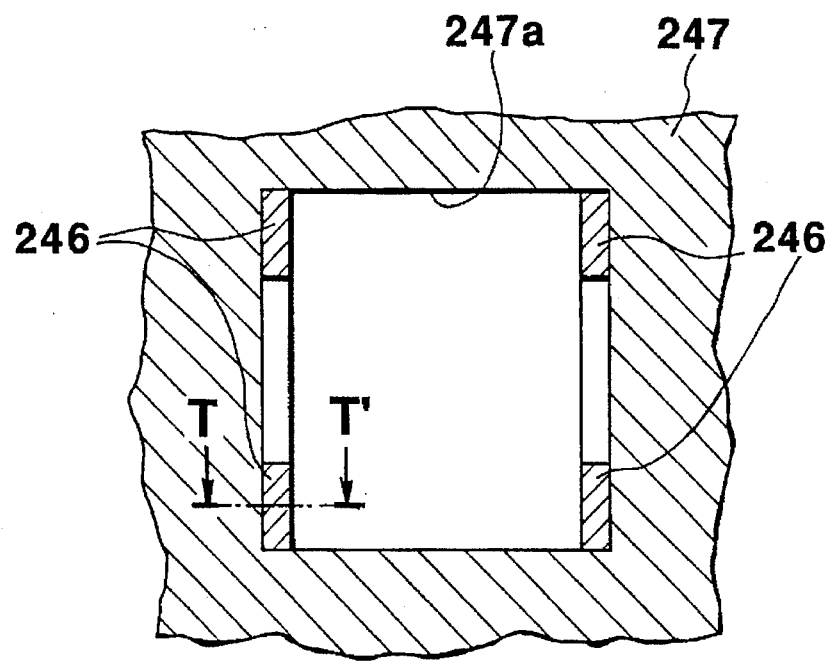

In the upper part of the above mentioned casing 241, as shown by the one-point chain circle in FIG. 61 and by FIG. 63, four arms 246 are extended upward and the casing 247 of the operating part 212 is provided with a square incision 247a. When the flange parts 247b provided on the two opposed sides of the incision 247a are over-ridden by the elasticity of the arms 246 and the pawls of the arms 246 engage with the flange parts 247b, the casing 241 of the curving switch 222 will be fixed to the casing 247 of the operating part 212.

Below the casing 241, a U-shaped rotor 248 is rotatably pivoted to the casing 241. The arms 248a and 248b at both ends of the rotor 248 are provided respectively with bores. The rotary shaft of the joy stick motor 236 is passed through the arm 248a through the casing 241 and is secured to the rotor 248 with a bonding agent or the like. The resistance setting shaft of the variable resistor 234 is passed through the arm 248b through the casing 241 and is secured to the rotor 248 with a bonding agent or the like.

By the way, the bodies of the joy stick motor 236 and variable resistor 234 are secured to the side of the casing 241. That is to say, when the rotor 248 rotates with respect to the casing 241, the resistance setting shaft of the variable resistor 234 will rotate, the resistance value will vary and, when the joy stick motor 236 rotates, the rotor 248 will rotate.

Figure 64:
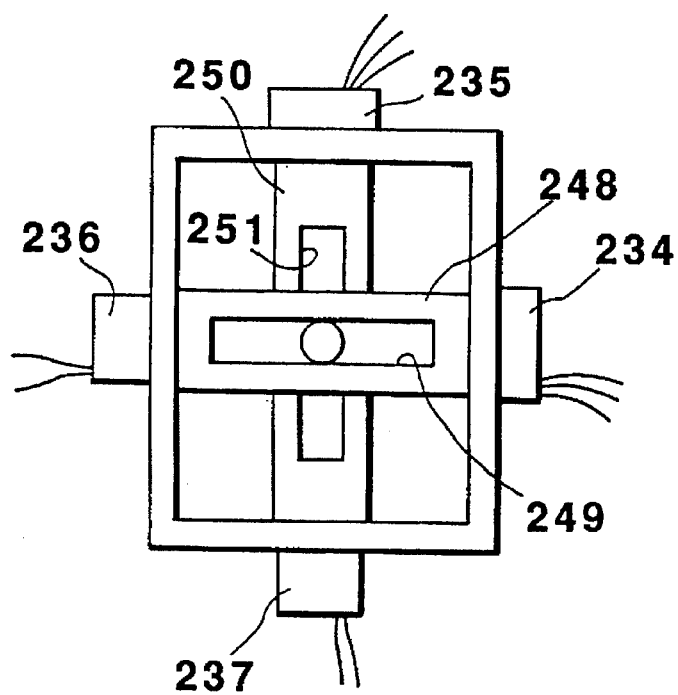

The barrel of the rotor 248 is provided with a slot 249. The tip of the operating lever 244 is inserted and is engaged with the slot 249. Above the rotor 248, as shown in FIGS. 61 and 64, a rotor 250 U-shaped the same as the rotor 248 is provided to intersect at right angles with the rotor 248 and is rotatably pivoted to the casing 241 the same as the rotor 248.

The rotor 250 is provided with a slot 251 the same as the rotor 248. The tip of the operating lever 244 is inserted and engaged with the slot. The same as in the rotor 248, the rotary shaft of the joy stick motor 237 and the resistance setting shaft of the variable resistor 235 are respectively secured to the arms at both ends of the rotor 250. The bodies of the joy stick motor 237 and variable resistors 235 are secured to the casing 241.

That is to say, when the operating lever 244 is inclined with the shafts 242 and 243 as centers, the rotors 248 and 250 will rotate and the resistance values of the variable resistors will accordingly vary. When the joy stick motors 236 and 237 are rotated and driven, the rotors 248 and 250 will rotate and the operating lever 244 will incline.

The casing 241 is provided with a partition wall 252 projecting inside in the lower parts of the shafts 242 and 243. In the central part of the partition wall 252, as shown in FIG. 62, there is provided a square hole 253 through which the operating lever 244 is inserted. This square hole defines the operating range of the operating lever 244.

By the way, when the size and shape of the square hole are varied, the operating range of the operating lever 244 will be able to be varied. The operating lever 244 passes through the lower side of the partition wall 252. A plate 254 slidable in the axial direction of the operating lever 244 is arranged so as to be in contact with the partition wall. A flange part 255 is provided in the upper part of the rotor 250 of the operating lever 244. A compression spring 256 energized in the vertical direction is arranged between the plate 254 and flange part 255.

When the operating lever 244 is not driven by the joy stick motors 236 and 237, the operating lever 244 will be returned to the central position by the resiliency of this compression spring 256.

A grip 257 is screwed and fitted to the head part of the operating lever 244. Further, a rubber cover 258 is provided to water-tightly cover the top of the grip 257 to the casing 247 of the operating section 212 to prevent the operating section 212 from water.

The operation of this embodiment shall be explained in the following.

The insertable section 211 of the endoscope 201 is inserted into such position to be inspected as within a body cavity and the curving switch 222 is operated to curve the curvature section 220 to observe the position to be inspected. Here, in case the switching switch 228 is set in the manual mode, when the operating lever 244 of the curving switch 222 is operated to be rotated and inclined with the shafts 242 and 243 as rotary shafts, the rotors 248 and 250 will rotate and the resistance values of the variable resistors 34 and 35 will vary.

The resistance values will be input into the curving controlling means 227 which will rotate the curving motors 229 and 230 in response to the input resistance values and will control the drive of the curving motors 229 and 230 so that the outputs of the encoders 231 and 232 and the above mentioned resistance values may fill the predetermined function. Thereby, the curvature section 220 will curve to be of a curvature angle proportional to the tilting angle of the operating lever 244 of the curving switch 222.

On the other hand, when the switching switch 228 is set in the automatic curving mode, the tube cavity center detecting circuit 226 will detect the darkest part from the video output signal of the processing circuit 225, will judge it as the tube cavity center and will output a signal showing the center position to the curving controlling means 227. The curving controlling means 227 will control the curving motors 229 and 230 in compliance with the tube cavity center direction instruction from the tube cavity center detecting circuit 226 and will curve the curvature section in the direction of the tube cavity center.

Therefore, when the insertable section 211 is inserted into a body cavity or hollow, if the switching switch 228 is switched to the automatic curving mode and the curvature section 220 is set in the controlling state of curving in the direction of the tube cavity center, the insertable section 211 will be able to be easily inserted.

In the case of this automatic curving mode, the curving controlling means 27 will control the curving motors 229 and 230, will control the joy stick motors 236 and 237 so that the inclination of the operating lever 244 of the curving switch 222 may be maintained so as to be of the curving instructing value in the direction indicating the tube cavity center direction, that is to say, so that the angle curving the curvature section 220 and the tilting angle of the operating lever 244 may be proportional to each other and will rotate the rotors 248 and 250.

Thereby, the operating lever 244 will be driven to correspond to the curving angle of the curvature section 220. In the control at this time, the joy stick motors 236 and 237 may be driven and controlled so that the signal showing the tube cavity center direction and the resistance values of the variable resistors 234 and 235 may fill the predetermined function.

Figure 65:
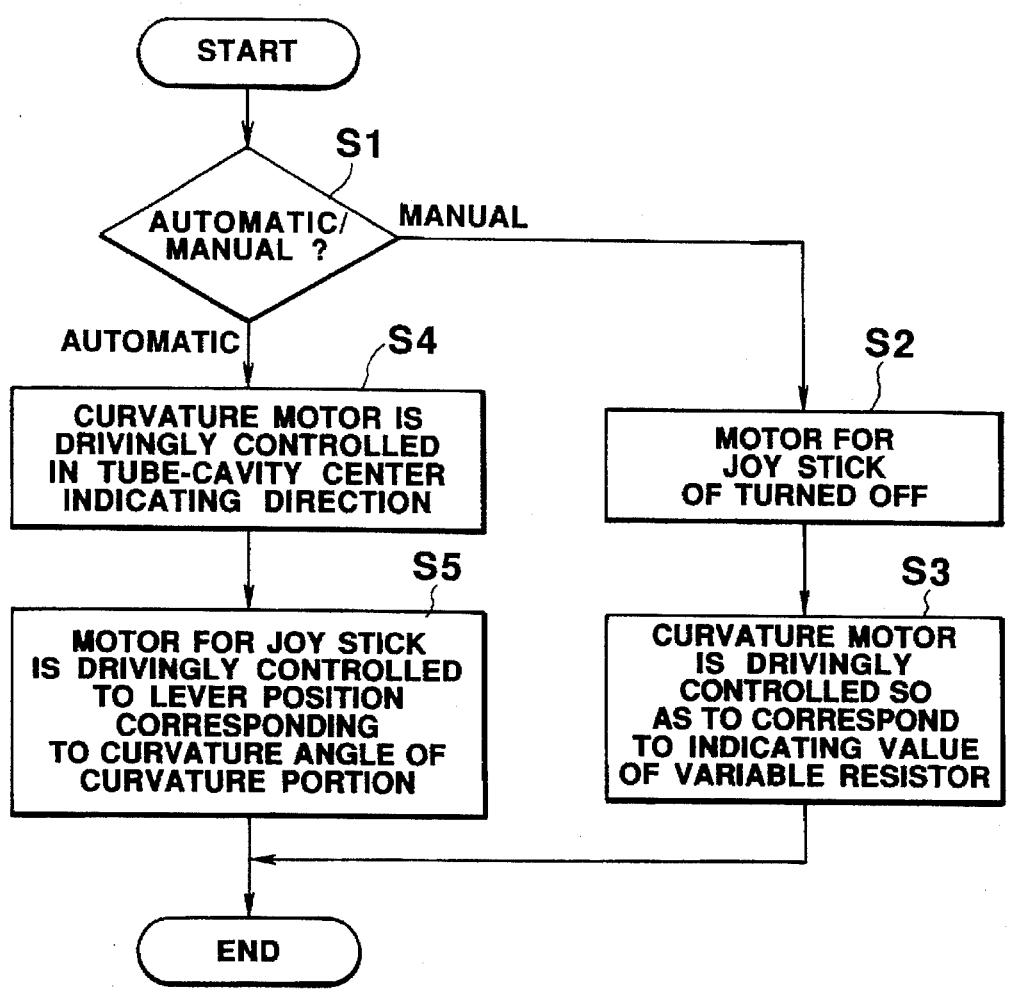

The process for the control of the curving motors 229 and 230 and the joy stick motors 236 and 237 by the above mentioned curving controlling means 227 is shown in the flow chart in FIG. 65. First of all, in the step S1 (hereinafter mentioned merely as S1 by omitting "the step"), it is judged whether the switching switch 228 is automatic or manual.

Here, in case it is manual, the process will proceed to S2 in which the joy stick motors 236 and 237 are switched off. In S3, the curving motors 229 and 230 are driven and controlled so as to correspond to the instructing values of the variable resistors 234 and 235, that is, so that the resistance values of the variable resistors 234 and 235 and the outputs of the encoders 231 and 232 may fill the predetermined function. Thereby, the curvature section 220 curves by an angle corresponding to the instruction of the curving switch 222.

On the other hand, in case the switching switch 228 is automatic, the process will proceed to S4 in which the curving motors 229 and 230 are driven and controlled in the tube cavity center instructing direction by the tube cavity center detecting circuit 226. Then, in S5, the joy stick motors 236 and 237 are driven and controlled so that the operating lever 244 of the curving switch 222 may be positioned corresponding to the actual curvature angle of the curvature section 220. Thereby, the operating lever 244 of the curving switch 222 is driven so as to be of the instructing value corresponding to the curvature angle of the curvature section 220.

As in the above, in this embodiment, as the curving switch 222 is driven so as to follow the actual curved state of the curvature section 220, even in case the curving switch 222 is switched from the automatic curving controlling mode to the manually operated manual curving operating mode on the basis of the tube cavity center instruction by the tube cavity center detecting circuit 226, the instructing value of the curving switch 222 and the curvature angle of the curvature section 220 will always correspond to each other.

Therefore, in case the automatic curving control is switched to the manual curving operation, there will be no quick curving and driving in an unexpected position and no such danger as injures the tube cavity or the like. Therefore, an unexpected curving operation by the non-coincidence of the instructing value of the curving switch 222 and the curvature angle of the curvature section 220 with each other can be prevented and the safety in the curving driving operation of the curvature section can be improved.

The seventh embodiment of the present invention shall be explained with reference to FIGS. 66 to 72.

In the seventh embodiment, there is provided an automatic inserting apparatus wherein the insertable section is automatically inserted by using the tube cavity center detecting circuit of the sixth embodiment. This automatic inserting apparatus is provided fundamentally with not only an automatic curving controlling function but also an insertable section moving function.

The endoscope 401 used in this embodiment is a fiber scope wherein an insertable section 211 and an operating section 212 are provided, a universal cord 213 extended from the operating section 212 is connected to a light source apparatus not illustrated, an illuminating light from the light source apparatus is transmitted by a light guide 417 and is emitted from the end surface on the tip side of the insertable section 211, an eyepiece section 402 is provided at the rear end of the operating section 212 and a television camera 403 is to be fitted to this eyepiece section.

The tip surface of an image guide 419 is arranged in the image forming position of an objective lens 418 of the above mentioned endoscope 401. This image guide 419 is inserted through the insertable section 211 and operating section 212 and its rear end surface is opposed to an eyepiece lens not illustrated within the above mentioned eyepiece section 402. An object image formed by the objective lens 418 is transmitted to the eyepiece section 402 by the image guide 419 and is imaged by the television camera 403 fitted to this eyepiece section. The output signal of the above mentioned television camera 403 is to be input into an image input part 461 of an automatic inserting apparatus 460.

A plurality of angle wires 404 are inserted through the insertable section 211, are fixed at the tips to the tip of the curvable section 220 and are wound at the rear ends around a pulley 406 within a curving driving part provided within the operating section 212. A gear 407 is fitted to the rotary shaft of this pulley 406.

A curving motor 408 is provided within the operating section 212. The above mentioned gear 407 is meshed with a gear 409 fitted to the output shaft of this curving motor 408. A potentiometer 410 is fitted to the rotary shaft of the above mentioned pulley 406. This potentiometer 410 and the above mentioned curving motor 408 are connected to a curving controlling means 462 within an automatic inserting apparatus 460.

This curving controlling means 462 is connected to an endoscope tip curvature instructing means 463 instructing the curving direction of the endoscope tip provided within the automatic inserting apparatus 460. This endoscope tip curvature instructing means 463 is connected to a center position comparing part 464 detecting the position of the tube cavity center from the detected dark region and the variation of the center coordinate.

An insertable section advancing and retreating apparatus 411 is fitted to the insertable section 211, is rotatably fitted to a fitting plate 412 and has two rollers 413 holding the insertable section from both sides. Gears 414 meshing with each other are fitted respectively to the ends of these two rollers 413. Therefore, the two rollers 413 will rotate in the directions reverse to each other and, as a result, the insertable section 211 held between the two rollers 413 will advance and retreat. A gear 416 fitted to the output shaft of the motor 415 is meshed with one gear 414.

The above mentioned motor 415 is connected to a driving controlling means 465 within the automatic inserting apparatus 460. This driving controlling means 465 is connected to an endoscope retreat instructing means 467 instructing the retreat of the insertable section 211 through a switch 466 and an endoscope advance instructing means 469 instructing the advance of the insertable section 211 through a switch 468.

The automatic inserting apparatus 460 shall be explained in the following. An image signal input from an image input part 461 within the automatic inserting apparatus 460 is input into a plurality, for example, of three divaluing circuits (1 to 3) 470a to 470c. These respective divaluing circuits 470a to 470c convert the endoscope images to divalued images respectively with the threshold levels set by threshold level setting parts (1 to 3) 471a to 471c as threshold values. By the way, the respective threshold level setting parts 471a, 471b and 471c are different from one another in the threshold level.

The above mentioned divaluing circuit 470 (representing 470a to 470c) consists, for example, of a comparator and an image signal from the image input part 461s and a reference voltage by the threshold level setting part 471 (representing 471a to 471c) are applied to its input end. The output of the above mentioned comparator will be 0 when the image signal is above the threshold level and will be 1 when the image signal is below the threshold level.

Here, setting the reference voltage in the threshold level setting part 471 shall be explained.

Figure 67A:
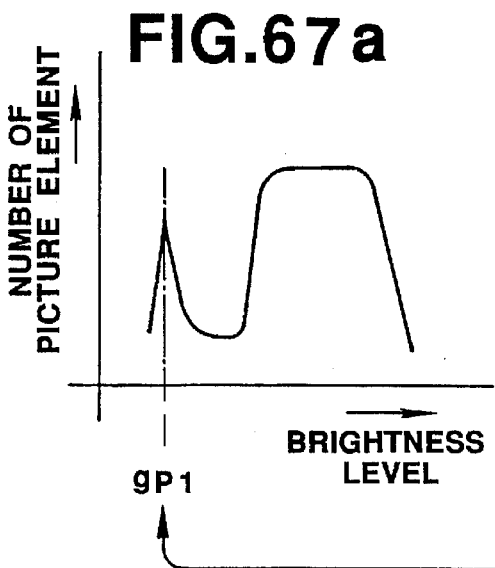
Figure 67B:
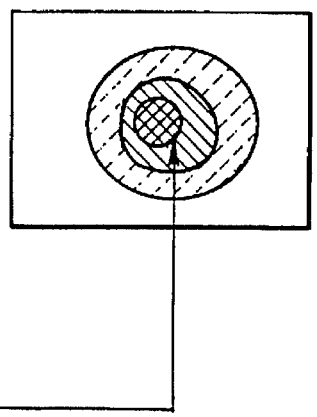

In such endoscope image as is shown in FIG. 67b, a histogram relating to such brightness level as is shown in FIG. 67a is obtained. The first peak (first peak as seen from the dark side) on this histogram is known to correspond to the dark region of the endoscope image for judging the inserting direction of the endoscope. By the way, FIG. 67a is a histogram showing the number of pixels on each brightness level. FIG. 67b shows an endoscope image darker in the center.

Therefore, the above mentioned threshold level had better be set from the value of the brightness level of the first peak of the histogram. For example, as shown in FIG. 67a, if the brightness level (gray level) of the first peak is g p1, the threshold level for setting the darkest region among a plurality of regions corresponding to the brightness will be set to be g p1.

The image signal from the above mentioned image input part 461 is input into the divaluing circuit 470a to 470c, is converted to a digital signal by an A/D converter 472 and is then input into a histogram making part 473. This histogram making part 473 determines the total number of pixels in each brightness level and makes such histogram as is shown in FIG. 67a.

The brightness level g p1 of the first peak of the histogram made by this histogram making part 473 is detected by the first peak detecting part 474. The brightness level g p1 of the first peak detected by this first peak detecting part 474 is to be input into the respective threshold level setting parts (1 to 3) 471a to 471c.

Here, the threshold level setting part (1) 471a for setting the darkest region consists, for example, of a D/A converter, converts the above mentioned brightness level g p1 to an analogue voltage and applies the analogue voltage to one input end of the comparator forming the divaluing circuit 470a.

The threshold level setting parts (2) 471b and (3) 471c for setting the other regions consist, for example, of a D/A converter converting the above mentioned brightness level g p1 to an analogue voltage and an amplifier multiplying the output of this D/A converter by a predetermined coefficient larger than 1 and apply the output of this amplifier to one input end of the comparator forming the divaluing circuits 470b and 470c.

That is to say, the threshold level of the darkest region is set to be g p1 and the threshold level of the other region is set to be of a value larger than g p1.

By the way, in the case of setting the threshold level of the other region, a predetermined value may be added to g p1.

The output signals of the above mentioned divaluing circuits 470a to 470c are to be input respectively into the dark part extracting parts (1 to 3) 475a to 475c. This dark part extracting part 475 (representing 475a to 475c) divalues the respective pixels of the input image as mentioned above. Here, in the divalued image in which the respective pixels have been divalued, the region of the pixels in which the divalued value is 1 is a dark part. Thus, when the threshold level is set and the region darker than it is extracted, when there is only such intermediate darkness as a shadow, mistaking the shadow for the advancing direction will be able to be prevented.

Figure 68:
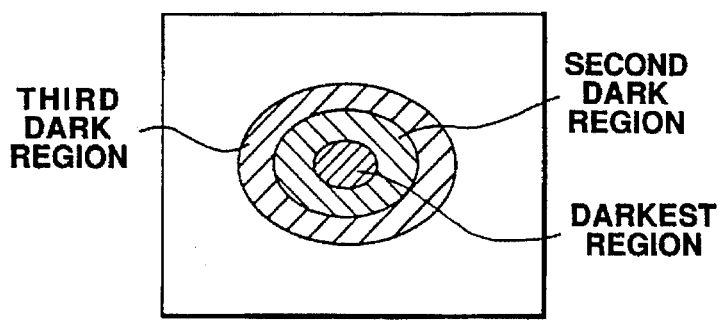

Examples of three dark regions extracted thus by the three dark part extracting parts 475a to 475c are shown in FIG. 68.

The output signal of one dark part extracting part (1) 475a is to be input into a pattern comparing part 476 which operates the correlation between the image from the above mentioned dark part extracting part (1) 475a and the compared pattern memorized in a pattern memorizing part 477 and will judge the correlative value to be of an analogous pattern in case the correlative value is above the set value.

Figure 69:
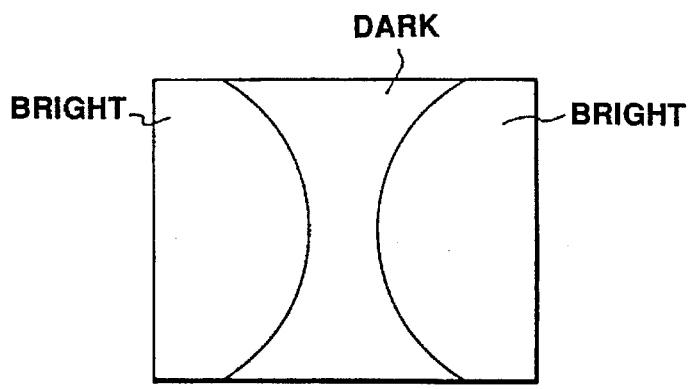

In case such pattern as is shown, for example, in FIG. 69 is made by a dark part extraction or in case the entire region becomes dark, it will be shown that the tip of the endoscope 401 is brought too close to such object to be inspected as a mucous membrane and therefore, in the above mentioned pattern comparing part 476, such pattern will be recognized and an instructing signal to retreat the endoscope will be output. By the way, in case the tip of the endoscope 401 is in contact with the mucous membrane, the entire visual field will become entirely dark but, in case a little apart, lights from two illuminating lenses (in case illuminating lights are emitted from two illuminating lenses) will be incident and, therefore, as shown in FIG. 69, arcuate bright parts will be made at both ends of the visual field.

The output signal of the above mentioned pattern comparing part 476 is selectively input into either of an endoscope retreat instructing means 467 and a boundary extracting part (1) 479a through a switching switch 478 of one input and two outlets. By the way, in case a pattern analogous to a compared pattern is recognized in response to the compared result of the above mentioned pattern comparing part 476, the above mentioned switching switch 478 will be switched to the endoscope retreat instructing means 467 side and an instructing signal to retreat the endoscope will be input into the above mentioned endoscope retreat instructing means 467.

The output of this endoscope retreat instructing means 467 is input into the above mentioned driving controlling means 465 through the switch 466 and is input also into a joy stick driving controlling means 481 driving and controlling the joy stick.

On the other hand, in case a pattern analogous to the compared pattern is not recognized, the above mentioned switching switch 478 will be switched to the boundary extracting part (1) 479a side and the divalued image from the dark part extracting part (1) 475a will be input into the boundary extracting part (1) 479a.

The output signals of the other dark part extracting parts (2 and 3) 475b and 475c are input respectively into the boundary extracting parts (2 and 3) 479b and 479c. This boundary extracting part 479 (479a to 479c) determines a coordinate in which divalued data vary from 0 to 1 or from 1 to 0 for each line of the divalued image obtained by the above mentioned dark part extracting part 475, makes the boundary data of the coordinate 1 and makes the boundary data of the other coordinate 0. That is to say, when the divalued data for the n-th line and m-th pixel are represented by an and m, the boundary data bn and m will be given by the following formula:

$$b_{n,m} = |a_{n,m-1} - a_{n,m}|$$

The output signals of the above mentioned boundary extracting parts 479a to 479c are input respectively into the center extracting operating parts (1 to 3) 480a to 480c. This center extracting operating part 480 (representing 480a to 480c) extract the center coordinate of the extracted dark part.

Figure 70:
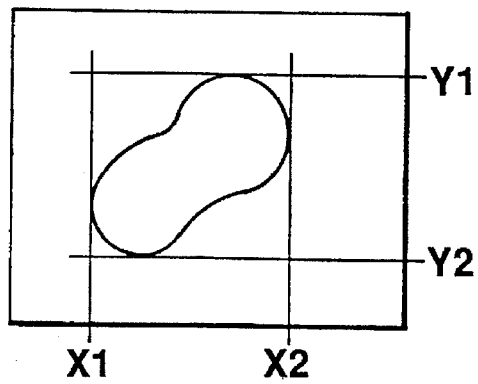

That is to say, as shown, for example, in FIG. 70, in the data of the extracted dark part, the uppermost line and lowermost line of the lines in which the pixels in which the data are 1 exist are extracted and the average value (Y1+Y2)/2 of the Y coordinates Y1 and Y2 of these two lines is made a Y axis center coordinate. In the same manner, the rightmost row and leftmost row of the rows in which the pixels in which the data are 1 exist are extracted and the average value (X1+X2)/2 of the X coordinates X1 and X2 of these two rows is made an X-axis center coordinate.

By the way, as a method of extracting the center coordinate of the dark part, the number N of the pixels contained in the dark part is determined, the pixels contained in the dark part are counted in turn in the X axis direction from above and the Y coordinate when the number becomes N/2 is made a Y axis center coordinate. In the same manner, the pixels contained contained in the dark part are counted in turn in the Y axis direction from the left and the X coordinate when the number becomes N/2 may be made an X axis center coordinates.

The output signals of the above mentioned center extracting operating parts 480a to 480c are input into the center comparing part 464 in which, for the respective center coordinates P1 (x1, y1), P2 (x2, x2) and P3 (x3, y3), $$(X1, Y1) = (x2-x1, y2-y1) \text{ and}$$

$$(X2, Y2) = (x3-x2, y3-y2)$$

are calculated and the variation of the center coordinate of each region is detected. By the way, the above mentioned P1, P2 and P3 are in the dark order of the threshold levels.

The output signal of the above mentioned center position comparing part 464 is input into the endoscope advance instructing means 469 which sets the advancing direction of the endoscope in the P3 (x3, y3) direction and outputs an advance instructing signal to the above mentioned driving controlling means 465 through the switch 468 and also to the joy stick driving controlling means 481.

That is to say, in response to the movement of the center coordinate of the detected dark part, the curving direction of the curvature section 220 is varied and controlled so that the tip of the insertable section 211 may be always directed to the tube cavity center.

The above mentioned joy stick driving controlling means 481 is connected through a switch 482 to a joy stick 483 instructing the advance and retreat of the insertable section 211 so that the operating lever of the joy stick 483 may be driven the same as in the sixth embodiment by the control of the joy stick driving controlling means 481. Also, the joy stick 483 is connected to the driving controlling means 465 through a stick 484 so that, in response to the instruction of the joy stick 483, the motor 415 may be driven and the insertable section may advance and retreat. By the way, though not illustrated, the same as in the sixth embodiment, the joy stick 483 is provided with such driving means as a motor driving the operating lever.

A power source of a voltage V is connected to the control signal input ends of the above mentioned switches 466, 468, 482 and 484 through a resistance 485. Also, this power source can be earthed through a switching switch 486 provided in the operating section 212 or the like of the endoscope 401.

Figure 66:
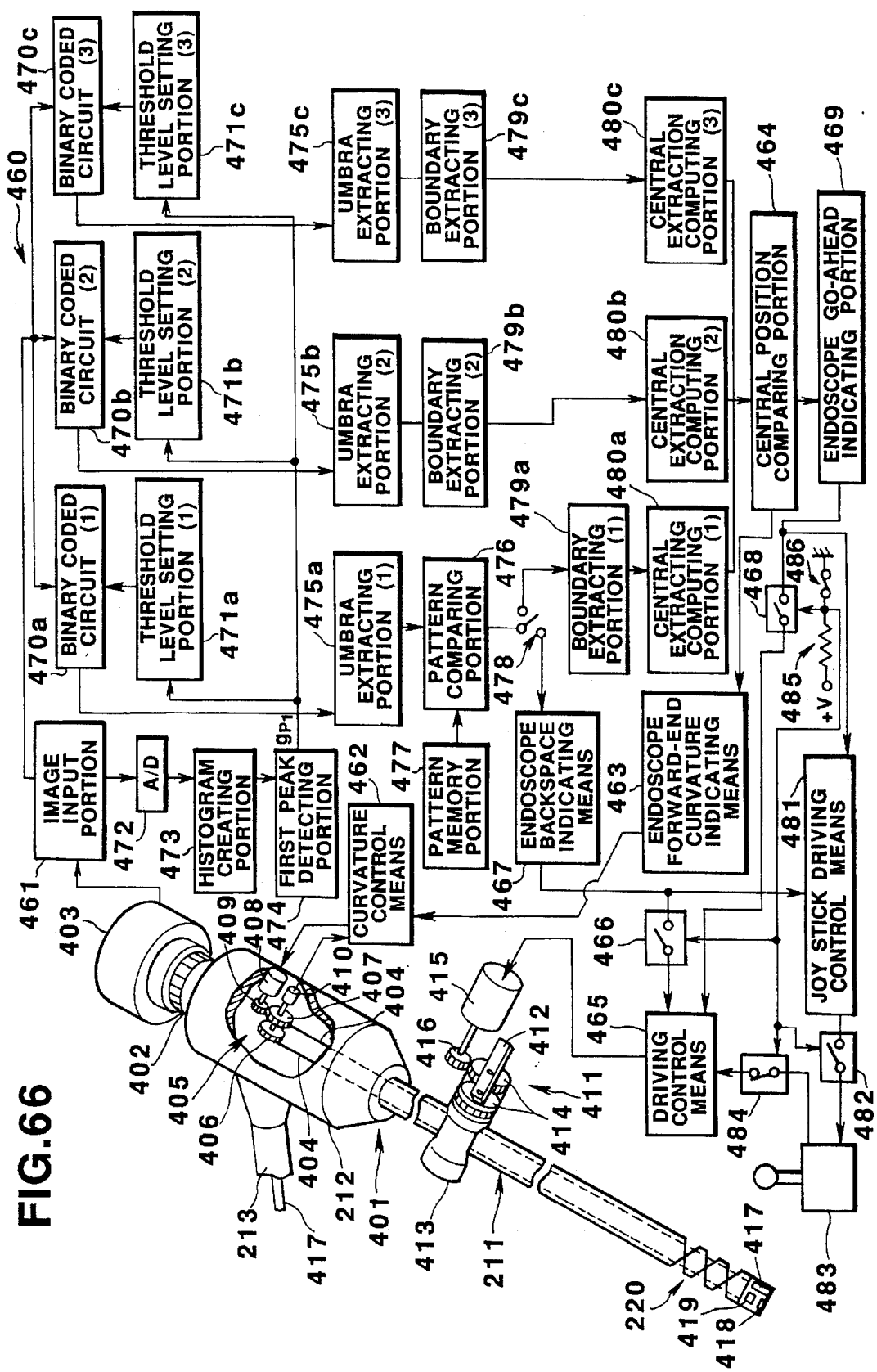
FIGS. 66 to 72 relate to the seventh embodiment of the present invention, FIG. 66 being a block diagram showing the formation of an endoscope and automatic inserting unit.

Therefore, the above mentioned switches 466, 468, 482 and 484 is switched on/off in response to the selection of the switching switch 486. Here, when the insertion by the instruction of the joy stick 483 is selected by the switching switch 483, each switch will be opened or closed as shown in FIG. 66 and the output signal of the joy stick 483 will be input into the driving controlling means 465.

On the other hand, when the switching switch 486 is switched to select the automatic insertion, each switch will be opened or closed reversely to the opened or closed state shown in FIG. 66, the output signals of the endoscope retreat instructing means 467 and endoscope advance instructing means 469 will be input into the driving controlling means 465 and the automatic insertion will be made.

By the way, in the automatic insertion, as the switch 482 is on, the output signal of the joy stick driving controlling means 481 will be input into the joy stick 483 and the operating lever of the joy stick 483 will be driven in response to the insertion of the insertable section 211.

The operation of this embodiment shall be explained in the following.

An endoscope image imaged with the television camera 403 is input into the image inputting part 461 within the automatic inserting apparatus 460 and is divalued on three different threshold levels by the divaluing circuit 470 and the dark part region corresponding to each threshold level is extracted in the dark part extracting part 475.

Further, the boundary of the region is extracted in the boundary extracting part 479 and the center of each region is determined in the center extracting operating part 480. The center positions of the respective regions are compared in the center position comparing part 464. In response to the result, the endoscope inserting condition is set.

Here, when the automatic insertion is selected by the switching switch 486, the advance instructing signal of the endoscope advance instructing means 469 will be input into the driving controlling means 465, the insertable section advancing and retreating apparatus 411 will be driven by the driving controlling means 465 according to the above mentioned inserting condition and the insertable section 211 will be inserted. In case a specific pattern is recognized in the pattern comparing part 476, the instructing signal of the endoscope retreat instructing means 467 will be input into the driving controlling means 465 and the insertable section 211 will be retreated.

The output of the above mentioned center position comparing part 464 will be input also into the endoscope tip curvature instructing means 463. In case the center position of the dark part region lags from the center of the endoscope image, the above mentioned endoscope tip curvature instructing means 463 will output a curvature instructing signal to the curving controlling means 462.

By the way, the center position of the dark part region to be used for the curvature control may be determined on the basis of any one of the respective center coordinates P1, P2 and P3 of the three dark part regions corresponding to the three threshold levels or on the basis of two or more of them. The above mentioned curving controlling means 462 will rotate the motor 408 in response to the above mentioned curvature instructing signal. Thereby, the wire 404 will be pushed and pulled through the pulley 406 and the curvature section 220 will be curved. The rotation amount of the above mentioned pulley 406 will be detected by the potentiometer 410 and will fed back to the curving controlling means 462 so that the curvature section 220 may be curved to the curvature angle predetermined by the curvature instructing signal. By the way, in the drawing, only the curving driving part 405 in two directions is shown. However, when two sets of the curving driving parts 405 are provided, curving controlling in four directions will be possible.

Figure 71A:
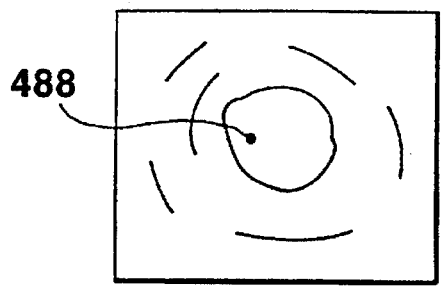
Figure 71B:
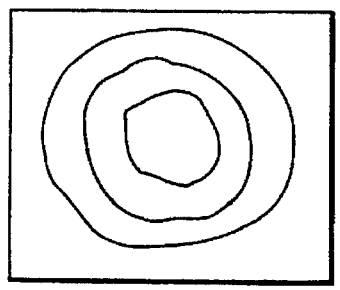
Figure 71C:
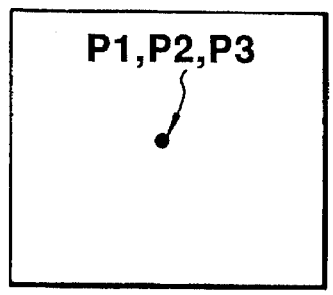

Here, in case the tube cavity 488 in which the endoscope 401 is to be inserted is straight, the endoscope image will be as shown in FIG. 71a and the boundaries of the respective regions will be as shown in FIG. 71b. By the way, in FIG. 71b, the inside is a darker region. In such case, as shown in FIG. 71c, the centers P1, P2 and P3 of the respective regions will substantially coincide with one another. In such case, as the endoscope may advance at a high speed, in the endoscope advance instructing means 469, the advancing direction will be set in the P3 direction and the advancing speed will be set at a high speed.

Figure 72A:
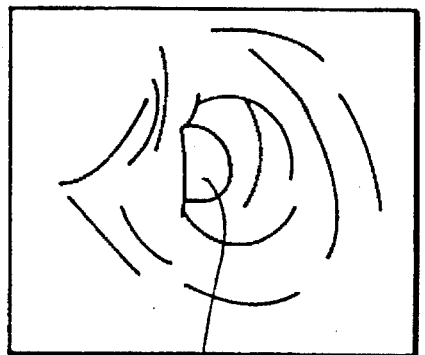
Figure 72B:
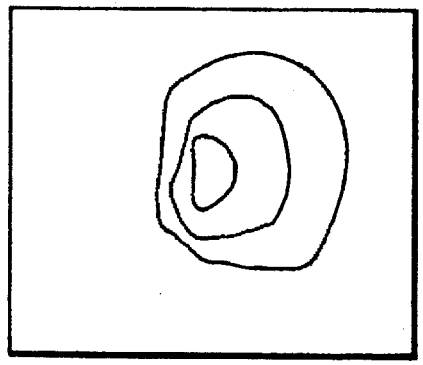

On the other hand, in case the tube cavity 488 in which the endoscope 401 is to be inserted is curved, the endoscope image will be as shown in FIG. 72a and the boundaries of the respective regions will be as shown in FIG. 72b. By the way, in FIG. 72b, the inside is a darker region.

Figure 72C:
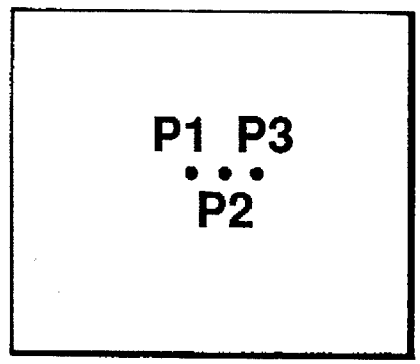

In such case, as shown in FIG. 72c, the centers P1, P2 and P3 of the respective regions will lag in response to the curved state. In such case, it will be necessary to advance the endoscope in response to the curved state of the tube cavity. Therefore, the above mentioned endoscope advance instructing means 69 will set the advancing direction in the P3 direction and will set the advancing speed at a medium speed or low speed.

By the way, in case the centers of the respective regions lag as in FIG. 72c, the advancing direction may lag in the order of P3, P2 and P1.

In the automatic insertion, the output controlling signal of the joy stick driving controlling means 481 will be input into the joy stick 483 through the switch 482 and the operating lever of the joy stick 483 will be driven and controlled. Thereby, the operating lever of the joy stick 483 will be controlled so as to incline in response to the inserted state of the insertable section 211.

In case the joy stick 483 is selected by the switching switch 486, the instructing signal of the joy stick 483 will be input into the driving controlling means 465 through the switch 484, the motor 415 will be driven according to the instruction of the joy stick 483 and the insertable section will advance and retreat.

Here, in case the automatic insertion is switched to the manual insertion by the instruction of the joy stick 483, as the inclination of the operating lever of the joy stick 483 always corresponds to the insertion amount of the insertable section 211, the insertable section will not be quickly inserted and driven but will be smoothly inserted by the instruction of the joy stick 483.

As in the above, in this embodiment, as the operating lever of the joy stick 483 is driven to follow the actual inserted state of the insertable section, even in case the automatic inserted state by the automatic inserting apparatus 460 is switched to the manual inserted state by the joy stick 483, the instructed value of the joy stick and the inserted amount of the insertable section 211 will always coincide with each other.

Therefore, in case the automatic insertion control is switched over to the manual inserting operation, the insertable section will not be quickly inserted and driven, such danger as injuring the tube cavity or the like will be able to be prevented and the safety in the inserting and driving operation will be able to be improved.

By the way, even in the case of not only the inserting operation of advancing and retreating the insertable section 211 but also the insertable section 211 twisting operation by the twisting apparatus fitted to rotate the roller by 90 degrees and to hold the insertable section 211 in the axial direction, this embodiment will be able to be applied in the same manner.

Also, the same curving switch as in the sixth embodiment can be connected to the curving controlling means 462 through the switching switch so that, in the automatic inserted state, this curving switch may be driven to follow the curvature angle of the curvature section 220.

The eighth embodiment of the present invention shall be explained in the following. This embodiment is an endoscope apparatus adapted to the operation of inserting the insertable section into a large intestine or the like so that the operation of curving the curvature section and the operation of making the curvature section straight may be quickly made. Also, this embodiment comprises a joy pad provided with a plurality of on/off switches corresponding to the directions in which the curving switch curves the curvature section.

Figure 74:
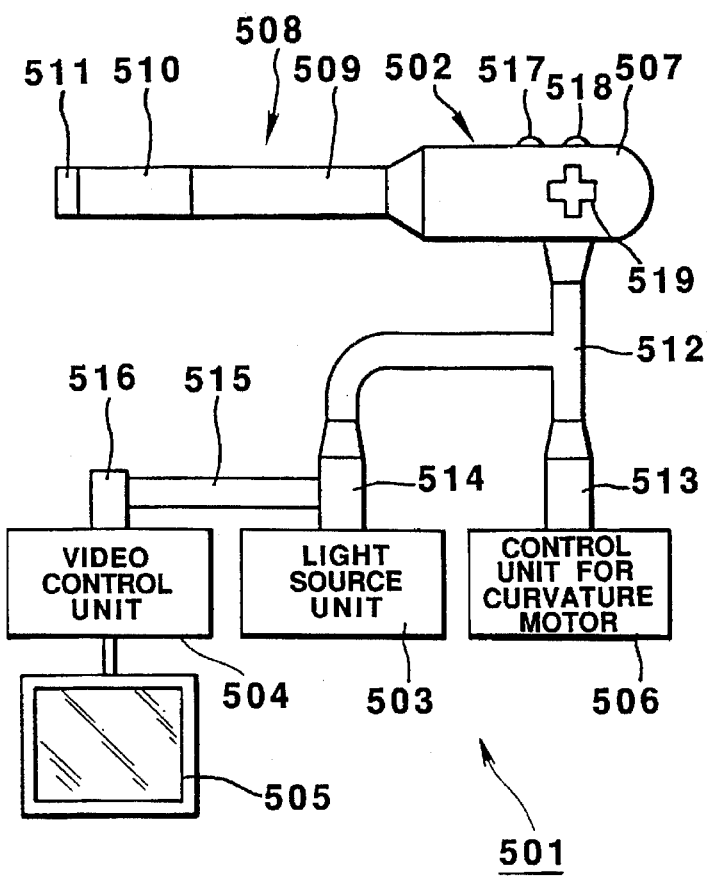

As shown in FIG. 74, the endoscope apparatus 501 of the eighth embodiment comprises an electronic endoscope 502 internally provided with such solid state imaging device as a CCD, a light source apparatus 503 feeding an illuminating light to this electronic endoscope 502, a video controlling apparatus driving the above mentioned solid state imaging device and converting the image signal from this solid state imaging device to a video signal, a monitor 505 displaying the video signal output from the video controlling apparatus 504 and a curving motor controlling apparatus 506 controlling the curvature of the curvature section 510 of the later described electronic endoscope 502.

The electronic endoscope 502 is provided with an operating section 507 and an insertable section 508 connected to this operating section 507 and formed to be elongate so as to be insertable into an object to be observed.

To this insertable section 508 are connected a soft section 509, curvature section 510 and tip section 511 in the order mentioned in the tip direction from the above mentioned insertable section 507.

The curvature section 510 is made by connecting a plurality of curved pieces so as to be curvable in the vertical and horizontal directions, Also, the tip section 511 is internally provided with an objective optical system including the solid state imaging device and an illuminating optical system or the like.

Signal cables not illustrated inserted through the insertable section 508 are electrically connected to the solid state imaging device and are extended to the later described video controlling apparatus connector 516.

As an illuminating optical system, a light guide fiber bundle is arranged within the insertable section 508 and is extended to the later described light guide connector 514. A universal cord 512 branched into two steps in the course is connected to the side of the operating section 507.

This universal cord 512 is provided at the ends with a motor controlling apparatus connector 513 removably connected to the curving motor controlling apparatus 506 and a light guide connector 514 removably connected to the light source apparatus 503.

A video controlling cord 515 is extended from the side of the light guide connector 514 and is provided at the end with a video controlling apparatus connector 516 removably connected to the video controlling apparatus 504.

The operating section 507 is provided with an air feeding/water feeding button 517b for cleaning the observing window and a sucking button 518 for sucking a body liquid or the like.

When the air feeding/water feeding button 517, air or water will be fed and, when the sucking button 518 is operated, a suction will be made from a sucking channel (treating instrument inserting channel) arranged within the electronic endoscope 502.

The operating section 507 is provided with a curving operating switch 519 which is a curving operating apparatus for curving operating the curvature section 510 and is connected to a controlling circuit within the curving motor controlling apparatus 506.

Figure 75:
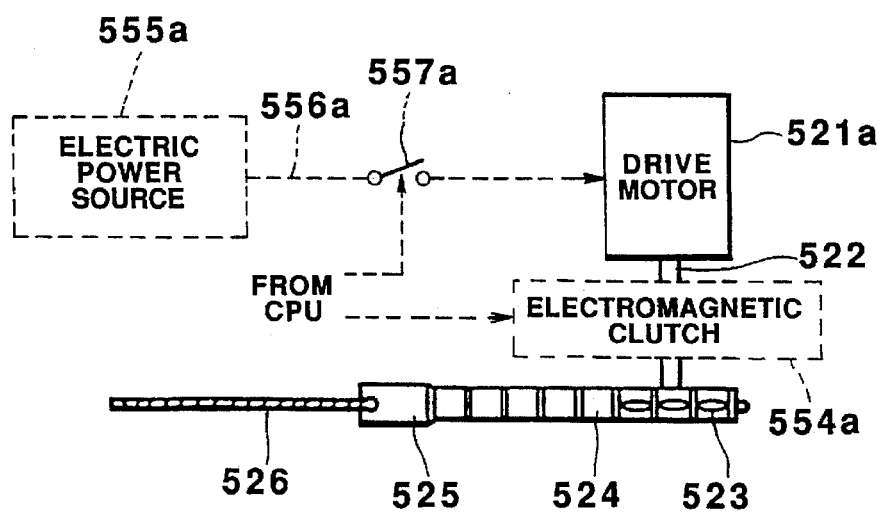

This operating section 507 is provided within it as shown in FIG. 75 with a driving motor 521a comprising a direct current motor curving and driving the curvature section in the vertical direction, a sprocket 523 fixed to the driving shaft 522 of this driving motor 521a and a chain 524 meshing with this sprocket 523 (by the way, the electromagnetic clutch 554 shown by the dotted line shall be described later).

A curving operating wire 526 is connected to the end of the chain 524 through a connecting member 525 is inserted through the above mentioned soft section 509 and curvature section 510 and is connected to the curving piece at the tip of the curvature section 510.

The thus formed curving driving section is connected to the curving motor controlling apparatus 506. When the curving operating switch 519 is operated, the driving motor 521a will be driven, will pull and operate the operating wire 526 and will curve and drive the curvature section 510 in the vertical direction. The curving driving controlling means is formed of this curving driving section and the curving motor controlling apparatus 506.

By the way, here, the driving section curving and driving in the vertical direction has been described. However, a driving section curving and driving in the horizontal direction is also formed in the same manner.

The formation of the curving operating switch 519 shall be explained in the following with reference to FIGS. 76 to 80.

Figure 76:
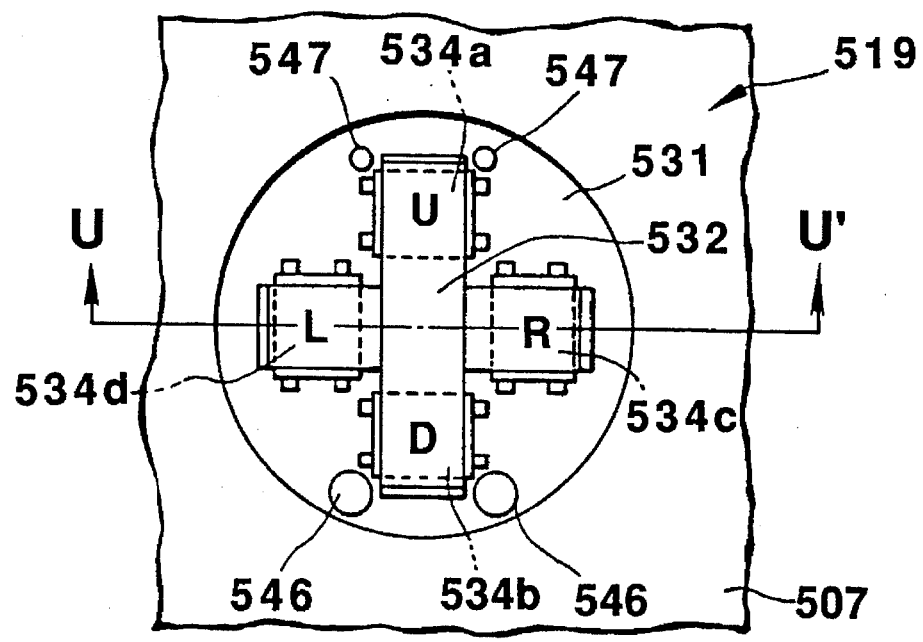
Figure 77:
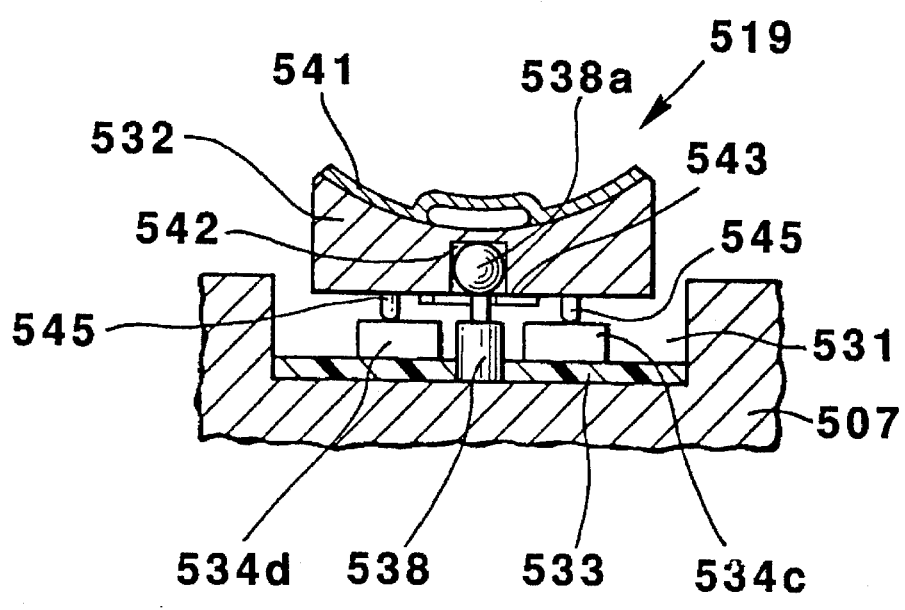

As shown in FIGS. 76 and 77, in the curving operating switch 519, the essential part is formed of the operating section 507 provided with a countersunk hole 531 in which a joy pad or cross pad 532 is arranged.

The countersunk hole 531 is formed to be a circular recess larger than the above mentioned cross pad 532. A substrate 533 (See FIG. 77) is fixed to the bottom surface of the above mentioned countersunk hole 531. On this substrate 533, four tact switches 534a, 534b, 534c and 534d corresponding to the respective directions of U (up), D (down), R (right) and L (left) are substantially symmetrically provided in four directions from the center of the substrate 533. In the central part of the bottom surface of the countersunk hole 531, a pad shaft 538 having a spherical part 538a at the upper end is erected upward.

The four projections forming the cross pad 532 correspond respectively to the curving operating directions of the U, D, R and L (up, down, right and left). As shown in FIG. 77, this cross pad 532 is an arcuate recess on the finger touch surface 541 on the upper end side on the side reverse to the countersunk hole 531, the curvature in the RL direction is smaller than the curvature in the UD direction and the projection end of the cross pad 532 is higher in the RL direction.

Figure 78:
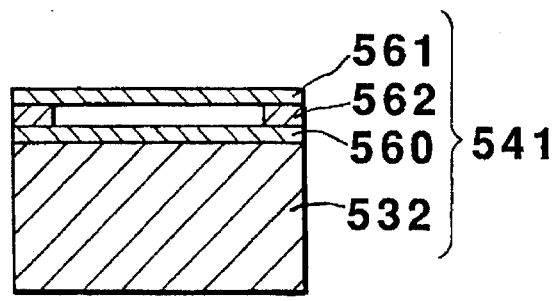
Figure 79:
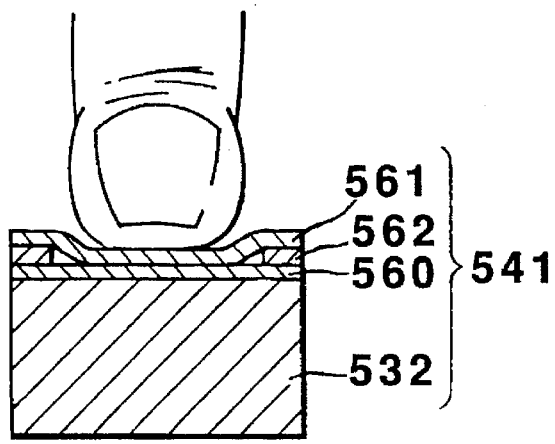

As shown in FIG. 78, the finger touch surface 541 is a touch sensor detecting the touch state of the operating finger. That is to say, the finger touch surface 541 is formed by inserting a spacer 562 between two electrode films 560 and 561 which will be kept at a fixed distance by the spacer 562 at the time of no load. When this finger touch surface 541 is pushed with a finder, the electrode films 560 and 561 will conduct with each other as shown in FIG. 79.

A signal line not illustrated is connected to these electrode films 560 and 561 and is connected to the curving motor controlling apparatus 506 through the substrate 533.

Figure 80:
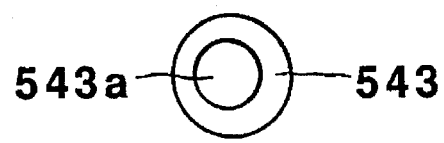

On the other hand, a recess 542 is provided upward in the central part of the lower end surface of the cross pad 532. When the spherical part 538a of the pad shaft 538 is inserted into this recess 542, the pad 532 will be tiltably supported with this spherical part 538a as a center. A removal preventive 543 having such eccentric hole 543a as is shown in FIG. 80 and preventing the above mentioned spherical part 538a from being removed is fixed to the opening of the recess 542. By the way, the cross pad 532 is chamfered at four ends.

Four depressing pins 545 for pushing the tact switches 534a to 534d are provided to project downward at the lower end on the countersunk hole 531 side of the cross pad 532. These depressing pins 545 are provided to be positioned somewhat outside from the centers of the respective tact switches 534a to 534d as seen from the pad shaft 538 so that, in case the cross pad 532 is tilted, the depressing pins 545 may come just to the centers of the pushed tact switches.

On the substrate 533, rotation stoppers 546 of a pair of thick shafts on the D side and rotation stoppers 547 of a pair of thin shafts on the U side are respectively fixed in the form of respectively holding the projections of the above mentioned cross pad 532 to prevent the position lag in the rotating direction of the cross pad 532.

Figure 73:
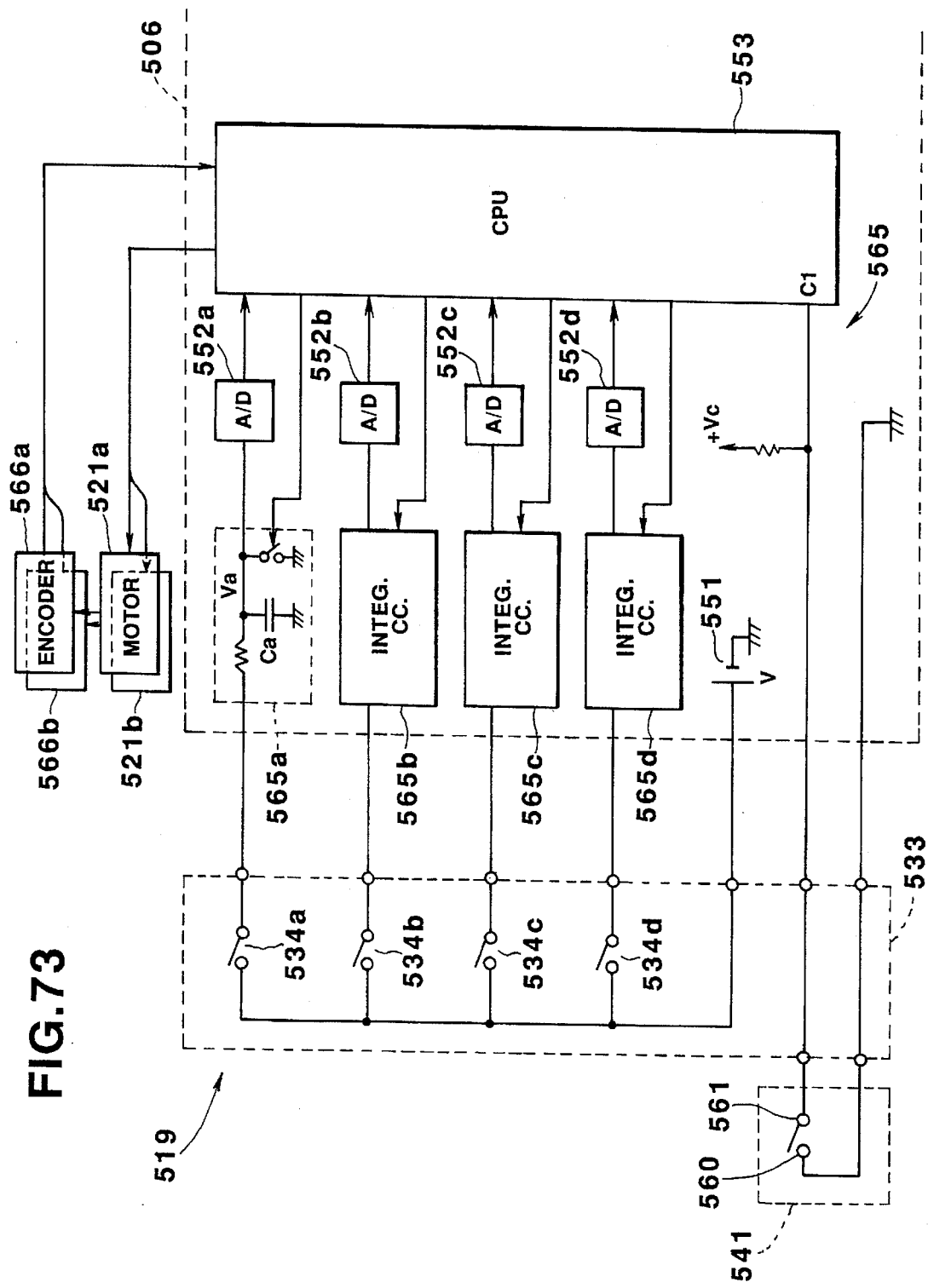
FIGS. 73 to 80 relate to the eighth embodiment of the present invention, FIG. 73 being a block diagram showing a schematic functional formation of an endoscope curvature operation controlling portion.

The schematic functional formation of the endoscope curvature operation controlling section including the curving operating switch 519 and curving motor controlling apparatus 506 formed as in the above shall be explained with reference to the block diagram in FIG. 73.

The curving operating switch 519 is connected to a controlling circuit part 565 making various curving controls provided within a curving motor controlling apparatus 506. That is to say, integrating circuits 565a to 565d of the controlling circuit part 565 are respectively connected to the tact switches 534a to 534d as on/off switches respectively through signal lines so that, for example, when the tact switch 534a is switched on, the voltage V of the direct current power source 551 will be input into the integrating circuit 565a formed, for example, of a resistance and condenser through the tact switch 534a switched on, an integrating operation will be made and a voltage Va proportional to the time when the switch is switched on will be integrated and will be held in a holding condenser Ca holding it.

This voltage Va is converted to a digital amount by the A/V converter 552a and is input as a curving operating instructing signal into the CPU 553. This curving op&rating instructing signal curves upward the curvature section 510 by a curvature angle proportional to the voltage Va. Therefore, if the voltage Va is zero, zero curvature angle will be instructed. In case the other tact switch 534i (i is b to d) is switched on, the voltage will be input into the CPU 553 in the same manner.

The electrode films 560 and 561 functioning as switching switches are also connected with the controlling terminal C1 of the CPU 553 through the signal lines and substrate 533 and the conducting state of the electrode films 560 and 561, that is, the switching on/of is transmitted. In FIG. 73, the electrode film 560 is earthed and the electrode film 561 is connected to the power source end Vc through a resistance.

Therefore, when the electrode films 560 and 561 are switched on, the controlling terminal C1 of the CPU 553 will be made "L" and the CPU will detect that the electrode films 560 and 561 are switched on. Thereby, the operating finger will detect that it is pressing the finger touching surface 541 of the curving operating switch 519. In this embodiment, in case the electrode films 560 and 561 are switched on (that is, in case "L" is detected by the control terminal C1), the CPU 553 will hold the curving operating instructing signal then and will control the curvature of the curvature section to hold the curvature angle corresponding to the this instructing signal.

That is to say, in case the electrode films 560 and 561 are switched on, the operation will be made in a mode corresponding to the mode having no neutral return (as the joy pad has no operating lever, the expression of "corresponding mode" is used).

On the other hand, in case the electrode films 560 and 561 are not switched on (in case "H" is detected), the curving operating instructing signal will be reset to be changed to zero curving operating instructing signal. In such case, the operation will be made in a mode corresponding to the mode of making a neutral return.

The CPU is connected with encoders 566a and 566b connected respectively to the rotary shafts of the vertically curving driving motor 521a, horizontally curving driving motor 521b and driving motors 521a and 521b.

The CPU 553 always compares the instructing signal input from the A/D converters 552a to 552d and the actual curvature angles input from the encoders 566a and 566b with each other and feeds a driving current to the driving motors 521a and 521b so that the curvature angle may coincide with the instructing signal.

That is to say, the CPU 553 feeds a driving electric power to the driving motors 521a and 521b on the basis of the outputs of the A/D converters 552a to 552d varying in response to the switching on or off of the electrode films 560 and 561 and the switching on or off of the tact switches 534a to 534d and the outputs of the encoders 566a and 566b corresponding to the actual curvature angle. That is to say, the driving motors 521a and 521b are driven so that an instructed predetermined curvature state may be made by the operation of the curving operating switch 519.

In case one (for example, 543a) or two (for example, 543a and 543c) of the tact switches 543a to 543d are in the on-state, the current fed to the corresponding driving motors 521a or 521a and 521b in proportion to the time of the on-state will gradually increase and the curvature section 510 will curve in the instructed direction (because the outputs of the integrating circuits 565a to 565d become larger in proportion to the on-time).

The curved amounts of the curvature section 510 are respectively read out by the encoders 566a and 566b connected with the respective driving shafts 522 of the driving motors 521a and 521b. When the values of the encoders 566a and 566b become the set values corresponding to the curved amounts instructed by the curving operating switch 19, the CPU 553 will hold the curvature state so as not to be curved further.

By the way, in case this curving operating switch 519 is operated, the electrode films 560 and 561 will conduct with each other.

When the tact switches 534a to 534d are off and the electrode films 560 and 561 conduct with each other, the CPU 553 will continue to feed an electric power to the driving motors 521a and 521b so as to hold the curved state then. That is to say, when the operation of the curving operating switch 519 is stopped, while the finger touch surface 541 of the switch is only pushed with the operating finger, the driving motors 521a and 521b will be controlled so as to hold the present curved state by the output of the A/D converter 552a.

On the other hand, when the electrode films 560 and 561 do not conduct, the CPU 553 will output a resetting signal to the integrating circuits 565a to 565d and will conduct (for example, by switching on the analogue switch) both ends of the condenser Ca or the like holding the integrated value to make the curvature instructing amount zero. That is to say, in such case, the curvature instructing signal will be to make a straight state of zero curvature angle.

Therefore, when the tact switches 534a to 534d are switched on and are then switched off and the electrode films 560 and 561 do not conduct, the CPU 553 will feed an electric power to the driving motors 521a and 521b so that the curvature section 510 may be straight.

That is to say, when the operating finger is released from the curving operating switch 519, the driving motors 521a and 521b will be controlled to make the curvature section straight.

By the way, the control of the straight state is not limited to be by such controlling method as of monitoring the outputs of the encoders 566a and 566b to make the curvature section 510 straight. The curvature section 510 may be controlled to be in such position that the loads of the driving motors 521a and 521b may be minimum. A curved state controlling means is formed of the curving operating switch 519 having these electrode films 560 and 561 and the controlling circuit part 565.

For example, in a large intestine endoscope, as an inserting technique, the curvature section is curved, the insertable section is hung on a pleat of the inside wall of the large intestine and is pushed in with the curvature section straight while being pulled to the hand base side. By repeating this series of operations, the insertable section is inserted into the large intestine into which it is hard to insert the insertable section.

In such inserting technique, it is difficult to time such operations as the curving operation and straightening operation. Unless the operations are timed, the insertable section will not be able to be well inserted. However, in this embodiment, when only the operating finger is released from the curving operating switch 519 and the conduction of the electrode films 560 and 561 is released, the curvature section 510 will return to be straight, therefore it will not be necessary to operate the cross pad of the curving operating switch 519 to make the curvature section straight and the curvature section 510 will be able to be made straight by a simple operation. Thereby, it will be easy to time the above mentioned respective operations and the insertability and operability will improve.

Also, in case it is wanted to hold the curvature angle of the curvature section 510 at a desired angle, when the curving operating switch 519 is touched and the electrode films 560 and 561 are conducted, the curving driving section will be controlled so that the present curvature state may be held. That is to say, holding a desired curvature angle state and straightening the curvature section can be easily switched over to each other.

As in the above, according to this embodiment, by a simple operation of only varying the curving operating switch pressing state, it is possible to easily instruct either of the straight state and the present curved state of the curvature angle state.

By the way, instead of the operation of the controlling circuit part 565 wherein, when the electrode films 560 and 561 do not conduct, the driving motors 521a and 521b will be controlled so that the curvature section may be straight, the power feed to the driving motors 521a and 521b may be stopped.

That is to say, when the electrode films 560 and 561 are switched off (when the control terminal C1 is "H"), the CPU 553 may switch off the switch 557a provided in the course of the driving line 556 transmitting a driving power (for driving the driving motor 521a) from the power source 555a to the driving motor 521a as shown by the dotted line, for example, in FIG. 75 and may interrupt the power fed to the driving motor 521a.

In this case, the same control will be made also to the other driving motor 521b. In case the operation of the driving motors 521a and 521b stops, the wire 526 will be elastically held by a spring not illustrated so as to return to the neutral position so that the curvature section 510 may return to be straight.

When the electrode films 560 and 561 do not conduct, instead of controlling the driving motors 521a and 521b so that the curvature section may be straight, a clutch means interrupting the transmission of the driving force may be provided between the driving force generating means and driving force transmitting means.

As shown by the dotted line, for example, in FIG. 75, an electromagnetic clutch 554a may be provided between the driving shaft 522 of the driving motor 521a and the sprocket 523 so that, when the electrode films 560 and 561 do not conduct, the CPU 553 may switch off the electromagnetic clutch 554a to interrupt the driving force. In such case, though not illustrated, an electromagnetic clutch 554b may be provided also between the driving shaft of the driving motor 521b and the sprocket and the same control may be made. In this case, too, when the magnetic clutches 554a and 554b are switched off, an elastic holding means for returning the curvature section 510 to be straight will be required.

The curvature section may be controlled not only to be straight but also to return by a predetermined curvature amount to be straight from the present state.

The entire curving operating switch 519 may be coated with a rubber sheet so as to be water-proof. The touch sensor provided on the finger touch surface 541 of the curving operating switch is not limited to be of the above described two, electrode films but may be of piezoelectric films.

Figure 81:
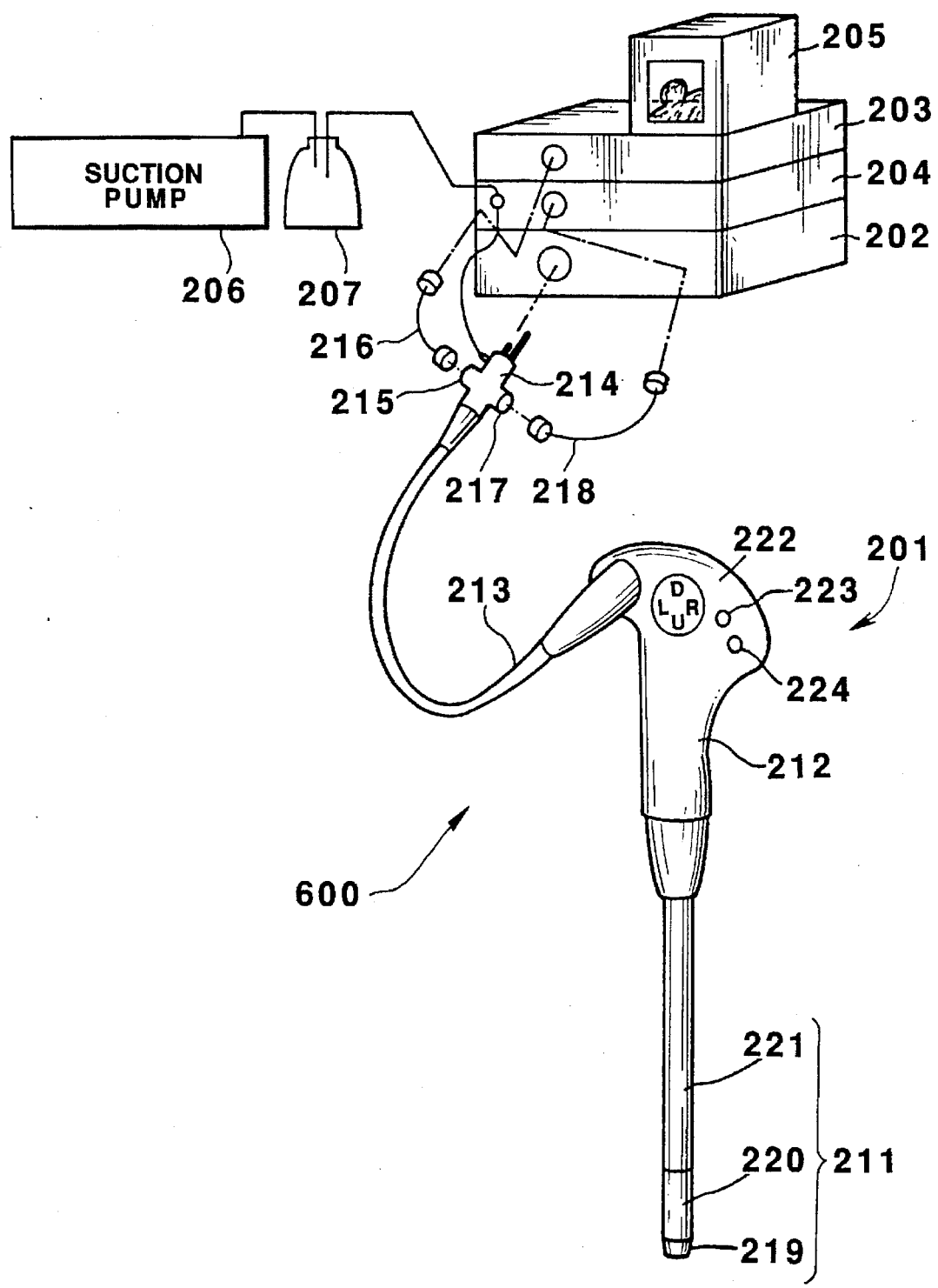
FIGS. 81 to 84 relate to the ninth embodiment of the present invention, FIG. 81 being an entire formation view of an endoscope apparatus.

FIG. 81 shows the entire formation of the endoscope apparatus 600 of the ninth embodiment of the present invention.

In the ninth embodiment, when the curving switch is not operated, it will return to the central position.

As shown in FIG. 81, the endoscope 201 used in this embodiment has an elongate insertable section 211 and is to be connected to a light source apparatus 202, CCU 203 and motor & fluid controlling apparatus 204 through a universal cord 213 extended from an operating section 212 connected to the insertable section 211 at the rear end. The operating section 212 of the endoscope 201 is provided with a curving switch 222 instructing the curving operation. That is to say, this ninth embodiment is formed the same as in the sixth embodiment except that the tube cavity detecting apparatus 208 in the sixth embodiment is not provided. The same components shall bear the same reference numerals and shall not be explained here.

Figure 82:
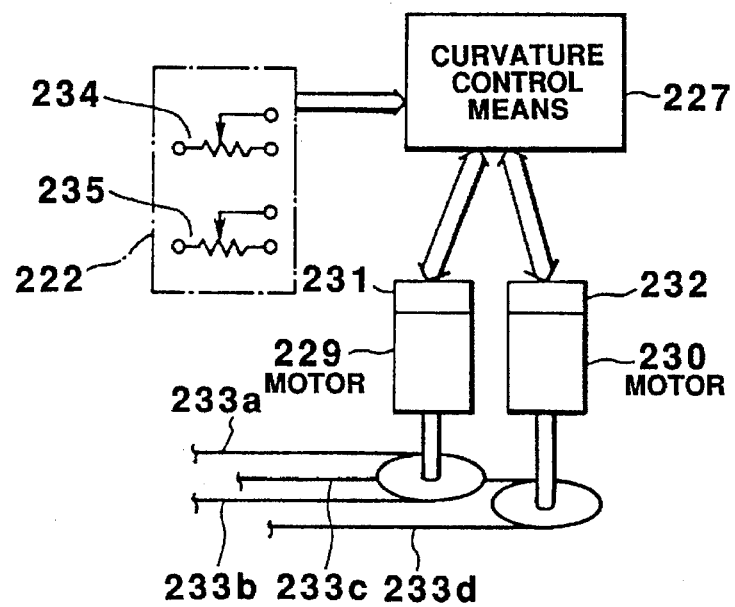

The schematic formation of the curving operating controlling means is shown in FIG. 82. This embodiment is of the same formation as of the sixth embodiment except that the tube cavity detecting apparatus 208 and joy stick motors 236 and 237 shown in FIG. 60 are not provided. The same components shall bear the same reference numerals and shall not be explained here. That is to say, the driving means for driving the curving switch 222 is not provided in the formation.

Figure 83:
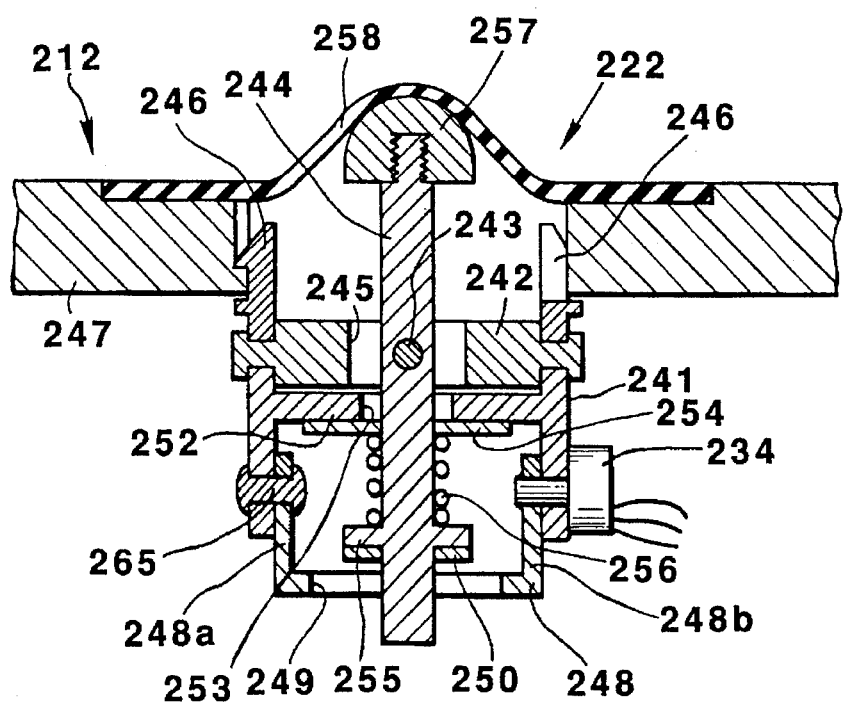

In the curving switch 222, as shown in FIG. 83, the same as in the sixth embodiment, the shaft 242 is rotatably pivoted to the casing 241 and the shaft 243 is rotatably pivoted to the shaft 242 so as to intersect at right angles with the shaft 242. The operating lever 244 is provided so that the shaft 243 may be passed and inserted through the incised part 245 of the shaft 242 and the operating lever 244 may incline with the shafts 242 and 243 as centers.

At the lower end of the casing 241, the same as in the sixth embodiment, the rotors 248 and 250 are rotatably pivoted as intersected at right angles with each other. The resistance setting shaft of the variable resistor 234 is secured to one arm 248b of the rotor 248 and the body of the variable resistor 234 is secured to the side of the casing 241. The other arm 248a of the rotor 248 is pivoted by a pin 265 which is crushed at both ends and is fixed like a rivet. By this formation, when the operating lever 244 is inclined with the shafts 242 and 243 as centers, the rotors 248 and 250 will rotate and accordingly the resistance values of the variable resistors 234 and 235 will vary.

That is to say, the formation is the same as in the sixth embodiment except that the joy stick motor is not provided. The same components shall bear the same reference numerals and shall not be explained here.

When the operating lever 244 of the curving switch 222 is operated and is rotated and inclined with the shafts 242 and 243 as rotary shafts, the rotors 248 and 250 will rotate and the resistance values of the variable resistors 234 and 235 will vary. These resistance values will be input into the curving controlling means 227. The curving controlling means 227 will rotate the curving motors 229 and 230 in response to the input resistance values and will control the drive of the curving motors 229 and 230 so that the outputs of the encoders 231 and 232 and the above mentioned resistance values may fill a predetermined function. Thereby, the curvature section 220 will curve to a curvature angle proportional to the tilting angle of the operating lever 244 of the curving switch 222.

Figure 84:
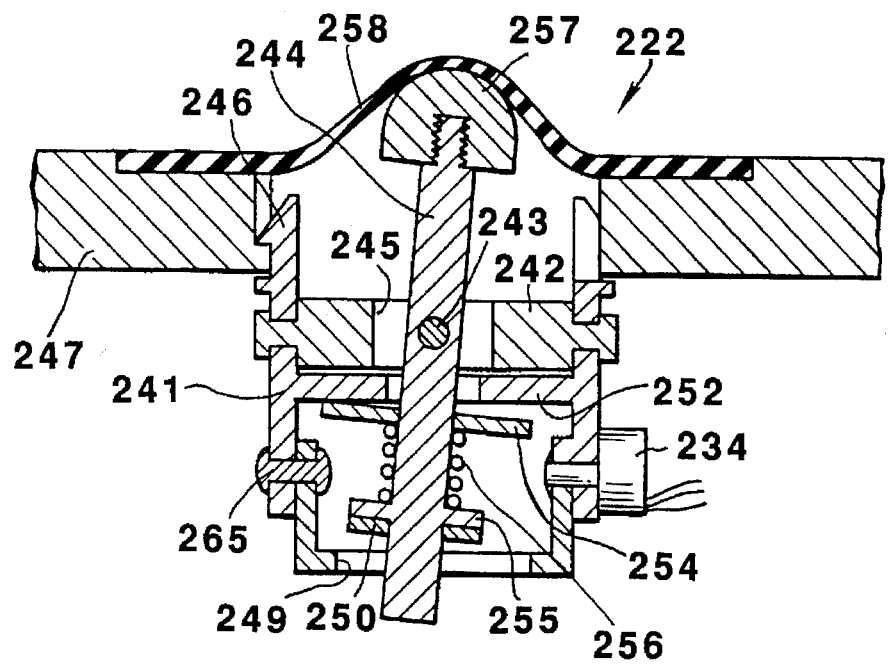

When the operating lever 244 tilts, as shown in FIG. 84, the plate 254 will be pushed by the partition wall 252 of the casing 241 and will slide to the flange part 255 side of the operating lever 244 and the compression spring 256 will be compressed. While the operator operates the operating lever 244 with the finger, the force inclining the operating lever 244 with the finger will be larger than the elastic force of the compression spring 256 and therefore the inclination of the operating lever 244 will be held. On the other hand, when the finger is released from the operating lever 244, the compression spring 256 will push up the plate 254 so that the downward energizing force may be removed by its elastic force. Thereby, the operating lever 244 will be returned to the central position.

Thus, in the ninth embodiment, when the curving switch 222 is not operated, the operating lever 244 will return to the central position and therefore, even in case another controlled state is switched over to the manual curving operation by the curving switch 222, no quick curving drive will be made, such dangerous state as will insure the tube cavity or the like will be able to be prevented and the safety in the curvature section curving and driving operation will be able to be improved.

In case the operator can not catch the curvature angle during the inspection with the endoscope or when the endoscope is to be removed, it will be a rule to make the insertable section tip straight. Therefore, in this embodiment, when the hand is released from the curving switch 222, the operating lever 244 will return to the central position, therefore, the insertable section tip will curve in the straight direction, the straight position will be able to be easily caught and the inspection will be able to be safely made. Further, when the hand is released from the curving switch 222, the insertable section tip will be able to be easily made straight and the operability will be able to be improved.

Figure 85:
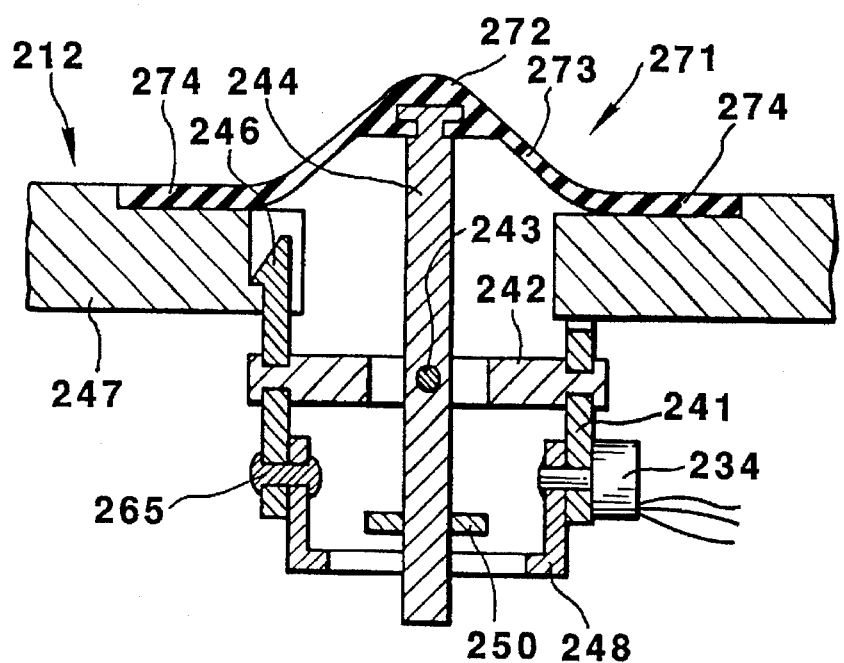
FIG. 85 is a cross-sectioned view showing the formation of a curvature switch in the modification of the ninth embodiment of the present invention.

FIG. 85 is a cross-sectioned view showing the formation of a curving switch 271 in the modification of the ninth embodiment of the present invention.

This curving switch 271 is a modification of the curving switch 222 of the ninth embodiment wherein the elastic force of a water-proof rubber cover is used instead of returning the operating lever to the central position by the elastic force of the compression spring.

The same as in the sixth embodiment, when a pawl of an arm 246 provided in the upper part of the casing 241 is engaged with an incision of the casing 247 of the operating section 212, the curving switch 271 will fixed to the operating section 212. A rubber cover 272 is integrally fitted to the head part of the operating lever 244, has an all peripheral foot part 273, is water-tightly secured at the end 274 to the casing 247 of the operating section 212 and is waterproofed. When the operating lever 244 is in the central position, the foot part 273 of this rubber cover 272 will not be loose. The other formations are the same as in the ninth embodiment. The same components shall bear the same reference numerals and shall not be explained here.

When the operating lever 244 of the curving switch 271 is tilted the same as in the ninth embodiment, the rotors 248 and 250 will rotate, the resistance values of the variable resistors 234 and 235 will vary, the curving motors 229 and 230 will be driven and the curvature section 220 will curve in a curvature angle proportional to the tilting angle of the operating lever 244. At this time, when the operating lever 244 falls, the foot part 273 of the rubber cover 272 on the side opposite the falling direction will extend. In this state, when the finger is released from the operating lever 244, the foot part 273 of the rubber cover 272 will tend to return to the original state due to the elastic force and therefore the operating lever 244 will be returned to the central position.

Thus, in this embodiment, as the rubber cover 272 is simultaneously a water-proofing means and operating lever 244 returning means, the curving switch 271 will be able to be compactly formed in a simpler formation, the insertable section tip will be able to be easily made straight when this curving switch 271 is not operated and the operation will be able to be easily instructed so that the curvature section may be curved as desired.

The other operations and effects are the same as in the ninth embodiment.

Figure 86:
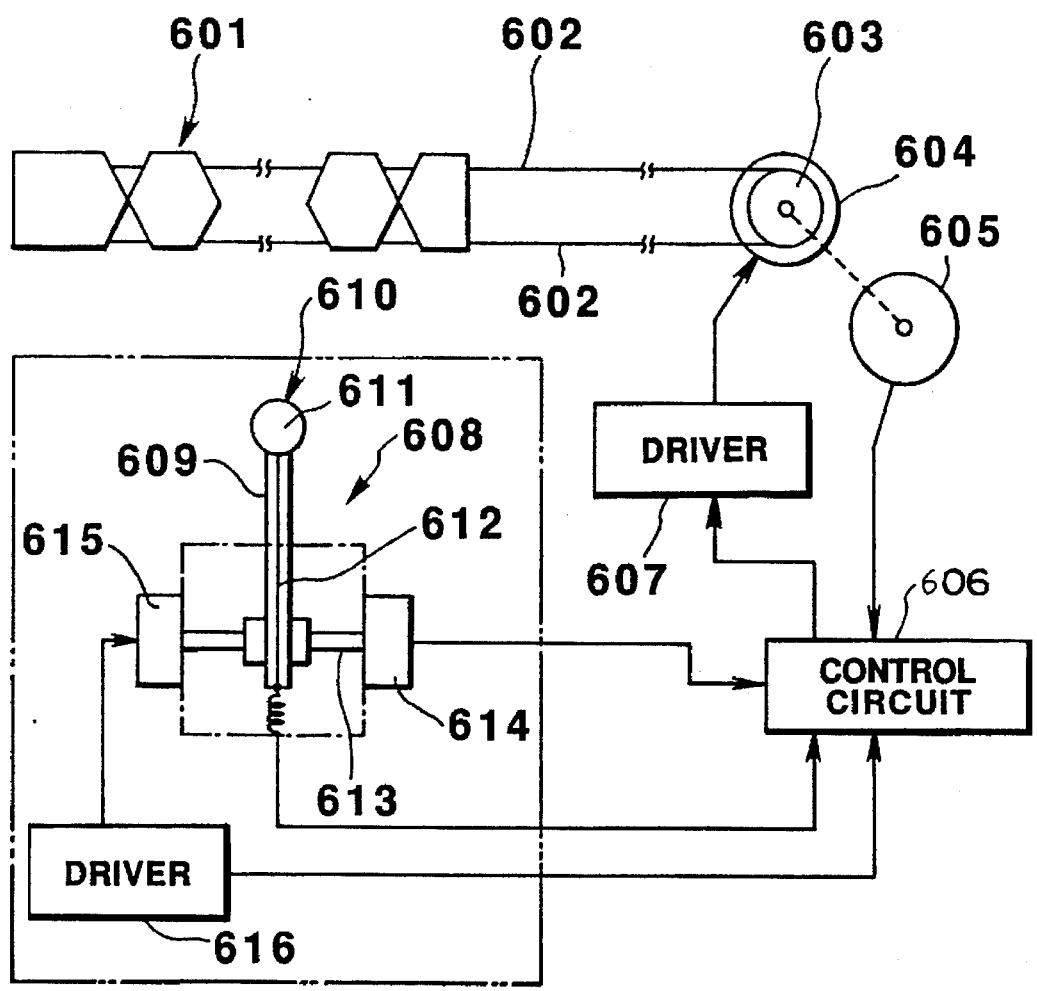
FIGS. 86 to 87 relate to the tenth embodiment of the present invention.

FIG. 86 shows the schematic formation of the curving apparatus in the 10th embodiment of the present invention.

In the 10th embodiment, when the operating finger is released from the curving operating switch, the curvature section will be curved in the straight direction.

The curvature section 601 provided in the insertable section of the endoscope is formed by connecting a plurality of curved pieces so as to be curvable in the vertical and horizontal directions. By the way, in the following, for the sake of brevity, only the case of curving in the vertical direction (UP/DN direction) shall be illustrated and explained. However, the case of the horizontal direction is also the same.

A curving wire 602 pulling and curving the above mentioned curvature section 601 is inserted through the curvature section 601, is fixed at one end to the tip of the curvature section 601 and is wound at the other end around a pulley 603 which is secured to the rotary shaft of a curving motor 604, is rotated by the drive of the motor 604 and pulls and relaxes the curving wire 602. A curvature angle coaxially detecting potentiometer 605 is secured to the rotary shaft of the curving motor 604 to defect the curvature angle of the curvature section 601.

The output of the potentiometer 605 is to be input into a controlling circuit 606 controlling the curving operation of the curvature section 601. The controlling circuit 606 controls a driver 607 driving the driver 607 driving the motor 604 in response to the detected curvature angle or the like.

That is to say, a driving signal is output from the controlling circuit 606 to the driver 607 and the curving motor 604 rotates in the vertical direction or stops by the instruction of the controlling circuit 606.

The operating section of the endoscope is provided with a joy stick 608 as a curving instructing apparatus. A finger touch part 610 is provided at the end of an operating lever 609 of this joy stick 608. The finger touch part 610 is provided with a touch sensor 611 the same as in the finger touch surface of 241 of the curving switch in the eighth embodiment to detect whether the operating finger or the like is in contact or not. The output of the touch sensor 611 is input into the controlling circuit 606 through a signal line 612 inserted through the operating lever 609.

A rotary shaft 613 to which the operating lever 609 is pivoted is provided respectively at both ends with a potentiometer 614 detecting the displacement of the operating lever 609 and a lever driving motor 615 driving the rotary shaft 613. The operating lever 609 is fitted rotatably in the direction vertical to the paper surface with this rotary shaft 613 as a center.

The output of the potentiometer 614 is input into the above mentioned controlling circuit 606. The controlling circuit 606 controls a driver 616 driving the motor 615 in response to the position or the like of the operating lever 609.

That is to say, a driving signal is output to the driver 616 from the controlling circuit 606 and the lever driving motor 615 rotates or stops according to the instruction of the controlling circuit 606.

Figure 87:
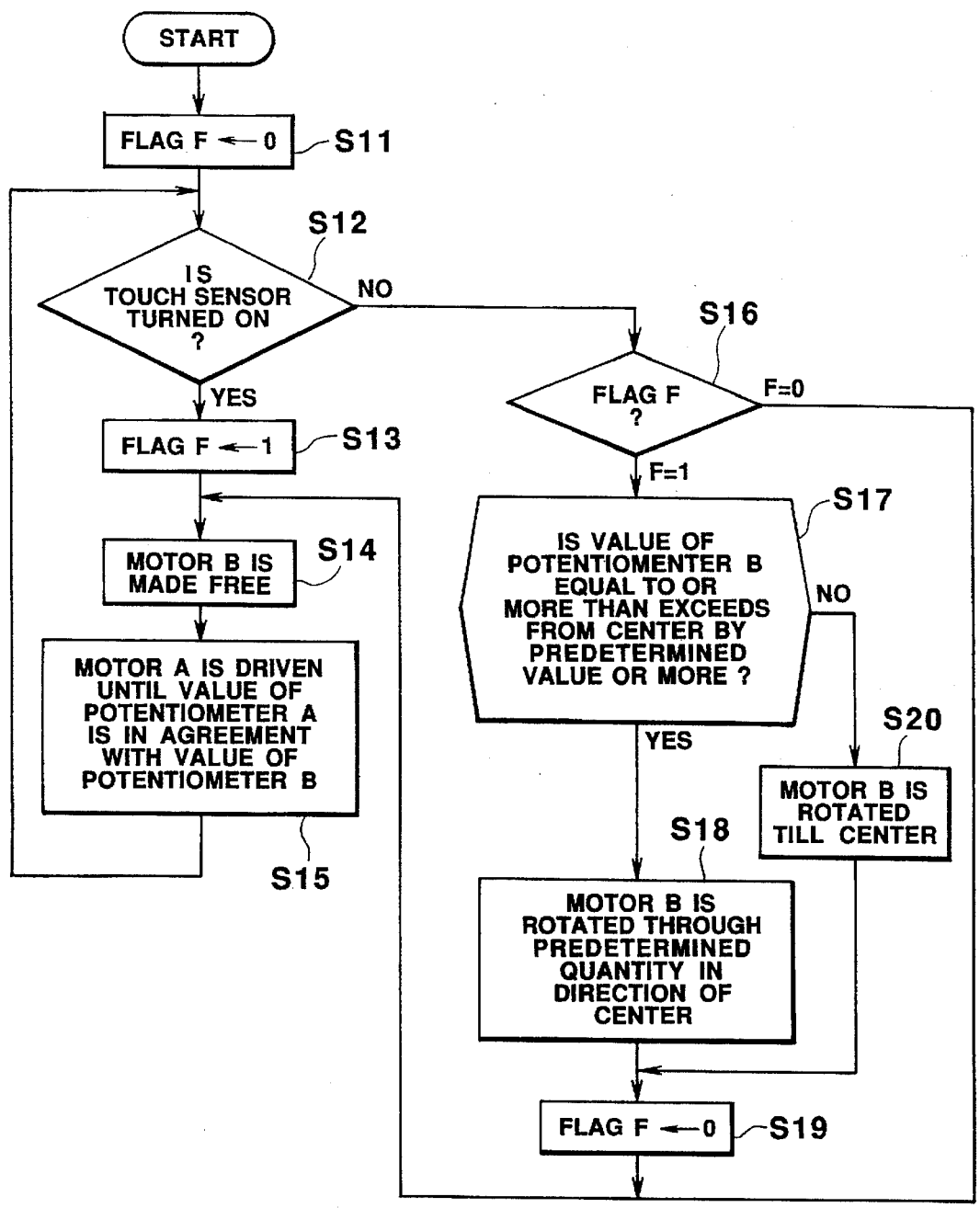

The operation of the curving apparatus of this embodiment shall be explained in the following with reference to FIG. 87. The flow chart of FIG. 87 shows the operation mostly in the controlling circuit 606.

When the power source of the curving apparatus is engaged, first in S11, a flag F showing the operating state of the joy stick 608 will be set at 0. Then, in S12, it is judged whether the touch sensor 611 provided on the operating lever of the joy stick 608 is on/off.

Here, in case the touch sensor 611 is on, that is to say, the operating finger is in contact with the finger touch part 610 of the operating lever 609, the process will proceed to S13 and the flag F will be set at and, in S14, the lever driving motor 615 will be made free and the joy stick 608 will become freely inclinable.

When the curving operation is instructed in this state and the operating lever 609 of the joy stick 608 is inclined, the output value of the potentiometer 614 within the joy stick 608 will vary and therefore a difference from the output value of the curvature angle detecting potentiometer 605 will be produced.

Then, in S15, the controlling circuit 606 will output a driving signal to the driver 607 until the output value of the potentiometer 605 coincides with the output value of the potentiometer 614 and will drive the curving motor 604. Thereby, the curvature angle of the curvature section 601 will be determined in response to the inclining angle of the joy stick 608 and the curvature section will be curved to be of this curvature angle. By the way, in S15, in response to the difference between the value of the potentiometer 605 and the value of the potentiometer 614, for example, the larger the difference, the larger the driving power fed to the curving motor 604. Then, the process will return to S12 from S15 and will be continued.

After the joy stick 608 is operated, when the finger is released from the finger touch part of the operating lever 609, the touch sensor 611 will detect it and will become off. In this case, the process will proceed to S16 from S12 and the flag F will be judged. Just after the joy stick 608 is operated, the flag F=1. Therefore, the process will proceed to S17 and the value of the potentiometer 614 will be judged. Here, from the value when the curvature section 601 is straight (it shall be a center hereinafter), a predetermined value, for example, whether the curvature angle is above 30 degrees or not will be judged.

Here, in case the value is above a predetermined value, the process will proceed to S18 and the lever driving motor 615 will be rotated by the predetermined value, for example, 30 degrees in the curvature angle in the center direction. Thereby, the operating lever 609 of the joy stick 608 will be driven by the predetermined value in the center direction. Then, in S19, the flag F will be set at 0 and the process will proceed to S14.

In S14 and S15, the controlling circuit 606 will free the lever driving motor 615 the same as in the above and will drive the curving motor 604 until the value of the potentiometer 605 coincides with the value of the potentiometer 614. Thereby, the curvature section 601 will be curved and driven by a predetermined angle in the center direction (straight direction).

In S17, in case the value of the potentiometer 614 is below a predetermined value, for example, below 30 degrees in the curvature angle, the process will proceed to S20 and the lever driving motor 615 will be rotated to the center position.

That is to say, the operating lever 609 of the joy stick 608 will be in the center position. Then, the same as in the above, in S19, the flag F will be set at 0, S14 and S15 will be carried out, the lever driving motor 615 will be made free and the curving motor 604 will be driven until the value of the potentiometer 605 coincides with the value of the potentiometer 614. Thereby, the curvature section 601 will be curved and driven to the center position (straight position).

After the curvature section is curved and driven in the center direction, the process will return to S12 and will be continued, the flag F=0 will be maintained until the touch sensor 611 becomes on and the processes of S16 to S14 and S15 will be repeated.

As in the above, in this embodiment, when the joy stick 608 is inclined and operate and then the operating finger is released from the finger touch part 610, the curvature section will return by a predetermined value in the straight direction and therefore the operator will be able to easily confirm the straight direction.

When the finger is released from the operating lever 609 of the joy stick 608, the operating lever 609 and curvature section 601 will naturally return in the straight direction, therefore this operation will be favorable to the technique of inserting a large intestine endoscope into a large intestine and the endoscope will be able to be easily inserted at a high operability.

Even in the case of such danger that, when the finger is released from the joy stick 608, the curvature section will return to the straight position, when the curvature section is made to return by a predetermined angle in the straight direction as in this embodiment, the operation will be able to be easily made while keeping the safety.

On the other hand, when the finger is not released from the operating lever 609 but is retained, the present curvature angle will be able to be maintained.

Even when the finger is released from the joy stick 608 and the curvature section 601 returns in the straight direction, as the inclining angle of the joy stick 608 and the curvature angle of the curvature section 601 always coincide with each other, the operability will be high.

Figure 88:
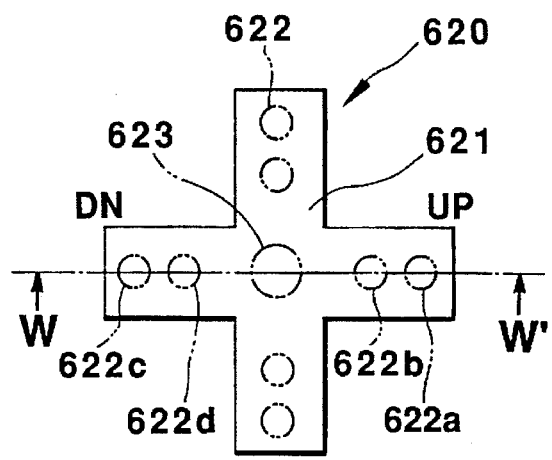
FIGS. 88 to 91 relate to the eleventh embodiment of the present invention, FIG. 88 being a plan view showing the formation of a curvature operating switch.

FIG. 88 is a plan view showing the formation of a curving operating switch in the modification of the 10th embodiment of the present invention.

Instead of the joy stick 608, lever driving motor 615, potentiometer 614 and driver 616 of the 10th embodiment shown in FIG. 86, in this modification, a curving operating switch 620 formed of a 4-direction 2-step on/off switch shown in FIG. 88 is provided and is connected to a controlling circuit 606.

By the way, for the sake of brevity, only the case of curving the curvature section in the vertical direction (UP/DN direction) shall be explained in the following but the explanation shall be the same on the horizontal direction.

Figure 89:
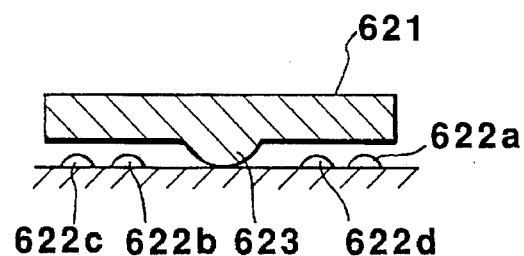

A curving operating switch 620 is formed of two contacts 622 each formed of an arcuate plate spring click plate arranged in each direction totaling 8 contacts below the same cross pad 621 as in the eighth embodiment. FIG. 89 is a cross-sectioned view of the curving operating switch 620 in which the contacts 622a and 622b in the upward direction (UP direction) and the contacts 622c and 622d in the downward direction (DN direction) are provided respectively as opposed to the pad 621.

When the pad 621 tilts, these click plate contacts 622 will be crushed to be flat plate-like and will be on as in contact with the substrate.

Figure 90:
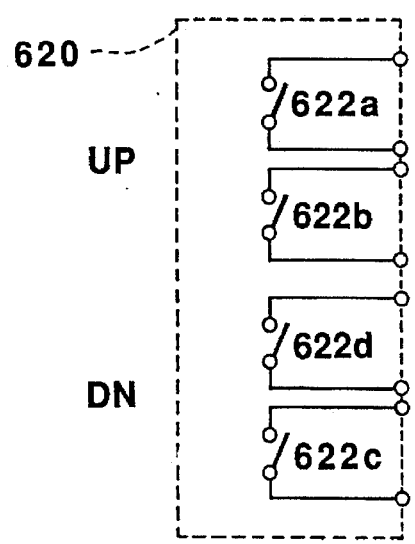

That is to say, as shown in FIG. 90, the curving operating switch 620 is formed of two on/off switches in each direction. An on/off signal showing the on/off states of the contacts 622a and 622b in the UP direction and the contacts 622c and 622d in the DN direction is to be input into the controlling circuit 606.

A hemispherical projection 623 is provided below the center part of the pad 621 so that the pad 621 may be tiltable with this projection 623 as a center. When the pad 621 is tilted, for example, in the UP direction, first the contact 622a will be crushed to be on. When the pad 621 is further tilted from this state, not only the contact 622a but also the contact 622b will be crushed to be on.

That is to say, the curving operating switch 620 is a multi-step switch which will be on in two steps in response to the operating amount of the pad 621. Thus, when a plurality of contacts are arranged in the projection direction of the cross pad, a small multi-step switch high in the click sense will be able to be formed. By the way, the description shall be the same also on the DN direction.

Figure 91:
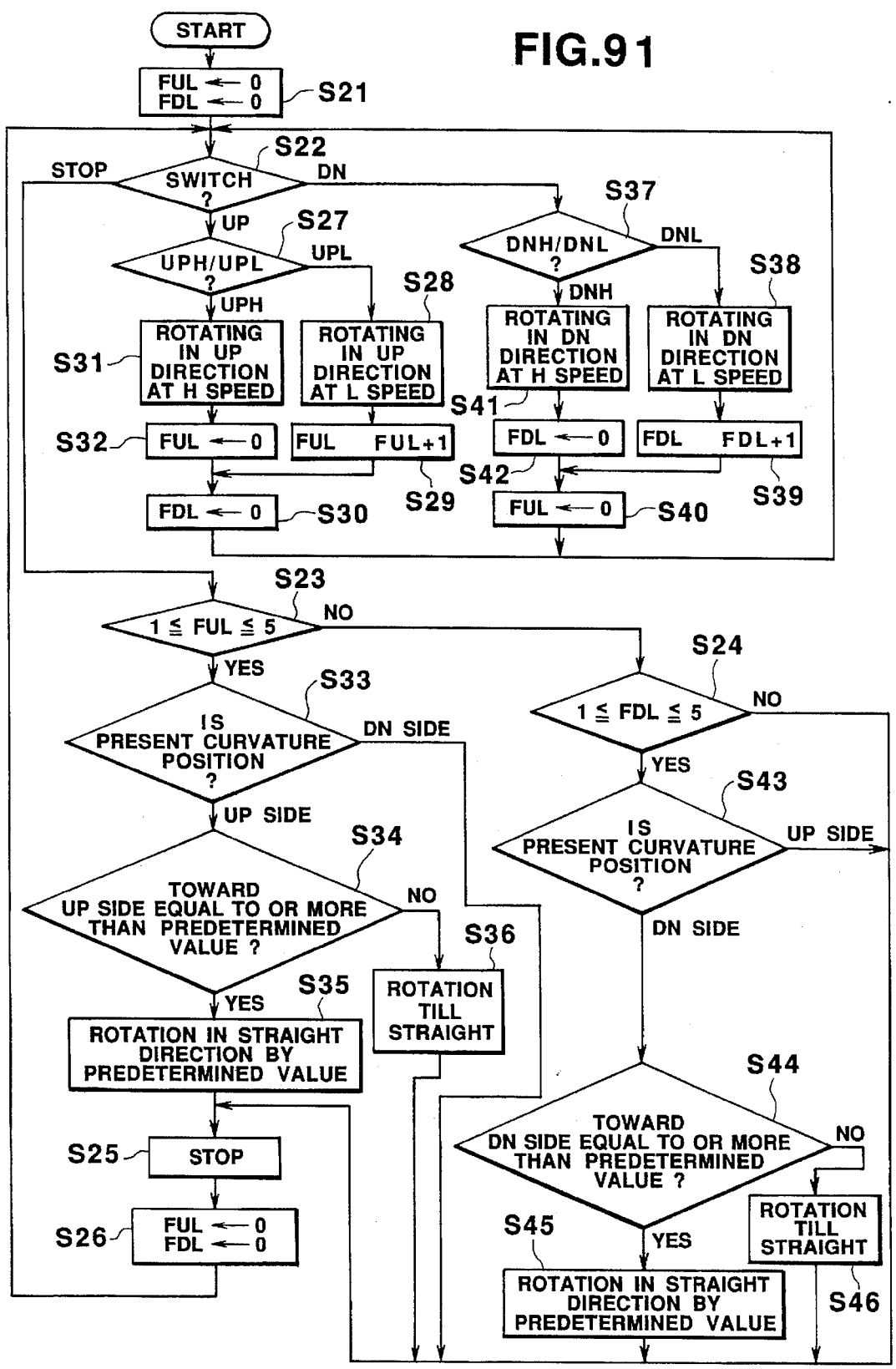

Now, the operation of the curving apparatus of this embodiment shall be explained with reference to FIG. 91. The flow chart of FIG. 91 shows the operation mostly of the controlling circuit 606.

When the power source of the curving apparatus is engaged, first in S21, flags FUL and FDL showing the operating states of the curving operating switch 620 will be respectively set at FUL=0 and FDL=0. Then, in S22, the state of the curving operating switch 220 will be judged.

When the curving operating switch 620 is not operated, the contacts 622a to 622d will be all off and therefore will be judged to stop and the process will proceed to S23. In S23, whether the value of FUL is 1≦FUL≦5 will be judged. In the case of no, the process will proceed to S24 and whether the value of FDL is 1≦FUL≦5 will be judged.

At this time, as FUL=0 and FDL=0, the process will proceed to S25 and a stopping signal will be output to the driver 607. The process will return to S22 through S26. That is to say, when the curving operating switch 220 is not operated, the curving motor A204 will remain stopped.

When the pad 621 of the curving operating switch 620 is a little tilted in the UP direction, first the contact 622a will be on. Then, in S22, the controlling circuit 606 will judge it to be a UP direction curving instruction. The process will proceed to S27 and whether the curving instruction is a low speed curving instruction (UPL) or a high speed curving instruction (UPH) will be judged.

Here, as the pad 621 is a little tilted in the UP direction and only the contact 622a is on, it will be judged to be a low speed curving instruction and the process will proceed to S28. In S28, the driver 607 will be driven to rotate the curving motor 604 in the UP direction at a low speed (L speed). Then, in S29, the flag FUL will be made FUL←FUL+1. That is to say, FUL=1. Further, in S30, the flag FDL will be set at 0. The process will return to S22.

If the contact 622a remains on, S27 to S30 will be repeated. That is to say, the curvature section will be further curved in the UP direction at a low speed, the FUL will be added by 1 each time so as to be soon FUL>5.

In this state, when the finger is released from the pad 621 of the curving operating switch 620, the contacts 622a to 622d will be all off. Therefore, in S22, it will be judged to be a stopping instruction. The process will proceed to S23 and the value of the FUL will be judged. Here, as FUL>5, then in S24, the value of the FDL will be judged. As FDL=0, the process will proceed to S25 and a stopping signal will be output to the driver 607 and the curving motor 604 will be stopped. Then, in S26, FUL=0 and FDL=0 will be respectively set. The process will return to S22.

Thus, in case only the contact 622a is on and the low speed curving is instructed, the curvature section will be curved and driven at a low speed and, as soon as the finger is released from the curving operating switch 620, the curving will stop.

When the pad 621 of the curving operating switch 620 is largely inclined in the UP direction, the contacts 622a and 622b will be both on. Then, in S22, the controlling circuit 606 will judge it to be a UP direction curving instruction. The process will proceed to S27. Whether the curving instruction is a low speed curving instruction (UPL) or a high speed curving instruction (UPH) will be judged.

Here, as the contacts 622a and 622b are on, it will be judged to be a high speed curving instruction. The process will proceed to S31. In S31, the driver 607 will be driven to rotate the curving motor 604 in the UP direction at a high speed (H speed). In S32, the flag FUL=0 will be set. Further, in S30, the flag FDL=0 will be set. The process will return to S22.

In this state, when the finger is released from the pad 621 of the curving operating switch 620, first the contact 622b will be off and then the contact 622a will be on for a moment, the process will proceed to S27 to S30 and FUL←FUL+1 will be carried out but, as it is for a moment, FUL>5 will not be made by going round a loop several times.

Thereafter, the contacts 622a and 622b will be both off. In S22, it will be judged to be a stopping instruction. In S23, the value of the FUL will be judged. By the way, the period of the judgment of the state of the curving operating switch 620 in S22 and the range (1 to 5) of the values of the FUL and FDL judged in S23 and S24 can be freely set in response to the using state or the like.

At this time, as 1≦FUL≦5, the process will proceed to S33 and the present curving position will be judged. Here, in the case of curving to the UP side, the process will proceed to S34 and further whether the curving angle above a predetermined value is on the UP side or not will be judged. By the way, the same as in the 10th embodiment, this predetermined value may be, for example, 30 degrees in the curving angle.

In the case of curving on the UP side above a predetermined value, the process will proceed to S35, the curving motor 604 will be rotated in the straight direction by the predetermined value and, in case the curving angle is below the predetermined value, the process will proceed to S36 and the curving motor 604 will be rotated until the curvature section is in the straight position. In S25, a stopping signal will be output to the driver 607 and a curving motor 604 will be stopped.

By the way, in S33, in case the present curving position is on the DN side, the process will proceed to S25 and immediately the curving motor 604 will be stopped. Then, in S26, FUL=0 and FDL=0 will be respectively set. The process will return to S22.

Therefore, in case the pad 621 of the curving operating switch 620 is largely inclined to instruct a high speed curving, the curvature section is curved in the UP direction at a high speed and then, in the curving position in the UP direction, the finger is released from the curving operating switch 620 and the curving instruction is stopped, the curvature section will be curved and driven by a predetermined value in the straight direction (the DN direction in this case) or to the straight position in response to the curving angle.

By the way, even in case the curving is instructed in the DN direction, in S37 to S46, the curvature section will be curved and controlled substantially the same as in the case of the UP direction and therefore the explanation shall be omitted.

By the way, the curvature section driving means may be a driving means using a shape memorizing alloy or fluid pressure instead of the motor.

The curvature section curving directions are not limited to four directions but may be two directions.

The endoscope used in the present invention may be either of an electronic scope provided with a solid state imaging device or a fiber scope provided with an image guide.

The endoscope apparatus of the present invention can be applied to not only a medical endoscope but also an industrial endoscope.

Further, the curvature section driving means may be provided anywhere within the operating section, within the connector of the universal cord or outside the endoscope.

The respective embodiments of the curving operating switch by which the neutral position can be recognized shall be explained in turn in FIGS. 92 to 98 in the following.

Figure 92A:
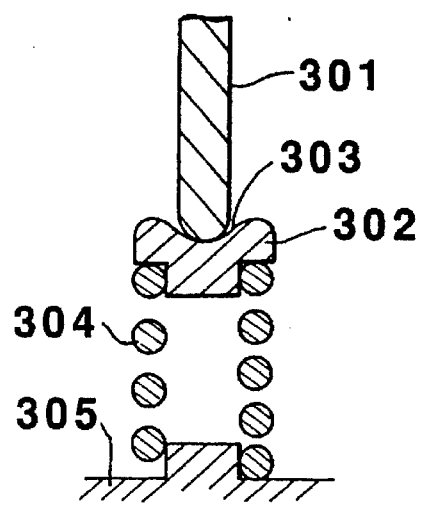
FIG. 92 is an explanatory view showing an essential portion of a mechanism in which the neutral position can be recognized.

In FIG. 92, a stick 301 inclines with the center point (not illustrated) in four directions of a joy stick as a center. The stick 301 of the type of this embodiment does not vertically move. At the neutral point (in the state of FIG. 92a), the stick 301 fits in a recess 303 on the upper surface of a neutral supporting member 302. The neutral supporting member 302 is rockably fixed to the joy stick body bottom 305 by a spring 304. The operation shall be explained in the following.

Figure 92B:
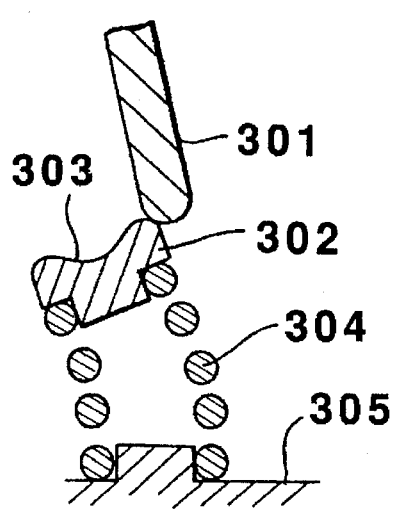

When the stick 301 is inclined, it will deviate from the recess 303 to be in the state of FIG. 92b. When the stick 301 is further inclined, the neutral supporting member 302 will be returned to the neutral state in FIG. 92a by the force of the spring 304. In this state, the stick 301 will not touch the neutral supporting member 302, therefore its touch will not be transmitted to the stick 301 and the stick 301 will not be found to be nearly neutral.

When the stick 301 touches the neutral supporting member 302, the touch will be transmitted to the stick 301. By the way, the spring 304 is so selected that, when the stick 301 becomes completely neutral, it will fit in the recess 303. According to this structure, there is an effect that the neutral vicinity can be recognized.

In FIG. 93, the stick 311 is movable in the axial direction so that a first position 312 and second position 313 shown respectively by two-point chain lines may be selectable. The spring 315 is fixed at one end to the joy stick body bottom 314 and has at the other end a neutral energizing member 316 fixed.

Figure 93A:
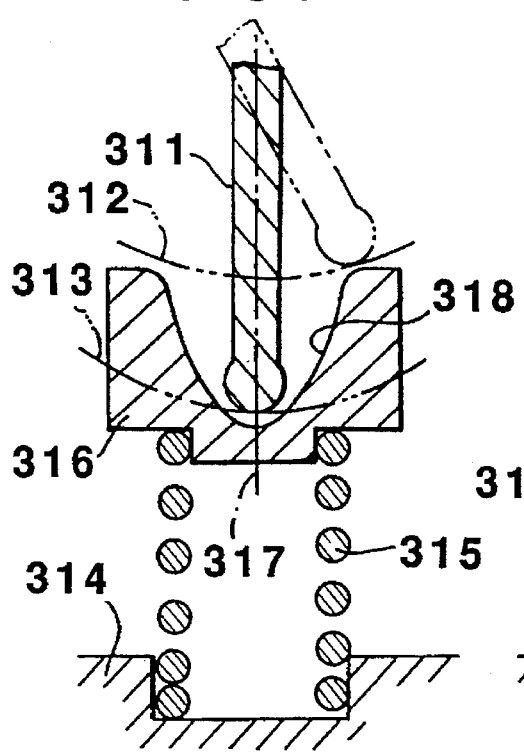
FIGS. 93 to 98 are explanatory views showing an essential portion of a mechanism in which the presence and absence of the neutral return can be switched to each other.

The neutral energizing member 316 is provided on the inside surface with a cam surface 318 symmetrical in any direction to the center line 317 in the position relation in FIG. 93a. The operation shall be explained in the following.

Figure 93B:
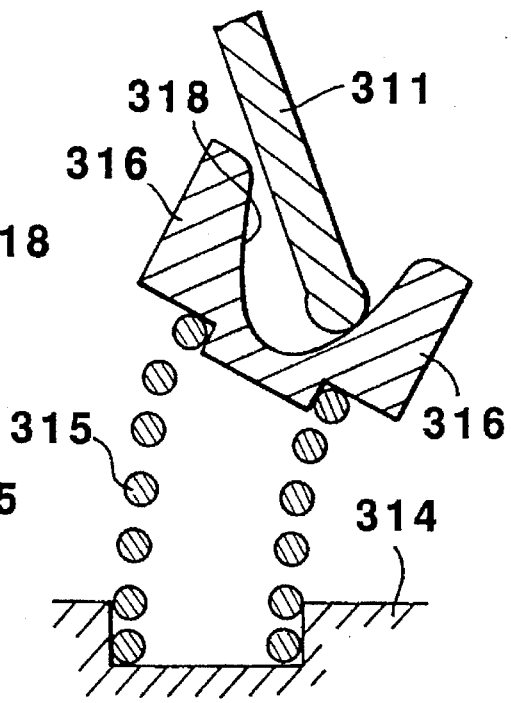

In the second position 313 in FIG. 93a, even if the state 311 inclines, it will never contact the neutral energizing member 316. Therefore, even if the hand is released from the stick 311, the inclination angle will be held. In the first position 312 in FIG. 93a, when the stick 311 is inclined, as shown in FIG. 93b, the stick 311 will contact the cam surface 318.

In this state, when the hand is released from the stick 311, the stick 311 will become neutral as in FIG. 93a due to the energizing force of the spring 315. This structure has an effect that the presence and absence of the neutral return can be switched over to each other.

In FIG. 94, a stick 321 comprises an outer cylinder 322 and an inner bar 323 and the inner bar 323 forming a pressing member is free to project out of and submerge into the outer cylinder 322. This inner bar 323 is provided with a stopper screw 325 so that the inner bar 323 may not be excessively pulled into the outer cylinder 322.

A neutral energizing member 326 is to be fitted to the lower part of the outer cylinder 322 and is rockably fixed to a joy stick body 328 by a spring 327. The operation shall be explained in the following.

The operation of the neutral return shall be explained with reference to FIGS. 94a and 94b. When the stick 321 is inclined, the state in FIG. 94b will be made. Here, when the hand is released from the stick 321, by the energizing force of the spring 327, the stick 321 will be neutrally returned to the state in FIG. 94a.

Figure 94A:
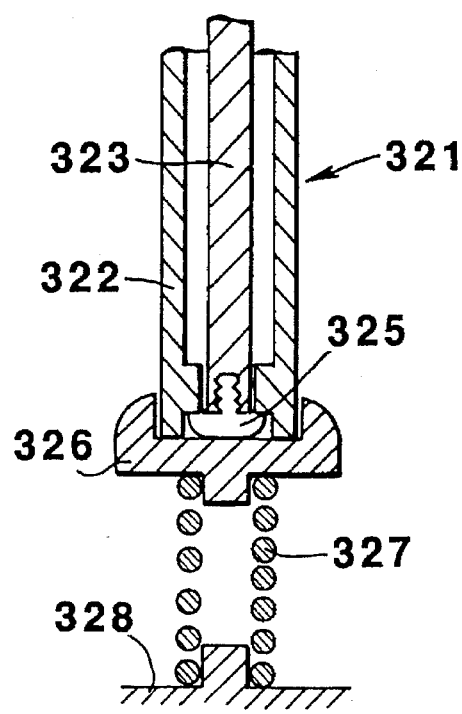
Figure 94B:
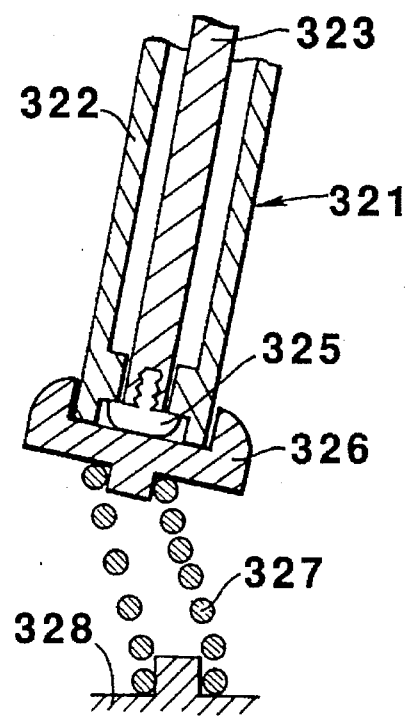
Figure 94C:
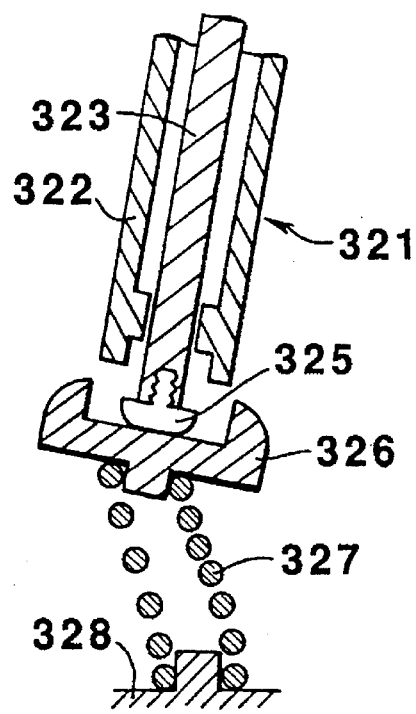
Figure 94D:
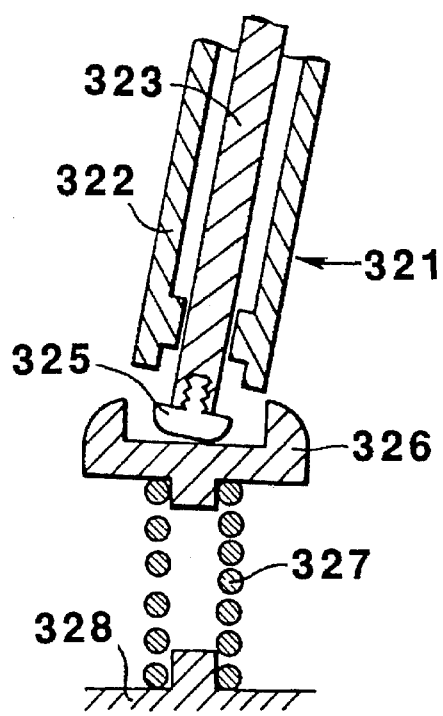

When the stick 321 is inclined to be in the state in FIG. 94b, if the outer cylinder 322 is slid upward as shown in FIG. 94c, the outer cylinder 322 and neutral energizing member 326 will be disengaged with each other and, as a result, the state shown in FIG. 94d will be made by the energizing force of the spring 327. Here, even if the hand is released from the stick 321, as shown in FIG. 94d, the stick 321 will be held as inclined.

Then, if the outer cylinder 322 is slid downward, as shown in FIG. 94a, the outer cylinder 322 and the neutral energizing member 326 will be engaged with each other and will neutrally return. By the way, if the outer cylinder 322 is first slid upward and then the stick 321 is inclined, the stick 321 will be held as inclined the same as in the above.

In FIG. 95, a stick 331 comprises an outer cylinder 332 and a pressing bar 333 which is free to project out of and submerge into the outer cylinder 322 and is engaged and fixed at the lower end in a recess on the upper surface of a neutral energizing member 334.

This neutral energizing member 334 is fixed to a joy stick body 336 by a spring 335. The operation shall be explained in the following.

Figure 95A:
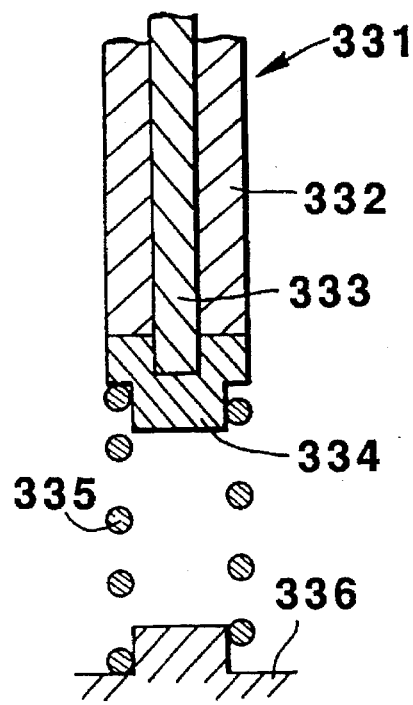

The case of no neutral return, that is, the case that the stick 331 is held as inclined shall be explained with reference to FIG. 95a. In the state of FIG. 95a, as the spring 335 is insufficient for the energizing force to make the neutral return, when the stick 331 is inclined, it will be held as inclined.

Figure 95B:
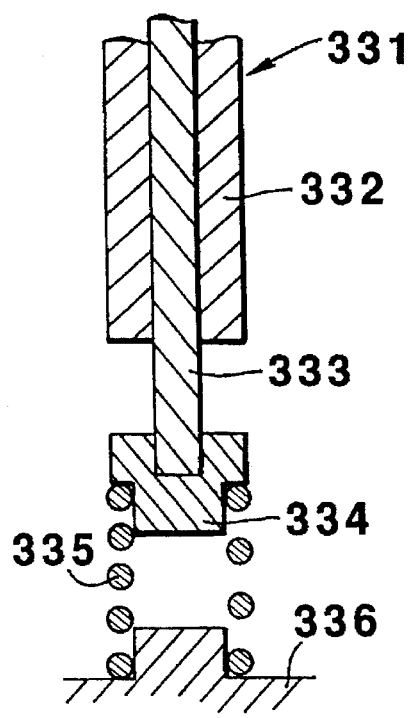

The case of a neutral return shall be explained with reference to FIG. 95b. When the pressing bar 333 is selected as projected out of the outer cylinder 332, the spring 335 will generate an energizing force required for the neutral return and therefore the stick will be neutrally returned.

Figure 96:
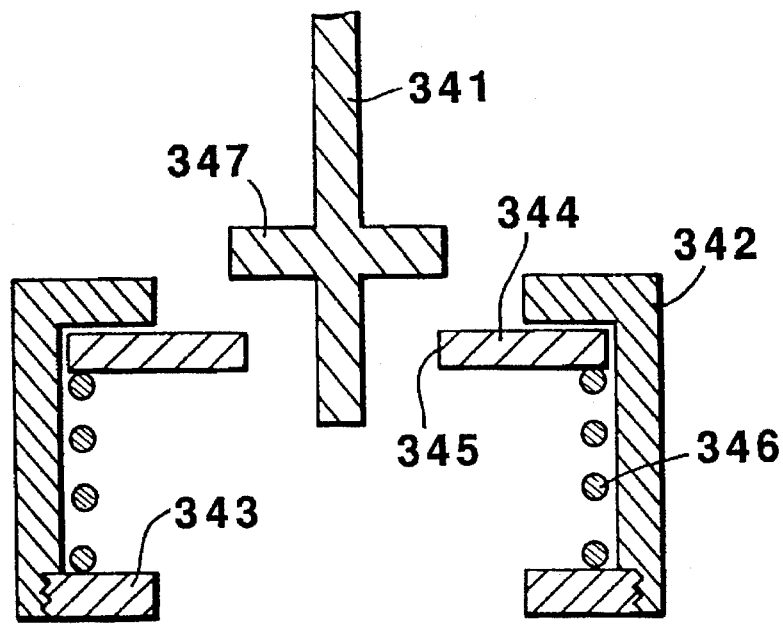

In FIG. 96, the stick 341 is slidable in the axial direction. A lid 343 is screwed in the lower part of a columnar casing 342 which is provided within it with a circular plate 344 provided in the center with a hole 345. This plate 344 is upward energized by a spring 346.

The stick 341 is provided in the lower part with a disk 347 of a diameter larger than of the hole 345 of the plate 344. The operation shall be explained in the following.

In the state in FIG. 96, when the stick 341 is inclined and the hand is released from the stick 341, the stick will be held as inclined. When the stick 341 is inclined and then is no longer wanted to be neutrally returned, the stick 341 will be slid, the disk 347 will be pressed against the plate 344 and the hand will be released. Then, the stick 341 will neutrally return due to the energizing force of the spring 346.

Figure 97:
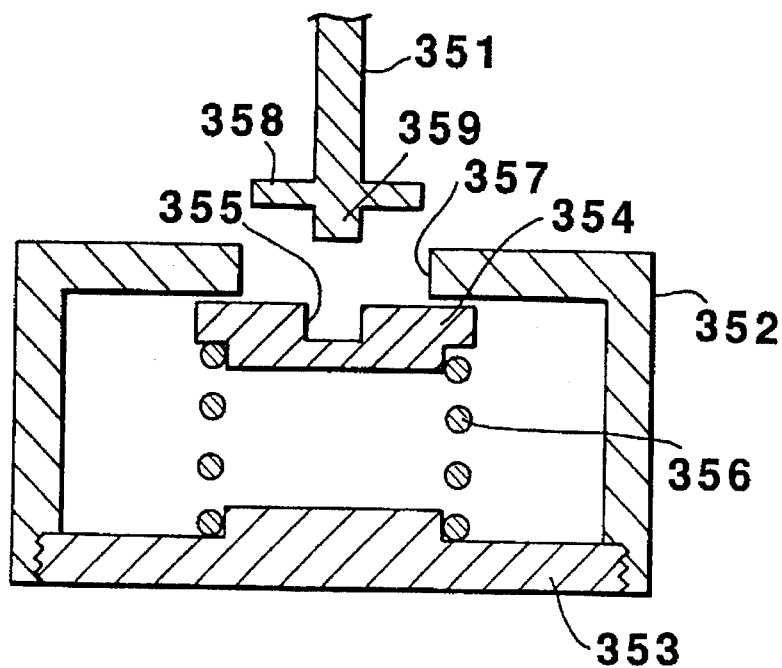

In FIG. 97, a stick 351 is slidable in the axial direction. A lid 353 is screwed in the lower part of a columnar casing 352. The casing 352 is provided within it with a circular plate 354 provided in the center with a hole (or recess) and energized upward by a spring 356.

The stick 351 is provided in the lower part with a flange 358 of a diameter smaller than of a hole 357 provided on the upper surface of the casing 352. A projection 359 in the lower part of this stick 351 fits in the above mentioned hole 355. The operation shall be explained in the following.

In the state in FIG. 97, when the stick 351 is inclined and the hand is released from the stick 351, the stick 351 will be held as inclined. When the stick 351 is inclined and is then slid downward, the stick 351 will contact in the lower part with the upper surface of the casing 352 and will not neutrally return.

In order to neutrally return, the stick 351 must be in the neutral state and must be slid downward, the projection 359 must engage with the hole 355 and the stick 351 must be slid by more than the thickness of the flange 358 and then must be inclined.

Figure 98:
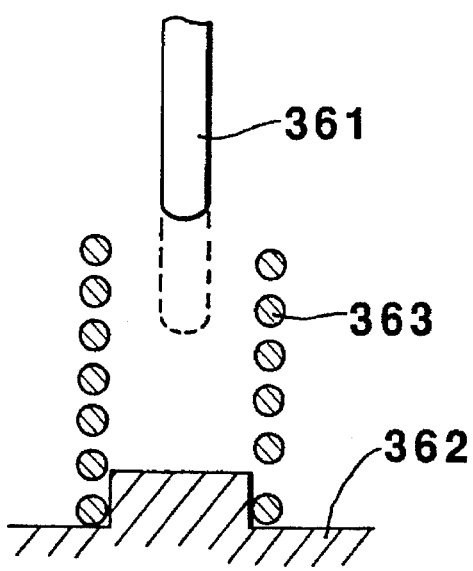

In FIG. 98, the stick 361 is slidable in the axial direction and a spring 363 is fixed to the joy stick body lower surface 362. The operation shall be explained in the following.

In the solid line state of the stick 361 in FIG. 98, when the stick 361 is inclined, it will be held as inclined even if the hand is released. In the broken line state of the stick 361 in FIG. 98, when the stick 361 is inclined, if the hand is released, the stick will neutrally return.

By the way, for example, in the first embodiment, in case the operating lever 33 is tilted, the tilting angle will be detected from the resistance values of the variable resistors (potentiometers) 34 and 35. However, in case the resistance values can be memorized in a memory or the like and the operating lever is returned to the neutral position, the same tilting angle may be again set by reading out the later memorized resistance values.

By the way, the position to which the operating lever is operated to return is not limited to the neutral position but may be any other position. Also, the position to which the operating lever is returned may be variably set.

By the way, the present invention is not limited to the above described respective embodiments and an embodiment formed by modifying a part of another embodiment or by combining a part of different embodiments belongs to the present invention.

What is claimed is:

1. An endoscope apparatus comprising:
    an endoscope provided with an elongate insertable section insertable into a body cavity and having a curvable curvature section, an objective optical system provided at a distal end of said insertable section and forming an optical image, and illuminating light emitting means emitting illuminating light from a distal end of said insertable section;
    a curving switch performing operation for indicating curving amount of said curvature section;
    driving force generating means for generating a driving force for curving said curvature section in response to the operation of said curving switch;
    driving force transmitting means, inserted into said insertable section, for transmitting said driving force to said curvature section;
    a change-over switch switching between at least a first mode and a second mode at an indicating position of said curving switch; and
    control means for controlling said driving force generating means in accordance with operation of said change-over switch so as to switch between said first mode for controlling a curving angle in a decreasing direction without maintaining a curving state of said curvature section at the time of cancelling said operation of said curving switch and said second mode for maintaining said curving state of said curvature section.

2. An endoscope apparatus according to claim 1 wherein said curving switch has a tiltable lever, and further comprising an indicating amount detecting means for detecting said lever inclining direction and inclination angle, and wherein said indicating amount detecting means outputs an indicating signal representing a curving direction and curving angle of said curvature section.

3. An endoscope apparatus according to claim 2, wherein said indicating amount detecting means is arranged on a base end side of said lever and includes a potentiometer in which a resistance value varies in response to said inclination angle of said lever.

4. An endoscope apparatus according to claim 2 wherein said control means changes said indicating amount upon change in the inclination angle of said lever caused by actuation of said change-over switch on the basis of an operated signal.

5. An endoscope apparatus according to claim 4 wherein an indicating amount corresponding to the change of the inclination angle of said lever is output to said driving force generating means and the curvature angle of said curvature section is changed.

6. An endoscope apparatus according to claim 2, further comprising return force means for returning said lever to a neutral position and a returning force changing member which can change the value of said returning force in which said inclination angle of said lever is zero, and wherein said change-over switch generates a change signal indicating said change of the value of said returning force.

7. An endoscope apparatus according to claim 6 wherein, when said change signal is received by said control means, said control means will cause said returning force to be increased and will thereby cause return of said lever to said neutral position.

8. An endoscope apparatus according to claim 6, wherein said returning force changing member is composed of a shape memorizing alloy varying the value of the returning force by a phase transformation and wherein, when said change signal is received, said control means heats said returning force changing member to increase the value of said returning force and thereby cause return of said lever to said neutral position.

9. An endoscope apparatus according to claim 6, wherein said change-over switch is disposed at a top portion of said lever.

10. An endoscope apparatus according to claim 1, further comprising a displaying means for displaying of said first mode or second mode in response to the operation of said change-over switch.

11. An endoscope apparatus according to claim 1, wherein said driving force generating means includes a motor for pulling said driving force transmitting means when said motor is rotated.

12. An endoscope apparatus according to claim 11 wherein is provided a curvature angle detecting means detecting the curvature angle of said curvature section by detecting the rotation amount of said motor.

13. An endoscope apparatus according to claim 1 wherein, case said change-over switch is operated, said control means will change the instructing mount of said curving switch and will control said curvature section to be of a curvature angle corresponding to the changed instructing amount.

14. An endoscope apparatus according to claim 1 wherein said curving switch has a plurality of on/off switches provided to correspond to the direction of curving said curvature section.

15. An endoscope apparatus according to claim 14 wherein is provided an instructing signal generating means generating an instructing signal curving said curvature section by a curvature angle proportional to the time when said on/off switches are on.

16. An endoscope apparatus according to claim 15 wherein said instructing signal generating means has an integrating circuit generating a voltage proportional to the time when said on/off switches are on.

17. An endoscope apparatus according to claim 15 wherein said controlling means holds/resets the instructing signal of said instructing signal generating means in response to the operation of said change-over switch.

18. An endoscope apparatus according to claim 15 wherein said curving switch is formed of a joy pad provided with a plurality of on/off switches provided to correspond to the direction of curving said curvature section.

19. An endoscope apparatus according to claim 1 wherein a clutch means interrupting said driving force is provided between said driving force generating means and said driving force transmitting means and said control means sets said clutch means in the operating/non-operating state in response to the operation of said change-over switch.

20. An endoscope apparatus according to claim 1 wherein said controlling means feeds/stops feeding an electric power to operate said driving force generating means to said driving force generating means in response to the operation of said switching switch.

21. An endoscope apparatus according to claim 1, wherein said curving switch is provided with said change-over switch.

22. An endoscope apparatus according to claim 1, wherein said curving switch is formed of tiltable levers and said change-over switch is arranged at a top of said levers.

23. An endoscope apparatus according to claim 21, wherein said curving switch is formed of a joy pad consisting of a plurality of on/off switches in response to a direction to which said curvature section is curved and said change-over switch is arranged on said joy pad as an on/off switch.

* * * * *